(12) United States Patent
Mittleman et al.

(10) Patent No.: US 9,607,787 B2
(45) Date of Patent: Mar. 28, 2017

(54) TACTILE FEEDBACK BUTTON FOR A HAZARD DETECTOR AND FABRICATION METHOD THEREOF

(71) Applicant: Google Inc., Mountain View, CA (US)

(72) Inventors: Adam Mittleman, Redwood City, CA (US); Mathias Schmidt, Granada, CA (US); Fred Bould, Menlo Park, CA (US); Matthew L. Rogers, Los Gatos, CA (US); Anthony M. Fadell, Woodside, CA (US)

(73) Assignee: Google Inc., Mountain View, CA (US)

( * ) Notice: Subject to any disclaimer, the term of this patent is extended or adjusted under 35 U.S.C. 154(b) by 705 days.

(21) Appl. No.: 14/047,447

(22) Filed: Oct. 7, 2013

(65) Prior Publication Data

US 2015/0096876 A1    Apr. 9, 2015

(51) Int. Cl.
*H01H 3/12* (2006.01)
*H01H 11/00* (2006.01)
(Continued)

(52) U.S. Cl.
CPC ............. *H01H 11/00* (2013.01); *G08B 17/00* (2013.01); *G08B 17/107* (2013.01);
(Continued)

(58) Field of Classification Search
CPC ................ H01H 9/02–2019/008; G01J 5/025
(Continued)

(56) References Cited

U.S. PATENT DOCUMENTS 2,101,637 A    12/1937   Davis
3,681,603 A     8/1972   Scheidweiler et al.
(Continued)

FOREIGN PATENT DOCUMENTS

DE    196 09 390 A1    9/1997
EP     0 434 926 A2    7/1991
(Continued)

OTHER PUBLICATIONS

International Search Report and Written Opinion mailed on Feb. 20, 2014 for International Application No. PCT/US2013/061021, 18 pages.
(Continued)

*Primary Examiner* — Vanessa Girardi
(74) *Attorney, Agent, or Firm* — Kilpatrick Townsend & Stockton LLP

(57) ABSTRACT

According to one embodiment, a casing of a hazard detector includes a body portion and a button portion. The button portion is coupled with the body portion via a plurality of arms. The arms allow the button portion to be axially movable relative to the body portion and also couple the button portion with the body portion so that tabs that extend radially outward from the button portion are positioned under and contact an inwardly facing surface of the body portion. The arms bias the button portion axially outward relative to the body portion so as maintain contact between the tabs and the inwardly facing surface. In this configuration, when the button portion is pressed at a position off-axis from a central axis of the button portion, the button portion pivots about one or more contact points between one or more tabs and the inwardly facing surface.

22 Claims, 36 Drawing Sheets

(51) Int. Cl.
*H01H 13/50* (2006.01)
*G08B 17/00* (2006.01)
*G08B 17/107* (2006.01)
*G08B 19/00* (2006.01)
*G08B 17/113* (2006.01)
*G08B 21/14* (2006.01)

(52) U.S. Cl.
CPC ............ *G08B 17/113* (2013.01); *G08B 19/00* (2013.01); *G08B 19/005* (2013.01); *H01H 13/50* (2013.01); *G08B 21/14* (2013.01); *Y10T 29/49117* (2015.01); *Y10T 29/49826* (2015.01); *Y10T 29/49947* (2015.01); *Y10T 29/49959* (2015.01)

(58) Field of Classification Search
USPC ......... 200/341, 342, 344, 345, 566; 307/326
See application file for complete search history.

(56) References Cited

U.S. PATENT DOCUMENTS

| | | | |
|---|---|---|---|
| 4,121,110 A | 10/1978 | Solomon | |
| 4,316,577 A | 2/1982 | Adams et al. | |
| 4,319,234 A | 3/1982 | Rice | |
| 4,751,961 A | 6/1988 | Levine et al. | |
| 4,768,706 A | 9/1988 | Parfitt | |
| 4,845,474 A | 7/1989 | Moore et al. | |
| 5,005,365 A | 4/1991 | Lynch | |
| 5,224,649 A | 7/1993 | Brown et al. | |
| 5,294,047 A | 3/1994 | Schwer et al. | |
| 5,303,612 A | 4/1994 | Odom et al. | |
| 5,395,042 A | 3/1995 | Riley et al. | |
| 5,415,346 A | 5/1995 | Bishop | |
| 5,482,209 A | 1/1996 | Cochran et al. | |
| 5,485,954 A | 1/1996 | Guy et al. | |
| 5,555,927 A | 9/1996 | Shah | |
| 5,589,824 A | 12/1996 | Lynch | |
| 5,603,451 A | 2/1997 | Helander et al. | |
| 5,627,531 A | 5/1997 | Posso et al. | |
| 5,673,850 A | 10/1997 | Uptegraph | |
| 5,719,557 A | 2/1998 | Rattman et al. | |
| 5,808,602 A | 9/1998 | Sellers | |
| 5,931,378 A | 8/1999 | Schramm | |
| 6,032,867 A | 3/2000 | Dushane et al. | |
| 6,114,967 A | 9/2000 | Yousif | |
| 6,164,374 A | 12/2000 | Rhodes et al. | |
| 6,206,295 B1 | 3/2001 | LaCoste | |
| 6,211,921 B1 | 4/2001 | Cherian et al. | |
| 6,213,404 B1 | 4/2001 | Dushane et al. | |
| 6,286,764 B1 | 9/2001 | Garvey et al. | |
| 6,298,285 B1 | 10/2001 | Addink et al. | |
| 6,377,182 B1 | 4/2002 | Devine et al. | |
| 6,453,687 B2 | 9/2002 | Sharood et al. | |
| 6,502,758 B2 | 1/2003 | Cottrell | |
| D471,825 S | 3/2003 | Peabody | |
| 6,619,055 B1 | 9/2003 | Addy | |
| 6,636,197 B1 | 10/2003 | Goldenberg et al. | |
| 6,644,557 B1 | 11/2003 | Jacobs | |
| 6,814,299 B1 | 11/2004 | Carey | |
| D503,631 S | 4/2005 | Peabody | |
| 6,951,306 B2 | 10/2005 | DeLuca | |
| 7,000,849 B2 | 2/2006 | Ashworth et al. | |
| 7,083,109 B2 | 8/2006 | Pouchak | |
| 7,108,194 B1 | 9/2006 | Hankins, II | |
| 7,114,554 B2 | 10/2006 | Bergman et al. | |
| 7,140,551 B2 | 11/2006 | de Pauw et al. | |
| 7,141,748 B2 | 11/2006 | Tanaka et al. | |
| 7,156,318 B1 | 1/2007 | Rosen | |
| 7,159,789 B2 | 1/2007 | Schwendinger et al. | |
| 7,159,790 B2 | 1/2007 | Schwendinger et al. | |
| 7,258,280 B2 | 8/2007 | Wolfson | |
| 7,264,175 B2 | 9/2007 | Schwendinger et al. | |
| 7,287,709 B2 | 10/2007 | Proffitt et al. | |
| 7,299,996 B2 | 11/2007 | Garrett et al. | |
| 7,333,880 B2 | 2/2008 | Brewster et al. | |
| D566,587 S | 4/2008 | Rosen | |
| 7,451,937 B2 | 11/2008 | Flood et al. | |
| 7,455,240 B2 | 11/2008 | Chapman, Jr. et al. | |
| 7,509,753 B2 | 3/2009 | Nicosia et al. | |
| 7,555,364 B2 | 6/2009 | Poth et al. | |
| 7,558,648 B2 | 7/2009 | Hoglund et al. | |
| 7,575,179 B2 | 8/2009 | Morrow et al. | |
| 7,579,945 B1 | 8/2009 | Richter et al. | |
| 7,584,899 B2 | 9/2009 | de Pauw et al. | |
| 7,600,694 B2 | 10/2009 | Helt et al. | |
| D603,277 S | 11/2009 | Clausen et al. | |
| 7,614,567 B2 | 11/2009 | Chapman, Jr. et al. | |
| 7,624,931 B2 | 12/2009 | Chapman, Jr. et al. | |
| 7,634,504 B2 | 12/2009 | Amundson | |
| 7,641,126 B2 | 1/2010 | Schultz et al. | |
| 7,693,582 B2 | 4/2010 | Bergman et al. | |
| D614,976 S | 5/2010 | Skafdrup et al. | |
| 7,726,581 B2 | 6/2010 | Naujok et al. | |
| 7,845,576 B2 | 12/2010 | Siddaramanna et al. | |
| 7,904,209 B2 | 3/2011 | Podgorny et al. | |
| 7,904,830 B2 | 3/2011 | Hoglund et al. | |
| 7,994,928 B2 | 8/2011 | Richmond | |
| 8,016,205 B2 | 9/2011 | Drew | |
| D651,529 S | 1/2012 | Mongell et al. | |
| 8,098,166 B2 | 1/2012 | Lang | |
| 8,195,313 B1 | 6/2012 | Fadell et al. | |
| 8,255,090 B2 | 8/2012 | Frader-Thompson et al. | |
| 8,280,536 B1 | 10/2012 | Fadell et al. | |
| 9,046,414 B2 * | 6/2015 | Fadell | G08B 17/00 |
| 2001/0052774 A1 | 12/2001 | Rossi et al. | |
| 2002/0005435 A1 | 1/2002 | Cottrell | |
| 2003/0042320 A1 | 3/2003 | Decker | |
| 2003/0112262 A1 | 6/2003 | Adatia et al. | |
| 2003/0234169 A1 * | 12/2003 | Iwakiri | H01H 13/20 200/341 |
| 2004/0034484 A1 | 2/2004 | Solomita, Jr. et al. | |
| 2004/0256472 A1 | 12/2004 | DeLuca | |
| 2005/0119793 A1 | 6/2005 | Amundson et al. | |
| 2005/0204997 A1 | 9/2005 | Fournier | |
| 2007/0001830 A1 | 1/2007 | Dagci et al. | |
| 2007/0045430 A1 | 3/2007 | Chapman et al. | |
| 2007/0045433 A1 | 3/2007 | Chapman et al. | |
| 2007/0045444 A1 | 3/2007 | Gray et al. | |
| 2007/0050732 A1 | 3/2007 | Chapman et al. | |
| 2007/0158442 A1 | 7/2007 | Chapman et al. | |
| 2007/0158444 A1 | 7/2007 | Naujok et al. | |
| 2007/0173978 A1 | 7/2007 | Fein et al. | |
| 2007/0221225 A1 | 9/2007 | Kutt et al. | |
| 2007/0225867 A1 | 9/2007 | Moorer et al. | |
| 2007/0227721 A1 | 10/2007 | Springer et al. | |
| 2007/0228183 A1 | 10/2007 | Kennedy et al. | |
| 2007/0241203 A1 | 10/2007 | Wagner et al. | |
| 2007/0257120 A1 | 11/2007 | Chapman et al. | |
| 2008/0054082 A1 | 3/2008 | Evans et al. | |
| 2008/0188763 A1 | 8/2008 | John et al. | |
| 2008/0245480 A1 | 10/2008 | Knight et al. | |
| 2008/0281473 A1 | 11/2008 | Pitt | |
| 2008/0290183 A1 | 11/2008 | Laberge et al. | |
| 2008/0294212 A1 | 11/2008 | Siejko et al. | |
| 2009/0001180 A1 | 1/2009 | Siddaramanna et al. | |
| 2009/0140056 A1 | 6/2009 | Leen | |
| 2009/0140057 A1 | 6/2009 | Leen | |
| 2009/0143916 A1 | 6/2009 | Boll et al. | |
| 2009/0283603 A1 | 11/2009 | Peterson et al. | |
| 2010/0084482 A1 | 4/2010 | Kennedy et al. | |
| 2010/0198425 A1 | 8/2010 | Donovan | |
| 2010/0238036 A1 | 9/2010 | Holcombe | |
| 2010/0318227 A1 | 12/2010 | Steinberg et al. | |
| 2011/0015798 A1 | 1/2011 | Golden et al. | |
| 2011/0015802 A1 | 1/2011 | Imes | |
| 2011/0046756 A1 | 2/2011 | Parki | |
| 2011/0298623 A1 | 12/2011 | Lenkeit et al. | |
| 2013/0008787 A1 | 1/2013 | Mammoto et al. | |
| 2013/0241727 A1 | 9/2013 | Coulombe | |
| 2015/0070181 A1 | 3/2015 | Fadell et al. | |

(56) References Cited

U.S. PATENT DOCUMENTS

FOREIGN PATENT DOCUMENTS

| | | |
|---|---|---|
| EP | 0 720 077 A2 | 7/1996 |
| EP | 0 802 471 B1 | 8/1999 |
| EP | 1 065 079 A2 | 1/2001 |
| EP | 1 731 984 A1 | 12/2006 |
| EP | 2 157 492 A2 | 2/2010 |
| GB | 2 212 317 B | 5/1992 |
| JP | 59-106311 A | 6/1984 |
| JP | 9-298780 A | 11/1997 |
| JP | 2002-87050 A | 3/2002 |
| JP | 2003-54290 A | 2/2003 |
| NL | 1024986 C2 | 6/2005 |
| WO | 02/48851 A2 | 6/2002 |
| WO | 2009/073496 A2 | 6/2009 |
| WO | 2011/128416 A2 | 10/2011 |

OTHER PUBLICATIONS

Energy Joule. Datasheet [online]. Ambient Devices, No Date Given [retrieved on Aug. 1, 2012]. Retrieved from the Internet: <URL: http://www.ambientdevices.com/products/energyjoule.html>.
Honeywell CT2700, An Electronic Round Programmable Thermostat—User's Guide, Honeywell, Inc., 1997, 8 pages.
Honeywell CT8775A,C, The digital Round Non-Programmable Thermostats—Owner's Guide, Honeywell International Inc., 2003, 20 pages.
Honeywell T8700C, An Electronic Round Programmable Thermostat—Owner's Guide, Honeywell, Inc., 1997, 12 pages.
Honeywell T8775 The Digital Round Thermostat, Honeywell, 2003, 2 pages.
Honeywell T8775AC Digital Round Thermostat Manual No. 69-1679EF-1, www.honeywell.com/yourhome, Jun. 2004, pp. 1-16.
ICY 3815TT-001 Timer-Thermostat Package Box, ICY BV Product Bar Code No. 8717953007902, 2009, 2 pages.
Introducing the New Smart Si Thermostat. Datasheet [online]. Ecobee. No Date Given [retrieved on Feb. 25, 2013]. Retrieved from the Internet: <URL: https://www.ecobee.com/solutions/home/smart-si/>.
SA720 Smoke Alarm User Manual, First Alert, Aug. 2007, 6 pages.
Smoke Alarm User Manual, Kidde, i9060, Dec. 1, 2009, 2 pages.
The Clever Thermostat, ICY BV Web Page, http://www.icy.nl/en/consumer/products/clever-thermostat, ICY BV, 2012, 1 page.
The Clever Thermostat User Manual and Installation Guide, ICY BV ICY3815 Timer-Thermostat, 2009, pp. 1-36.
U.S. Appl. No. 60/512,886, Volkswagen Rotary Knob for Motor Vehicle—English Translation of German Application filed Oct. 20, 2003.
Arens, et al., Demand Response Electrical Appliance Manager—User Interface Design, Development and Testing, Poster, Demand Response Enabling Technology Development, University of California Berkeley, Retrieved from dr.berkeley.edu/dream/posters/2005_6GUIposter.pdf, 2005, 1 page.
Arens, et al., Demand Response Enabled Thermostat—Control Strategies and Interface, Demand Response Enabling Technology Development Poster, University of California Berkeley, Retrieved from dr.berkeley.edu/dream/posters/2004_11CEC_TstatPoster.pdf, 2004, 1 page.
Arens, et al., Demand Response Enabling Technology Development, Phase I Report: Jun. 2003-Nov. 2005, Jul. 27, P: /DemandRes/ UC Papers/DR-Phase1Report-Final DraftApril24-26.doc, University of California Berkeley, Apr. 4, 2006, pp. 1-108.
Arens, et al., New Thermostat Demand Response Enabling Technology, Poster University of California Berkeley, Jun. 10, 2004.
Auslander, et al., UC Berkeley DR Research Energy Management Group, Power Point Presentation, DR ETD Workshop, State of California Energy Commission, Jun. 11, 2007, pp. 1-35.
Chen, et al., Demand Response-Enabled Residential Thermostat Controls, Abstract, ACEEE Summer Study on Energy Efficiency in Buildings, Mechanical Engineering Dept. and Architecture Dept., University of California Berkeley, 2008, pp. 1-24 through 1-36.
Peffer, et al., Smart Comfort at Home: Design of a Residential Thermostat to Achieve Thermal Comfort, and Save Money and Peak Energy, University of California Berkeley, Mar. 2007.
Green, Thermo Heat Tech Cool, Popular Mechanics Electronic Thermostat Guide, Oct. 1985, pp. 155-158.
Meier, et al., Thermostat Interface Usability: A Survey, Ernest Orlando Lawrence Berkeley National Laboratory, Environmental Energy Technologies Division, Berkeley California, Sep. 2010, pp. 1-73.
Peffer, et al., A Tale of Two Houses: The Human Dimension of Demand Response Enabling Technology from a Case Study of Adaptive Wireless Thermostat, Abstract, ACEEE Summer Study on Energy Efficiency in Buildings, Architecture Dept. and Mechanical Engineering Dept., University of California Berkeley, 2008, pp. 7-242 through 7-253.
Rauchwarnmelder, Installation and User Manual [online]. GIRA [retrieved on Mar. 8, 2013]. Retrieved from the Internet: <URL: http://download.gira.de/data2/23301210.pdf>.
Rauchwarnmelder, Design [online]. GIRA [retrieved on Mar. 3, 2013]. Retrieved from the Internet: <URL: http://www.gira.de/gebaeudetechnik/produkte/sicherheit/rauchmelder/rauchwarnrauchwarnmeld.html?vid=1145>, 2 pages.
Rauchwarnmelder, Datasheet [online]. GIRA [retrieved on Mar. 7, 2013]. Retrieved from the Internet: <URL: http://www.gira.de/gebaeudetechnik/produkte/sicherheit/rauchmelder/rauchwarnmelderdualvds.html>, 6 pages.
Salus, S-Series Digital Thermostat Instruction Manual-ST620 Model No. Instruction Manual, www.salus-tech.com, Version 005, Apr. 29, 2010, 24 pages.
Sanford, iPod (Click Wheel) (2004), www.apple-history.com [retrieved on Apr. 9, 2012]. Retrieved from the Internet: <URL: http://apple-history.com/ipod>, Apr. 9, 2012, 2 pages.
Wright, et al., DR ETD—Summary of New Thermostat, TempNode, & New Meter (UC Berkeley Project), Power Point Presentation, Public Interest Energy Research, University of California Berkeley. Retrieved from: http://dr.berkeley.edu/dream/presentations/2005_6CEC.pdf, 2005, pp. 1-49.

* cited by examiner

TACTILE FEEDBACK BUTTON FOR A HAZARD DETECTOR AND FABRICATION METHOD THEREOF

CROSS-REFERENCE TO RELATED APPLICATIONS

The subject matter of the instant disclosure is related to the subject matter of the following commonly assigned applications, each of which is incorporated by reference herein: International Application No. PCT/US2013/61021 filed Sep. 20, 2013, which claims the benefit of U.S. Prov. Ser. No. 61/704,437 filed Sep. 21, 2012; U.S. Prov. Ser. No. 61/877,186 filed Sep. 12, 2013; U.S. Prov. Ser. No. 61/847,906 filed Jul. 18, 2013; U.S. Prov. Ser. No. 61/847,905 filed Jul. 18, 2013; U.S. Prov. Ser. No. 61/847,937 filed Jul. 18, 2013; U.S. Prov. Ser. No. 61/847,916 filed Jul. 18, 2013; U.S. Prov. Ser. No. 61/847,949 filed Jul. 18, 2013; U.S. Ser. No. 13/835,439 filed Mar. 15, 2013; U.S. Ser. No. 13/835,334 filed Mar. 15, 2013; U.S. Ser. No. 13/835,523 filed Mar. 15, 2013; and U.S. Ser. No. 13/830,795 filed Mar. 14, 2013.

BACKGROUND OF THE INVENTION

Some homes today are equipped with smart home networks to provide automated control of devices, appliances and systems, such as heating, ventilation, and air conditioning ("HVAC") system, lighting systems, alarm systems, home theater and entertainment systems. Smart home networks may include control panels that a person may use to input settings, preferences, and scheduling information that the smart home network uses to provide automated control the various devices, appliances and systems in the home. For example, a person may input a desired temperature and a schedule indicating when the person is away from home. The home automation system uses this information to control the HVAC system to heat or cool the home to the desired temperature when the person is home, and to conserve energy by turning off power-consuming components of the HVAC system when the person is away from the home. Also, for example, a person may input a preferred nighttime lighting scheme for watching television. In response, when the person turns on the television at nighttime, the home automation system automatically adjusts the lighting in the room to the preferred scheme.

Hazard detection systems such as smoke detectors, carbon monoxide detectors, combination smoke and carbon monoxide detectors, as well as systems for detecting other dangerous conditions have been used in residential, commercial, and industrial settings for safety considerations. When these systems detect the presence of a dangerous condition, they often sound an audible alarm. The audible alarm is often, by design, an extremely loud and ear piercing sound in order to increase the likelihood of seizing the attention of the occupants. Some hazard detectors may permit a user to press a button located on the cover of the unit, sometimes termed a hush button or temporary silence button, when they know an alarm to be caused by a non-emergency situation, such as smoke from cooking. When the hush button or temporary silence button is pressed, the audible alarm noise is temporarily silenced for a predetermined interval of time, such as in the range of four to ten minutes, during which the user has an opportunity to address the situation, such as by opening a window, without being required to endure the ear-piercing sound of the alarm. If the condition persists at the end of the predetermined interval of time, then the audible alarm noise resumes. Other buttons may be provided on hazard detectors for other purposes.

BRIEF SUMMARY OF THE INVENTION

Embodiments described herein provide smart hazard detector devices and methods therefor. In some embodiments the hazard detector devices may include a tactile feedback button that provides an improved and relatively uniform click feel to users. According to one embodiment, the tactile feedback button may be incorporated within a front casing of the hazard detector. For example, a front casing of a hazard detector may include a body portion that has an outwardly facing surface that faces a room within which the hazard detector is positioned, and may further comprise an inwardly facing surface that faces opposite the outwardly facing surface. The body portion may be coupled with a back plate to define a housing having an interior region within which components of the hazard detector are contained. The front casing may also include a button portion that is coupled with the body portion via a plurality of arms. The plurality of arms may allow the button portion to be axially movable relative to the body portion such as, for example, to activate a switch positioned axially behind the button portion to provide input to the hazard detector from a user. The button portion may have a plurality of tabs that extend radially outward from a peripheral edge of the button portion.

Each tab may be positioned under and contact the inwardly facing surface of the body portion so that when a force is applied to the button portion at a position substantially offset from a central axis of the button portion, the button portion pivots about one or more contact points between a respective tab or tabs and the inwardly facing surface of the body portion. The plurality of arms may be coupled with the button portion and the body portion in a manner that biases the button portion axially outward relative to the body portion in order to press the plurality of tabs against the inwardly facing surface of the body portion.

In some embodiments, each tab of the plurality of tabs is positioned under a flange of the body portion. In some embodiments, each of the plurality of arms includes a proximal end, a distal end, and a main body that extends between the proximal and distal ends. Each of the plurality of arms may be fixed to the body portion at the proximal end and fixed to the button portion at the distal end with the main body extending circumferentially around a portion of the button portion. In some embodiments, the distal end of each arm may be coupled with a tab of the button portion.

The body portion may include a relatively large population of relatively small openings that allow air to substantially freely flow to one or more components contained within the housing through the body portion in a relatively unimpeded manner. In some embodiments, a collective area of the openings of the body portion may be between about 20% and 40% of the body portion. In some embodiments, the button portion may be positioned substantially centrally relative to the body portion. In one embodiment, the button portion may include four radially extending tabs that are each positioned under and contact the inwardly facing surface of the body portion to define four pivot points about which the button portion is pivotable. In some embodiment, the button portion is integrally formed with the body portion so that the body portion and button portion comprise a single component. In some embodiments, a Fresnel lens member may be attached to the button portion. The Fresnel lens member may function as a pressable button and also as a lens for a passive infrared (PIR) sensor that is positioned axially inward of the Fresnel lens member.

According to another embodiment, a front casing of a hazard detector is provided. The front casing includes a body portion having an outwardly facing surface that faces a room within which the hazard detector is positioned and an inwardly facing surface that faces opposite the outwardly facing surface. The body portion is couplable with a back plate to define a housing having an interior region within which components of the hazard detector are contained. The front casing also includes a button portion that is coupled with the body portion via a plurality of arms. The plurality of arms allows the button portion to be axially movable relative to the body portion. The button portion is coupled with the body portion so that one or more tabs that extend radially outward from a peripheral edge of the button portion are positioned under and contact the inwardly facing surface of the body portion.

In this configuration, when a force is applied to the button portion at a position substantially off-axis from a central axis of the button portion, the button portion pivots about one or more points of contact between the one or more tabs and the inwardly facing surface of the body portion. Further, in this configuration, the plurality of arms couple the button portion to the body portion such that the button portion is biased axially outward relative to the body portion.

In some embodiments, a Fresnel lens member is attached to the button portion. The Fresnel lens member may function both as a pressable button and as a lens for a passive infrared (PIR) sensor that is positioned axially inward of the Fresnel lens member. The PIR sensor may be positioned on an outwardly facing surface of the button portion. In some embodiments, the body portion includes a relatively large population of relatively small openings that allow air to substantially freely flow to one or more components contained within the housing through the body portion in a relatively unimpeded manner. A collective area of the openings of the body portion may be between about 20% and 40% of the body portion. In some embodiments, the button portion is positioned substantially centrally relative to the body portion. The button portion may be integrally formed with the body portion so that the body portion and button portion comprise a single component.

According to another embodiment, a method of making a casing having a pressable button portion is provided. The method includes forming a casing component and repositioning a button portion of the casing component relative to a body portion of the casing component. The casing component includes the body portion, which has an outwardly facing surface and an inwardly facing surface opposite the outwardly facing surface. The casing component also has the button portion, which includes a plurality of tabs that extend radially outward from a peripheral edge of the button portion. The casing component further has a plurality of arms that attach the button portion to the body portion. The plurality of arms allows the button portion to be movable relative to the body portion. The casing component is formed so that the tabs are positioned axially outward relative to the inwardly facing surface of the body portion. When the button portion is repositioned relative to the body portion, the plurality of tabs are positioned axially inward of the inwardly facing surface of the body portion. Repositioning the button portion also causes the plurality of arms to bias the button portion axially outward relative to the body portion so that the plurality of tabs press against the inwardly facing surface of the body portion.

Contact between the plurality of tabs and the inwardly facing surface of the body portion causes the button portion to pivot relative to the body portion when a force is applied to the button portion at a position substantially off-axis from a central axis of the button portion. In some embodiments, the body portion, button portion, and the plurality of arms may be integrally molded as a single component. In some embodiments, the method may further include coupling a Fresnel lens member to the button portion. The Fresnel lens member may function as a pressable button and also as a lens for a passive infrared (PIR) sensor that is positioned axially inward of the Fresnel lens member.

According to another embodiment, a method of making a casing having a pressable button portion is provided. The method includes forming a casing component having a body portion and a button portion. The casing component is formed such that one or more tabs that extend radially outward from a peripheral edge of the button portion are positioned axially outward relative to an inwardly facing surface of the body portion. The method also includes repositioning the button portion relative to the body portion so that the one or more tabs of the button portion are positioned axially inward of the inwardly facing surface of the body portion. Repositioning the button portion relative to the body portion in this manner causes the one or more tabs to be biased radially outwardly against the inwardly facing surface of the body portion.

In some embodiments, the method may further include coupling a Fresnel lens member to the button portion. The Fresnel lens member may function as a pressable button and also as a lens for a passive infrared (PIR) sensor that is positioned axially inward of the Fresnel lens member. In some embodiments, the body portion and the button portion may be integrally molded as a single component.

BRIEF DESCRIPTION OF THE DRAWINGS

The present invention is described in conjunction with the appended figures.

Figure 1:
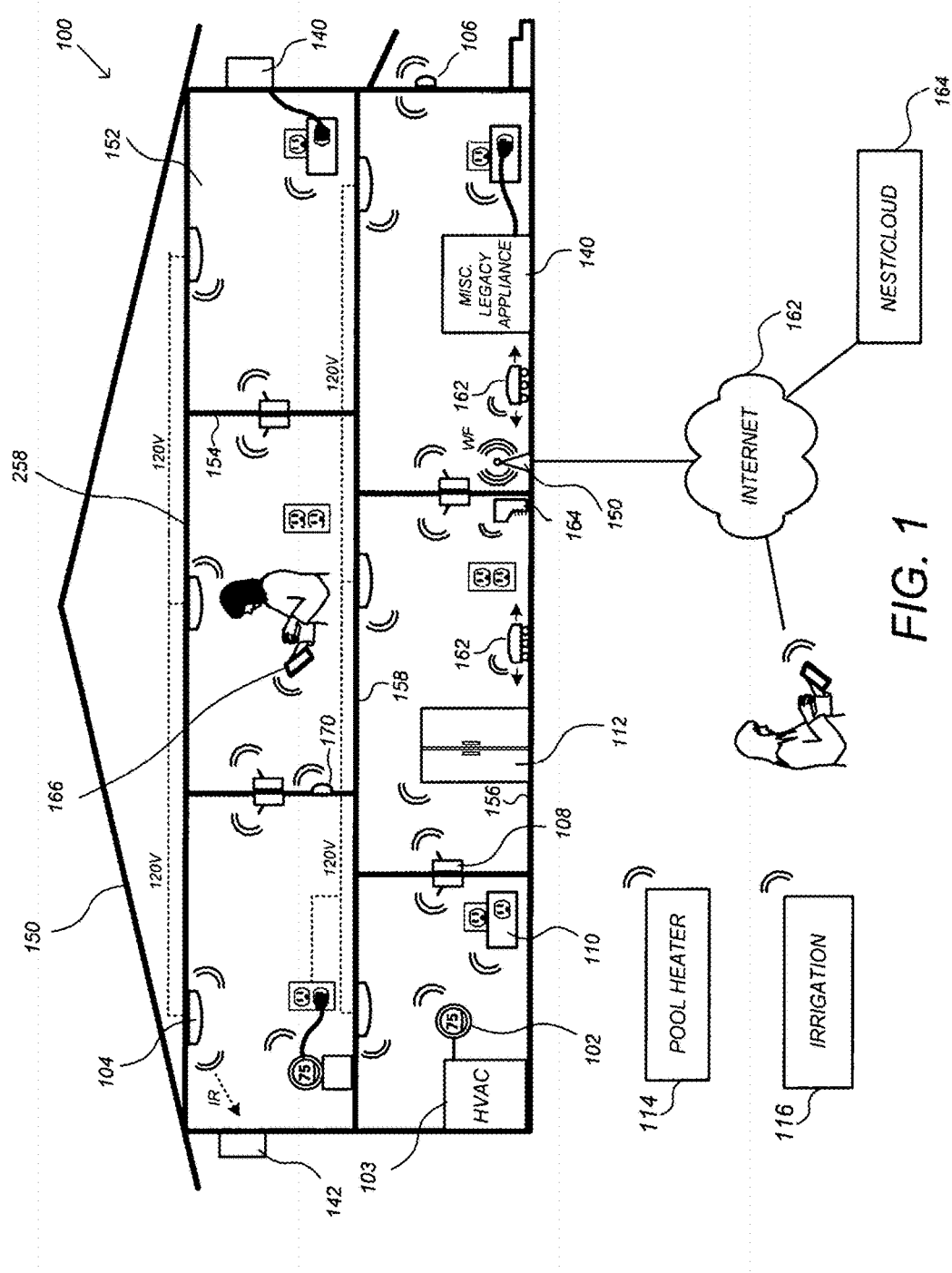
FIG. 1 an example of a smart-home environment within which one or more of the devices, methods, systems, services, and/or computer program products described further herein will be applicable, according to an embodiment.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The term "machine-readable medium" includes, but is not limited to portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Turning to the figures, FIG. 1 illustrates an example of a smart-home environment 100 within which one or more of the devices, methods, systems, services, and/or computer program products described further herein can be applicable. The depicted smart-home environment 100 includes a structure 150, which can include, e.g., a house, office building, garage, or mobile home. It will be appreciated that devices can also be integrated into a smart-home environment 100 that does not include an entire structure 150, such as an apartment, condominium, or office space. Further, the smart home environment can control and/or be coupled to devices outside of the actual structure 150. Indeed, several devices in the smart home environment need not physically be within the structure 150 at all. For example, a device controlling a pool heater or irrigation system can be located outside of the structure 150.

The depicted structure 150 includes a plurality of rooms 152, separated at least partly from each other via walls 154. The walls 154 can include interior walls or exterior walls. Each room can further include a floor 156 and a ceiling 158. Devices can be mounted on, integrated with and/or supported by a wall 154, floor 156 or ceiling 158.

In some embodiments, the smart-home environment 100 of FIG. 1 includes a plurality of devices, including intelligent, multi-sensing, network-connected devices, that can integrate seamlessly with each other and/or with a central server or a cloud-computing system to provide any of a variety of useful smart-home objectives. The smart-home environment 100 may include one or more intelligent, multi-sensing, network-connected thermostats 102 (herein after referred to as "smart thermostats 102"), one or more intelligent, network-connected, multi-sensing hazard detection units 104 (herein after referred to as "smart hazard detectors 104"), and one or more intelligent, multi-sensing, network-connected entryway interface devices 106 (herein after referred to as "smart doorbells 104"). According to embodiments, the smart thermostat 102 detects ambient climate characteristics (e.g., temperature and/or humidity) and controls a HVAC system 103 accordingly. The smart hazard detector 104 may detect the presence of a hazardous substance or a substance indicative of a hazardous substance (e.g., smoke, fire, or carbon monoxide). The smart doorbell 106 may detect a person's approach to or departure from a location (e.g., an outer door), control doorbell functionality, announce a person's approach or departure via audio or visual means, or control settings on a security system (e.g., to activate or deactivate the security system when occupant go and come).

In some embodiments, the smart-home environment 100 of FIG. 1 further includes one or more intelligent, multi-sensing, network-connected wall switches 108 (herein after referred to as "smart wall switches 108"), along with one or more intelligent, multi-sensing, network-connected wall plug interfaces 110 (herein after referred to as "smart wall plugs 110"). The smart wall switches 108 may detect ambient lighting conditions, detect room-occupancy states, and control a power and/or dim state of one or more lights. In some instances, smart wall switches 108 may also control a power state or speed of a fan, such as a ceiling fan. The smart wall plugs 110 may detect occupancy of a room or enclosure and control supply of power to one or more wall plugs (e.g., such that power is not supplied to the plug if nobody is at home).

Still further, in some embodiments, the smart-home environment 100 of FIG. 1 includes a plurality of intelligent, multi-sensing, network-connected appliances 112 (herein after referred to as "smart appliances 112"), such as refrigerators, stoves and/or ovens, televisions, washers, dryers, lights, stereos, intercom systems, garage-door openers, floor fans, ceiling fans, wall air conditioners, pool heaters, irrigation systems, security systems, and so forth. According to embodiments, the network-connected appliances 112 are made compatible with the smart-home environment by cooperating with the respective manufacturers of the appliances. For example, the appliances can be space heaters, window AC unites, motorized duct vents, etc. When plugged in, an appliance can announce itself to the smart-home network, such as by indicating what type of appliance it is, and it can automatically integrate with the controls of the smart-home. Such communication by the appliance to the smart home can be facilitated by any wired or wireless communication protocols known by those having ordinary skill in the art. The smart home also can include a variety of non-communicating legacy appliances 140, such as old conventional washer/dryers, refrigerators, and the like which can be controlled, albeit coarsely (ON/OFF), by virtue of the smart wall plugs 110. The smart-home environment 100 can further include a variety of partially communicating legacy appliances 142, such as infrared ("IR") controlled wall air conditioners or other IR-controlled devices, which can be controlled by IR signals provided by the smart hazard detectors 104 or the smart wall switches 108.

According to embodiments, the smart thermostats 102, the smart hazard detectors 104, the smart doorbells 106, the smart wall switches 108, the smart wall plugs 110, and other devices of the smart-home environment 100 are modular and can be incorporated into older and new houses. For example, the devices are designed around a modular platform consisting of two basic components: a head unit and a back plate, which is also referred to as a docking station. Multiple configurations of the docking station are provided so as to be compatible with any home, such as older and newer homes. However, all of the docking stations include a standard head-connection arrangement, such that any head unit can be removably attached to any docking station. Thus, in some embodiments, the docking stations are interfaces that serve as physical connections to the structure and the voltage wiring of the homes, and the interchangeable head units contain all of the sensors, processors, user interfaces, the batteries, and other functional components of the devices.

Many different commercial and functional possibilities for provisioning, maintenance, and upgrade are possible. For example, after years of using any particular head unit, a user will be able to buy a new version of the head unit and simply plug it into the old docking station. There are also many different versions for the head units, such as low-cost versions with few features, and then a progression of increasingly-capable versions, up to and including extremely fancy head units with a large number of features. Thus, it should be appreciated that the various versions of the head units can all be interchangeable, with any of them working when placed into any docking station. This can advantageously encourage sharing and re-deployment of old head units—for example, when an important high-capability head unit, such as a hazard detector, is replaced by a new version of the head unit, then the old head unit can be re-deployed to a backroom or basement, etc. According to embodiments, when first plugged into a docking station, the head unit can ask the user (by 2D LCD display, 2D/3D holographic projection, voice interaction, etc.) a few simple questions such as, "Where am I" and the user can indicate "living room", "kitchen" and so forth.

The smart-home environment 100 may also include communication with devices outside of the physical home but within a proximate geographical range of the home. For example, the smart-home environment 100 may include a pool heater monitor 114 that communicates a current pool temperature to other devices within the smart-home environment 100 or receives commands for controlling the pool temperature. Similarly, the smart-home environment 100 may include an irrigation monitor 116 that communicates information regarding irrigation systems within the smart-home environment 100 and/or receives control information for controlling such irrigation systems. According to embodiments, an algorithm is provided for considering the geographic location of the smart-home environment 100, such as based on the zip code or geographic coordinates of the home. The geographic information is then used to obtain data helpful for determining optimal times for watering, such data may include sun location information, temperature, due point, soil type of the land on which the home is located, etc.

By virtue of network connectivity, one or more of the smart-home devices of FIG. 1 can further allow a user to interact with the device even if the user is not proximate to the device. For example, a user can communicate with a device using a computer (e.g., a desktop computer, laptop computer, or tablet) or other portable electronic device (e.g., a smartphone) 166. A webpage or app can be configured to receive communications from the user and control the device based on the communications and/or to present information about the device's operation to the user. For example, the user can view a current setpoint temperature for a device and adjust it using a computer. The user can be in the structure during this remote communication or outside the structure.

As discussed, users can control the smart thermostat and other smart devices in the smart-home environment 100 using a network-connected computer or portable electronic device 166. In some examples, some or all of the occupants (e.g., individuals who live in the home) can register their device 166 with the smart-home environment 100. Such registration can be made at a central server to authenticate the occupant and/or the device as being associated with the home and to give permission to the occupant to use the device to control the smart devices in the home. An occupant can use their registered device 166 to remotely control the smart devices of the home, such as when the occupant is at work or on vacation. The occupant may also use their registered device to control the smart devices when the occupant is actually located inside the home, such as when the occupant sitting on a couch inside the home. It should be appreciated that instead of or in addition to registering devices 166, the smart-home environment 100 makes inferences about which individuals live in the home and are therefore occupants and which devices 166 are associated with those individuals. As such, the smart-home environment "learns" who is an occupant and permits the devices 166 associated with those individuals to control the smart devices of the home.

In some instances, guests desire to control the smart devices. For example, the smart-home environment may receive communication from an unregistered mobile device of an individual inside of the home, where said individual is not recognized as an occupant of the home. Further, for example, smart-home environment may receive communication from a mobile device of an individual who is known to be or who is registered as a guest.

According to embodiments, a guest-layer of controls can be provided to guests of the smart-home environment 100. The guest-layer of controls gives guests access to basic controls (e.g., a judicially selected subset of features of the smart devices), such as temperature adjustments, but it locks out other functionalities. The guest layer of controls can be thought of as a "safe sandbox" in which guests have limited controls, but they do not have access to more advanced controls that could fundamentally alter, undermine, damage, or otherwise impair the occupant-desired operation of the smart devices. For example, the guest layer of controls won't permit the guest to adjust the heat-pump lockout temperature.

A use case example of this is when a guest in a smart home, the guest could walk up to the thermostat and turn the dial manually, but the guest may not want to walk the house "hunting" the thermostat, especially at night while the home is dark and others are sleeping. Further, the guest may not want to go through the hassle of downloading the necessary application to their device for remotely controlling the thermostat. In fact, the guest may not have to the home owner's login credentials, etc., and therefore cannot remotely control the thermostat via such an application. Accordingly, according to embodiments of the invention, the guest can open a mobile browser on their mobile device, type a keyword, such as "NEST" into the URL field and tap "Go" or "Search", etc. In response the device presents with guest with a user interface, which allows the guest to move the target temperature between a limited range, such as 65 and 80 degrees Fahrenheit. As discussed, the user interface provides a guest layer of controls that are limited to basic functions. The guest cannot change the target humidity, modes, or view energy history.

According to embodiments, to enable guests to access the user interface that provides the guest layer of controls, a local webserver is provided that is accessible in the local area network (LAN). It does not require a password, because physical presence inside the home is established reliably enough by the guest's presence on the LAN. In some embodiments, during installation of the smart device, such as the smart thermostat, the home owner is asked if they want to enable a Local Web App (LWA) on the smart device. Business owners will likely say no; home owners will likely say yes. When the LWA option is selected, the smart device broadcasts to the LAN that the above referenced keyword, such as "NEST", is now a host alias for its local web server. Thus, no matter whose home a guest goes to, that same keyword (e.g., "NEST" is always the URL you use to access the LWA, provided the smart device is purchased from the same manufacturer. Further, according to embodiments, if there is more than one smart device on the LAN, the second and subsequent smart devices do not offer to set up another LWA. Instead, they register themselves as target candidates with the master LWA. And in this case the LWA user would be asked which smart device they want to change the temperature on before getting a more directed user interface for the particular smart device they choose.

According to embodiments, a guest layer of controls may also be provided to users by means other than a device 166. For example, the smart device, such as the smart thermostat, may be equipped with walkup-identification technology (e.g., face recognition, RFID, ultrasonic sensors) that "fingerprints" or creates a "signature" for the occupants of the home. The walkup-identification technology can be the same as or similar to the fingerprinting and signature creating techniques descripted in other sections of this application. In operation, when a person who does not live in the home or is otherwise not registered with or whose fingerprint or signature is not recognized by the smart home "walks up" to a smart device, the smart devices provides the guest with the guest layer of controls, rather than full controls.

As described below, the smart thermostat and other smart devices "learn" by observing occupant behavior. For example, the smart thermostat learns occupants preferred temperature set-points for mornings and evenings, and it learns when the occupants are asleep or awake, as well as when the occupants are typically away or at home, for example. According to embodiments, when a guest controls the smart devices, such as the smart thermostat, the smart devices do not "learn" from the guest. This prevents the guest's adjustments and controls from affecting the learned preferences of the occupants.

According to some embodiments, a smart television remote control is provided. The smart remote control recognizes occupants by thumbprint, visual identification, RFID, etc., and it recognizes users as guests or as someone belonging to a particular class having limited control and access (e.g., child). Upon recognizing the user as a guest or someone belonging to a limited class, the smart remote control only permits that user to view a subset of channels and to make limited adjustments to the settings of the television and other devices. For example, a guest cannot adjust the digital video recorder (DVR) settings, and a child is limited to viewing child-appropriate programming.

According to some embodiments, similar controls are provided for other instruments, utilities, and devices in the house. For example, sinks, bathtubs, and showers can be controlled by smart spigots that recognize users as guests or as children and therefore prevents water from exceeding a designated temperature that is considered safe.

In some embodiments, in addition to containing processing and sensing capabilities, each of the devices 102, 104, 106, 108, 110, 112, 114, and 116 (collectively referred to as "the smart devices") is capable of data communications and information sharing with any other of the smart devices, as well as to any central server or cloud-computing system or any other device that is network-connected anywhere in the world. The required data communications can be carried out using any of a variety of custom or standard wireless protocols (Wi-Fi, ZigBee, 6LoWPAN, etc.) and/or any of a variety of custom or standard wired protocols (CAT6 Ethernet, HomePlug, etc.)

According to embodiments, all or some of the smart devices can serve as wireless or wired repeaters. For example, a first one of the smart devices can communicate with a second one of the smart device via a wireless router 160. The smart devices can further communicate with each other via a connection to a network, such as the Internet 162. Through the Internet 162, the smart devices can communicate with a central server or a cloud-computing system 164. The central server or cloud-computing system 164 can be associated with a manufacturer, support entity, or service provider associated with the device. For one embodiment, a user may be able to contact customer support using a device itself rather than needing to use other communication means such as a telephone or Internet-connected computer. Further, software updates can be automatically sent from the central server or cloud-computing system 164 to devices (e.g., when available, when purchased, or at routine intervals).

According to embodiments, the smart devices combine to create a mesh network of spokesman and low-power nodes in the smart-home environment 100, where some of the smart devices are "spokesman" nodes and others are "low-powered" nodes. Some of the smart devices in the smart-home environment 100 are battery powered, while others have a regular and reliable power source, such as by connecting to wiring (e.g., to 120V line voltage wires) behind the walls 154 of the smart-home environment. The smart devices that have a regular and reliable power source are referred to as "spokesman" nodes. These nodes are equipped with the capability of using any wireless protocol or manner to facilitate bidirectional communication with any of a variety of other devices in the smart-home environment 100 as well as with the central server or cloud-computing system 164. On the other hand, the devices that are battery powered are referred to as "low-power" nodes. These nodes tend to be smaller than spokesman nodes and can only communicate using wireless protocol that requires very little power, such as Zigbee, 6LoWPAN, etc. Further, some, but not all, low-power nodes are incapable of bidirectional communication. These low-power nodes send messages, but they are unable to "listen". Thus, other devices in the smart-home environment 100, such as the spokesman nodes, cannot send information to these low-power nodes.

As described, the smart devices serve as low-power and spokesman nodes to create a mesh network in the smart-home environment 100. Individual low-power nodes in the smart-home environment regularly send out messages regarding what they are sensing, and the other low-powered nodes in the smart-home environment—in addition to sending out their own messages—repeat the messages, thereby causing the messages to travel from node to node (i.e., device to device) throughout the smart-home environment 100. The spokesman nodes in the smart-home environment 100 are able to "drop down" to low-powered communication protocols to receive these messages, translate the messages to other communication protocols, and send the translated messages to other spokesman nodes and/or the central server or cloud-computing system 164. Thus, the low-powered nodes using low-power communication protocols are able send messages across the entire smart-home environment 100 as well as over the Internet 162 to the central server or cloud-computing system 164. According to embodiments, the mesh network enables the central server or cloud-computing system 164 regularly receive data from all of the smart devices in the home, make inferences based on the data, and send commands back to individual one of the smart devices to accomplish some of the smart-home objectives descried herein.

As described, the spokesman nodes and some of the low-powered nodes are capable of "listening". Accordingly, users, other devices, and the central server or cloud-computing system 164 can communicate controls to the low-powered nodes. For example, a user can use the portable electronic device (e.g., a smartphone) 166 to send commands over the Internet to the central server or cloud-computing system 164, which then relays the commands to the spokesman nodes in the smart-home environment 100. The spokesman nodes drop down to a low-power protocol to communicate the commands to the low-power nodes throughout the smart-home environment, as well as to other spokesman nodes that did not receive the commands directly from the central server or cloud-computing system 164.

An example of a low-power node is a smart nightlight 170. In addition to housing a light source, the smart nightlight 170 houses an occupancy sensor, such as an ultrasonic or passive IR sensor, and an ambient light sensor, such as a photoresistor or a single-pixel sensor that measures light in the room. In some embodiments, the smart nightlight 170 is configured to activate the light source when its ambient light sensor detects that the room is dark and when its occupancy sensor detects that someone is in the room. In other embodiments, the smart nightlight 170 is simply configured to activate the light source when its ambient light sensor detects that the room is dark. Further, according to embodiments, the smart nightlight 170 includes a low-power wireless communication chip (e.g., ZigBee chip) that regularly sends out messages regarding the occupancy of the room and the amount of light in the room, including instantaneous messages coincident with the occupancy sensor detecting the presence of a person in the room. As mentioned above, these messages may be sent wirelessly, using the mesh network, from node to node (i.e., smart device to smart device) within the smart-home environment 100 as well as over the Internet 162 to the central server or cloud-computing system 164.

Other examples of low-powered nodes include battery-operated versions of the smart hazard detectors 104. These smart hazard detectors 104 are often located in an area without access to constant and reliable power and, as discussed in detail below, may include any number and type of sensors, such as smoke/fire/heat sensors, carbon monoxide/dioxide sensors, occupancy/motion sensors, ambient light sensors, temperature sensors, humidity sensors, and the like. Furthermore, smart hazard detectors 104 can send messages that correspond to each of the respective sensors to the other devices and the central server or cloud-computing system 164, such as by using the mesh network as described above.

Examples of spokesman nodes include smart doorbells 106, smart thermostats 102, smart wall switches 108, and smart wall plugs 110. These devices 102, 106, 108, and 110 are often located near and connected to a reliable power source, and therefore can include more power-consuming components, such as one or more communication chips capable of bidirectional communication in any variety of protocols.

In some embodiments, these low-powered and spokesman nodes (e.g., devices 102, 104, 106, 108, 110, 112, and 170) can function as "tripwires" for an alarm system in the smart-home environment. For example, in the event a perpetrator circumvents detection by alarm sensors located at windows, doors, and other entry points of the smart-home environment 100, the alarm could be triggered upon receiving an occupancy, motion, heat, sound, etc. message from one or more of the low-powered and spokesman nodes in the mesh network. For example, upon receiving a message from a smart nightlight 170 indicating the presence of a person, the central server or cloud-computing system 164 or some other device could trigger an alarm, provided the alarm is armed at the time of detection. Thus, the alarm system could be enhanced by various low-powered and spokesman nodes located throughout the smart-home environment 100. In this example, a user could enhance the security of the smart-home environment 100 by buying and installing extra smart nightlights 170.

In some embodiments, the mesh network can be used to automatically turn on and off lights as a person transitions from room to room. For example, the low-powered and spokesman nodes (e.g., devices 102, 104, 106, 108, 110, 112, and 170) detect the person's movement through the smart-home environment and communicate corresponding messages through the mesh network. Using the messages that indicate which rooms are occupied, the central server or cloud-computing system 164 or some other device activates and deactivates the smart wall switches 108 to automatically provide light as the person moves from room to room in the smart-home environment 100. Further, users may provide pre-configuration information that indicates which smart wall plugs 110 provide power to lamps and other light sources, such as the smart nightlight 170. Alternatively, this mapping of light sources to wall plugs 110 can be done automatically (e.g., the smart wall plugs 110 detect when a light source is plugged into it, and it sends a corresponding message to the central server or cloud-computing system 164). Using this mapping information in combination with messages that indicate which rooms are occupied, the central server or cloud-computing system 164 or some other device activates and deactivates the smart wall plugs 110 that provide power to lamps and other light sources so as to track the person's movement and provide light as the person moves from room to room.

In some embodiments, the mesh network of low-powered and spokesman nodes can be used to provide exit lighting in the event of an emergency. In some instances, to facilitate this, users provide pre-configuration information that indicates exit routes in the smart-home environment 100. For example, for each room in the house, the user provides a map of the best exit route. It should be appreciated that instead of a user providing this information, the central server or cloud-computing system 164 or some other device could the automatically determine the routes using uploaded maps, diagrams, architectural drawings of the smart-home house, as well as using a map generated based on positional information obtained from the nodes of the mesh network (e.g., positional information from the devices is used to construct a map of the house). In operation, when an alarm is activated (e.g., when one or more of the smart hazard detector 104 detects smoke and activates an alarm), the central server or cloud-computing system 164 or some other device uses occupancy information obtained from the low-powered and spokesman nodes to determine which rooms are occupied and then turns on lights (e.g., nightlights 170, wall switches 108, wall plugs 110 that power lamps, etc.) along the exit routes from the occupied rooms so as to provide emergency exit lighting.

Further included and illustrated in the exemplary smart-home environment 100 of FIG. 1 are service robots 162 each configured to carry out, in an autonomous manner, any of a variety of household tasks. For some embodiments, the service robots 162 can be respectively configured to perform floor sweeping, floor washing, etc. in a manner similar to that of known commercially available devices such as the ROOMBA™ and SCOOBA™ products sold by iRobot, Inc. of Bedford, Mass. Tasks such as floor sweeping and floor washing can be considered as "away" or "while-away" tasks for purposes of the instant description, as it is generally more desirable for these tasks to be performed when the occupants are not present. For other embodiments, one or more of the service robots 162 are configured to perform tasks such as playing music for an occupant, serving as a localized thermostat for an occupant, serving as a localized air monitor/purifier for an occupant, serving as a localized baby monitor, serving as a localized hazard detector for an occupant, and so forth, it being generally more desirable for such tasks to be carried out in the immediate presence of the human occupant. For purposes of the instant description, such tasks can be considered as "human-facing" or "human-centric" tasks.

When serving as a localized thermostat for an occupant, a particular one of the service robots 162 can be considered to be facilitating what can be called a "personal comfort-area network" for the occupant, with the objective being to keep the occupant's immediate space at a comfortable temperature wherever that occupant may be located in the home. This can be contrasted with conventional wall-mounted room thermostats, which have the more attenuated objective of keeping a statically-defined structural space at a comfortable temperature. According to one embodiment, the localized-thermostat service robot 162 is configured to move itself into the immediate presence (e.g., within five feet) of a particular occupant who has settled into a particular location in the home (e.g. in the dining room to eat their breakfast and read the news). The localized-thermostat service robot 162 includes a temperature sensor, a processor, and wireless communication components configured such that control communications with the HVAC system, either directly or through a wall-mounted wirelessly communicating thermostat coupled to the HVAC system, are maintained and such that the temperature in the immediate vicinity of the occupant is maintained at their desired level. If the occupant then moves and settles into another location (e.g. to the living room couch to watch television), the localized-thermostat service robot 162 proceeds to move and park itself next to the couch and keep that particular immediate space at a comfortable temperature.

Technologies by which the localized-thermostat service robot 162 (and/or the larger smart-home system of FIG. 1) can identify and locate the occupant whose personal-area space is to be kept at a comfortable temperature can include, but are not limited to, RFID sensing (e.g., person having an RFID bracelet, RFID necklace, or RFID key fob), synthetic vision techniques (e.g., video cameras and face recognition processors), audio techniques (e.g., voice, sound pattern, vibration pattern recognition), ultrasound sensing/imaging techniques, and infrared or near-field communication (NFC) techniques (e.g., person wearing an infrared or NFC-capable smartphone), along with rules-based inference engines or artificial intelligence techniques that draw useful conclusions from the sensed information (e.g., if there is only a single occupant present in the home, then that is the person whose immediate space should be kept at a comfortable temperature, and the selection of the desired comfortable temperature should correspond to that occupant's particular stored profile).

When serving as a localized air monitor/purifier for an occupant, a particular service robot 162 can be considered to be facilitating what can be called a "personal health-area network" for the occupant, with the objective being to keep the air quality in the occupant's immediate space at healthy levels. Alternatively or in conjunction therewith, other health-related functions can be provided, such as monitoring the temperature or heart rate of the occupant (e.g., using finely remote sensors, near-field communication with on-person monitors, etc.). When serving as a localized hazard detector for an occupant, a particular service robot 162 can be considered to be facilitating what can be called a "personal safety-area network" for the occupant, with the objective being to ensure there is no excessive carbon monoxide, smoke, fire, etc., in the immediate space of the occupant. Methods analogous to those described above for personal comfort-area networks in terms of occupant identifying and tracking are likewise applicable for personal health-area network and personal safety-area network embodiments.

According to some embodiments, the above-referenced facilitation of personal comfort-area networks, personal health-area networks, personal safety-area networks, and/or other such human-facing functionalities of the service robots 162, are further enhanced by logical integration with other smart sensors in the home according to rules-based inferencing techniques or artificial intelligence techniques for achieving better performance of those human-facing functionalities and/or for achieving those goals in energy-conserving or other resource-conserving ways. Thus, for one embodiment relating to personal health-area networks, the air monitor/purifier service robot 162 can be configured to detect whether a household pet is moving toward the currently settled location of the occupant (e.g., using on-board sensors and/or by data communications with other smart-home sensors along with rules-based inferencing/artificial intelligence techniques), and if so, the air purifying rate is immediately increased in preparation for the arrival of more airborne pet dander. For another embodiment relating to personal safety-area networks, the hazard detector service robot 162 can be advised by other smart-home sensors that the temperature and humidity levels are rising in the kitchen, which is nearby to the occupant's current dining room location, and responsive to this advisory the hazard detector service robot 162 will temporarily raise a hazard detection threshold, such as a smoke detection threshold, under an inference that any small increases in ambient smoke levels will most likely be due to cooking activity and not due to a genuinely hazardous condition.

The above-described "human-facing" and "away" functionalities can be provided, without limitation, by multiple distinct service robots 162 having respective dedicated ones of such functionalities, by a single service robot 162 having an integration of two or more different ones of such functionalities, and/or any combinations thereof (including the ability for a single service robot 162 to have both "away" and "human facing" functionalities) without departing from the scope of the present teachings. Electrical power can be provided by virtue of rechargeable batteries or other rechargeable methods, with FIG. 1 illustrating an exemplary out-of-the-way docking station 164 to which the service robots 162 will automatically dock and recharge its batteries (if needed) during periods of inactivity. Preferably, each service robot 162 includes wireless communication components that facilitate data communications with one or more of the other wirelessly communicating smart-home sensors of FIG. 1 and/or with one or more other service robots 162 (e.g., using Wi-Fi, Zigbee, Z-Wave, 6LoWPAN, etc.), and one or more of the smart-home devices of FIG. 1 can be in communication with a remote server over the Internet. Alternatively or in conjunction therewith, each service robot 162 can be configured to communicate directly with a remote server by virtue of cellular telephone communications, satellite communications, 3G/4G network data communications, or other direct communication method.

Provided according to some embodiments are systems and methods relating to the integration of the service robot(s) 162 with home security sensors and related functionalities of the smart home system. The embodiments are particularly applicable and advantageous when applied for those service robots 162 that perform "away" functionalities or that otherwise are desirable to be active when the home is unoccupied (hereinafter "away-service robots"). Included in the embodiments are methods and systems for ensuring that home security systems, intrusion detection systems, and/or occupancy-sensitive environmental control systems (for example, occupancy-sensitive automated setback thermostats that enter into a lower-energy-using condition when the home is unoccupied) are not erroneously triggered by the away-service robots.

Provided according to one embodiment is a home automation and security system (e.g., as shown in FIG. 1) that is remotely monitored by a monitoring service by virtue of automated systems (e.g., cloud-based servers or other central servers, hereinafter "central server") that are in data communications with one or more network-connected elements of the home automation and security system. The away-service robots are configured to be in operative data communication with the central server, and are configured such that they remain in a non-away-service state (e.g., a dormant state at their docking station) unless permission is granted from the central server (e.g., by virtue of an "away-service-OK" message from the central server) to commence their away-service activities. An away-state determination made by the system, which can be arrived at (i) exclusively by local on-premises smart device(s) based on occupancy sensor data, (ii) exclusively by the central server based on received occupancy sensor data and/or based on received proximity-related information such as GPS coordinates from user smartphones or automobiles, or (iii) any combination of (i) and (ii)) can then trigger the granting of away-service permission to the away-service robots by the central server. During the course of the away-service robot activity, during which the away-service robots may continuously detect and send their in-home location coordinates to the central server, the central server can readily filter signals from the occupancy sensing devices to distinguish between the away-service robot activity versus any unexpected intrusion activity, thereby avoiding a false intrusion alarm condition while also ensuring that the home is secure. Alternatively or in conjunction therewith, the central server may provide filtering data (such as an expected occupancy-sensing profile triggered by the away-service robots) to the occupancy sensing nodes or associated processing nodes of the smart home, such that the filtering is performed at the local level. Although somewhat less secure, it would also be within the scope of the present teachings for the central server to temporarily disable the occupancy sensing equipment for the duration of the away-service robot activity.

According to another embodiment, functionality similar to that of the central server in the above example can be performed by an on-site computing device such as a dedicated server computer, a "master" home automation console or panel, or as an adjunct function of one or more of the smart-home devices of FIG. 1. In such embodiment, there would be no dependency on a remote service provider to provide the "away-service-OK" permission to the away-service robots and the false-alarm-avoidance filtering service or filter information for the sensed intrusion detection signals.

According to other embodiments, there are provided methods and systems for implementing away-service robot functionality while avoiding false home security alarms and false occupancy-sensitive environmental controls without the requirement of a single overall event orchestrator. For purposes of the simplicity in the present disclosure, the home security systems and/or occupancy-sensitive environmental controls that would be triggered by the motion, noise, vibrations, or other disturbances of the away-service robot activity are referenced simply as "activity sensing systems," and when so triggered will yield a "disturbance-detected" outcome representative of the false trigger (for example, an alarm message to a security service, or an "arrival" determination for an automated setback thermostat that causes the home to be heated or cooled to a more comfortable "occupied" setpoint temperature). According to one embodiment, the away-service robots are configured to emit a standard ultrasonic sound throughout the course of their away-service activity, the activity sensing systems are configured to detect that standard ultrasonic sound, and the activity sensing systems are further configured such that no disturbance-detected outcome will occur for as long as that standard ultrasonic sound is detected. For other embodiments, the away-service robots are configured to emit a standard notification signal throughout the course of their away-service activity, the activity sensing systems are configured to detect that standard notification signal, and the activity sensing systems are further configured such that no disturbance-detected outcome will occur for as long as that standard notification signal is detected, wherein the standard notification signal comprises one or more of: an optical notifying signal; an audible notifying signal; an infrared notifying signal; an infrasonic notifying signal; a wirelessly transmitted data notification signal (e.g., an IP broadcast, multicast, or unicast notification signal, or a notification message sent in an TCP/IP two-way communication session).

According to some embodiments, the notification signals sent by the away-service robots to the activity sensing systems are authenticated and encrypted such that the notifications cannot be learned and replicated by a potential burglar. Any of a variety of known encryption/authentication schemes can be used to ensure such data security including, but not limited to, methods involving third party data security services or certificate authorities. For some embodiments, a permission request-response model can be used, wherein any particular away-service robot requests permission from each activity sensing system in the home when it is ready to perform its away-service tasks, and does not initiate such activity until receiving a "yes" or "permission granted" message from each activity sensing system (or from a single activity sensing system serving as a "spokesman" for all of the activity sensing systems). One advantage of the described embodiments that do not require a central event orchestrator is that there can (optionally) be more of an arms-length relationship between the supplier(s) of the home security/environmental control equipment, on the one hand, and the supplier(s) of the away-service robot(s), on the other hand, as it is only required that there is the described standard one-way notification protocol or the described standard two-way request/permission protocol to be agreed upon by the respective suppliers.

According to still other embodiments, the activity sensing systems are configured to detect sounds, vibrations, RF emissions, or other detectable environmental signals or "signatures" that are intrinsically associated with the away-service activity of each away-service robot, and are further configured such that no disturbance-detected outcome will occur for as long as that particular detectable signal or environmental "signature" is detected. By way of example, a particular kind of vacuum-cleaning away-service robot may emit a specific sound or RF signature. For one embodiment, the away-service environmental signatures for each of a plurality of known away-service robots are stored in the memory of the activity sensing systems based on empirically collected data, the environmental signatures being supplied with the activity sensing systems and periodically updated by a remote update server. For another embodiment, the activity sensing systems can be placed into a "training mode" for the particular home in which they are installed, wherein they "listen" and "learn" the particular environmental signatures of the away-service robots for that home during that training session, and thereafter will suppress disturbance-detected outcomes for intervals in which those environmental signatures are heard.

For still another embodiment, which is particularly useful when the activity sensing system is associated with occupancy-sensitive environmental control equipment rather than a home security system, the activity sensing system is configured to automatically learn the environmental signatures for the away-service robots by virtue of automatically performing correlations over time between detected environmental signatures and detected occupancy activity. By way of example, for one embodiment an intelligent automated nonoccupancy-triggered setback thermostat such as the Nest Learning Thermostat can be configured to constantly monitor for audible and RF activity as well as to perform infrared-based occupancy detection. In particular view of the fact that the environmental signature of the away-service robot will remain relatively constant from event to event, and in view of the fact that the away-service events will likely either (a) themselves be triggered by some sort of nonoccupancy condition as measured by the away-service robots themselves, or (b) will occur at regular times of day, there will be patterns in the collected data by which the events themselves will become apparent and for which the environmental signatures can be readily learned. Generally speaking, for this automatic-learning embodiment in which the environmental signatures of the away-service robots are automatically learned without requiring user interaction, it is more preferable that a certain number of false triggers be tolerable over the course of the learning process. Accordingly, this automatic-learning embodiment is more preferable for application in occupancy-sensitive environmental control equipment (such as an automated setback thermostat) rather than home security systems for the reason that a few false occupancy determinations may cause a few instances of unnecessary heating or cooling, but will not otherwise have any serious, whereas false home security alarms may have more serious consequences.

According to embodiments, technologies including the sensors of the smart devices located in the mesh network of the smart-home environment in combination with rules-based inference engines or artificial intelligence provided at the central server or cloud-computing system 164 are used to provide a personal "smart alarm clock" for individual occupants of the home. For example, user-occupants can communicate with the central server or cloud-computing system 164 via their mobile devices 166 to access an interface for the smart alarm clock. There, occupants can turn on their "smart alarm clock" and input a wake time for the next day and/or for additional days. In some embodiments, the occupant may have the option of setting a specific wake time for each day of the week, as well as the option of setting some or all of the inputted wake times to "repeat". Artificial intelligence will be used to consider the occupant's response to these alarms when they go off and make inferences about the user's preferred sleep patterns over time.

According to embodiments, the smart device in the smart-home environment 100 that happens to be closest to the occupant when the occupant falls asleep will be the devices that transmits messages regarding when the occupant stopped moving, from which the central server or cloud-computing system 164 will make inferences about where and when the occupant prefers to sleep. This closest smart device will as be the device that sounds the alarm to wake the occupant. In this manner, the "smart alarm clock" will follow the occupant throughout the house, by tracking the individual occupants based on their "unique signature", which is determined based on data obtained from sensors located in the smart devices. For example, the sensors include ultrasonic sensors, passive IR sensors, and the like. The unique signature is based on a combination of walking gate, patterns of movement, voice, height, size, etc. It should be appreciated that facial recognition may also be used.

According to an embodiment, the wake times associated with the "smart alarm clock" are used to by the smart thermostat 102 to control the HVAC in an efficient manner so as to pre-heat or cool the house to the occupant's desired "sleeping" and "awake" temperature settings. The preferred settings can be learned over time, such as be observing which temperature the occupant sets the thermostat to before going to sleep and which temperature the occupant sets the thermostat to upon waking up.

According to an embodiment, a device is positioned proximate to the occupant's bed, such as on an adjacent nightstand, and collects data as the occupant sleeps using noise sensors, motion sensors (e.g., ultrasonic, IR, and optical), etc. Data may be obtained by the other smart devices in the room as well. Such data may include the occupant's breathing patterns, heart rate, movement, etc. Inferences are made based on this data in combination with data that indicates when the occupant actually wakes up. For example, if—on a regular basis—the occupant's heart rate, breathing, and moving all increase by 5% to 10%, twenty to thirty minutes before the occupant wakes up each morning, then predictions can be made regarding when the occupant is going to wake. Other devices in the home can use these predictions to provide other smart-home objectives, such as adjusting the smart thermostat 102 so as to pre-heat or cool the home to the occupant's desired setting before the occupant wakes up. Further, these predictions can be used to set the "smart alarm clock" for the occupant, to turn on lights, etc.

According to embodiments, technologies including the sensors of the smart devices location through the smart-home environment in combination with rules-based inference engines or artificial intelligence provided at the central server or cloud-computing system 164 are used to detect or monitor the progress of Alzheimer's Disease. For example, the unique signatures of the occupants are used to track the individual occupants' movement throughout the smart-home environment 100. This data can be aggregated and analyzed to identify patterns indicative of Alzheimer's. Oftentimes, individuals with Alzheimer's have distinctive patterns of migration in their homes. For example, a person will walk to the kitchen and stand there for a while, then to the living room and stand there for a while, and then back to the kitchen. This pattern will take about thirty minutes, and then the person will repeat the pattern. According to embodiments, the remote servers or cloud computing architectures 164 analyze the person's migration data collected by the mesh network of the smart-home environment to identify such patterns.

Figure 2:
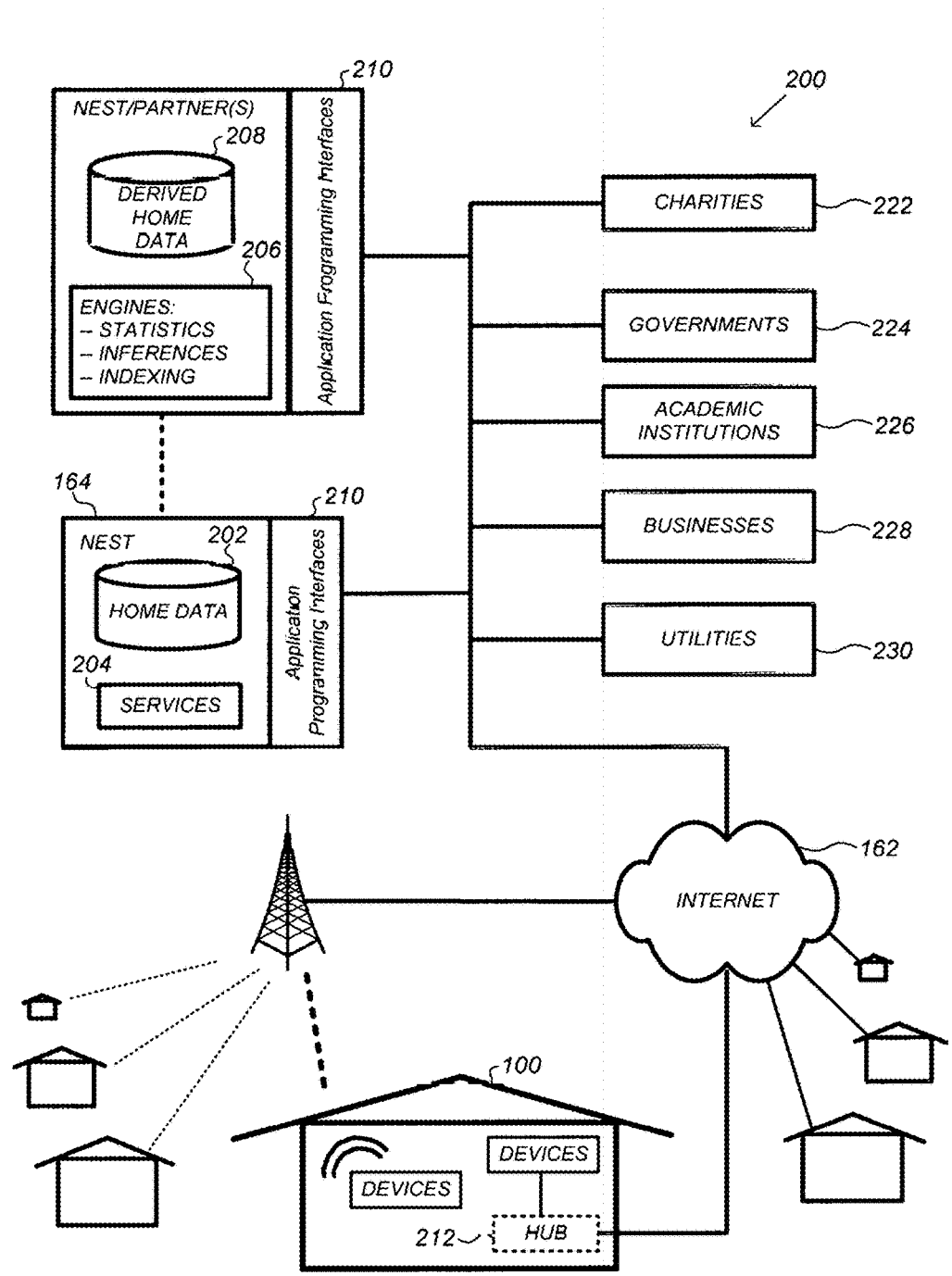
FIG. 2 illustrates a network-level view of an extensible devices and services platform with which the smart-home environment of FIG. 1 can be integrated, according to an embodiment.

FIG. 2 illustrates a network-level view of an extensible devices and services platform 200 with which a plurality of smart-home environments, such as the smart-home environment 100 of FIG. 1, can be integrated. The extensible devices and services platform 200 includes remote servers or cloud computing architectures 164. Each of the intelligent, network-connected devices 102, 104, 106, 108, 110, 112, 114, and 116 from FIG. 1 (identified simply as "smart devices" in FIGS. 2-3 herein) can communicate with the remote servers or cloud computing architectures 164. For example, a connection to the Internet 162 can be established either directly (for example, using 3G/4G connectivity to a wireless carrier), though a hubbed network 212 (which can be scheme ranging from a simple wireless router, for example, up to and including an intelligent, dedicated whole-home control node), or through any combination thereof.

Although in some examples provided herein, the devices and services platform 200 communicates with and collects data from the smart devices of smart-home environment 100 of FIG. 1, it should be appreciated that the devices and services platform 200 communicates with and collects data from a plurality of smart-home environments across the world. For example, the central server or cloud-computing system 164 can collect home data 202 from the devices of one or more smart-home environments, where the devices can routinely transmit home data or can transmit home data in specific instances (e.g., when a device queries the home data 202). Thus, the devices and services platform 200 routinely collects data from homes across the world. As described, the collected home data 202 includes, for example, power consumption data, occupancy data, HVAC settings and usage data, carbon monoxide levels data, carbon dioxide levels data, volatile organic compounds levels data, sleeping schedule data, cooking schedule data, inside and outside temperature humidity data, television viewership data, inside and outside noise level data, etc.

The central server or cloud-computing architecture 164 can further provide one or more services 204. The services 204 can include, e.g., software updates, customer support, sensor data collection/logging, remote access, remote or distributed control, or use suggestions (e.g., based on collected home data 202 to improve performance, reduce utility cost, etc.). Data associated with the services 204 can be stored at the central server or cloud-computing system 164 and the central server or the cloud-computing system 164 can retrieve and transmit the data at an appropriate time (e.g., at regular intervals, upon receiving request from a user, etc.).

As illustrated in FIG. 2, an embodiment of the extensible devices and services platform 200 includes a processing engine 206, which can be concentrated at a single server or distributed among several different computing entities without limitation. The processing engine 206 can include engines configured to receive data from devices of smart-home environments (e.g., via the Internet or a hubbed network), to index the data, to analyze the data and/or to generate statistics based on the analysis or as part of the analysis. The analyzed data can be stored as derived home data 208.

Results of the analysis or statistics can thereafter be transmitted back to the device that provided home data used to derive the results, to other devices, to a server providing a webpage to a user of the device, or to other non-device entities. For example, use statistics, use statistics relative to use of other devices, use patterns, and/or statistics summarizing sensor readings can be generated by the processing engine 206 and transmitted. The results or statistics can be provided via the Internet 162. In this manner, the processing engine 206 can be configured and programmed to derive a variety of useful information from the home data 202. A single server can include one or more engines.

The derived data can be highly beneficial at a variety of different granularities for a variety of useful purposes, ranging from explicit programmed control of the devices on a per-home, per-neighborhood, or per-region basis (for example, demand-response programs for electrical utilities), to the generation of inferential abstractions that can assist on a per-home basis (for example, an inference can be drawn that the homeowner has left for vacation and so security detection equipment can be put on heightened sensitivity), to the generation of statistics and associated inferential abstractions that can be used for government or charitable purposes. For example, processing engine 206 can generate statistics about device usage across a population of devices and send the statistics to device users, service providers or other entities (e.g., that have requested or may have provided monetary compensation for the statistics).

According to some embodiments, the home data 202, the derived home data 208, and/or another data can be used to create "automated neighborhood safety networks." For example, in the event the central server or cloud-computing architecture 164 receives data indicating that a particular home has been broken into, is experiencing a fire, or some other type of emergency event, an alarm is sent to other smart homes in the "neighborhood." In some instances, the central server or cloud-computing architecture 164 automatically identifies smart homes within a radius of the home experiencing the emergency and sends an alarm to the identified homes. In such instances, the other homes in the "neighborhood" do not have to sign up for or register to be a part of a safety network, but instead are notified of emergency based on their proximity to the location of the emergency. This creates robust and evolving neighborhood security watch networks, such that if one person's home is getting broken into, an alarm can be sent to nearby homes, such as by audio announcements via the smart devices located in those homes. It should be appreciated that this can be an opt-in service and that, in addition to or instead of the central server or cloud-computing architecture 164 selecting which homes to send alerts to, individuals can subscribe to participate in such networks and individuals can specify which homes they want to receive alerts from. This can include, for example, the homes of family members who live in different cities, such that individuals can receive alerts when their loved ones in other locations are experiencing an emergency.

According to some embodiments, sound, vibration, and/or motion sensing components of the smart devices are used to detect sound, vibration, and/or motion created by running water. Based on the detected sound, vibration, and/or motion, the central server or cloud-computing architecture 164 makes inferences about water usage in the home and provides related services. For example, the central server or cloud-computing architecture 164 can run programs/algorithms that recognize what water sounds like and when it is running in the home. According to one embodiment, to map the various water sources of the home, upon detecting running water, the central server or cloud-computing architecture 164 sends a message an occupant's mobile device asking if water is currently running or if water has been recently run in the home and, if so, which room and which water-consumption appliance (e.g., sink, shower, toilet, etc.) was the source of the water. This enables the central server or cloud-computing architecture 164 to determine the "signature" or "fingerprint" of each water source in the home. This is sometimes referred to herein as "audio fingerprinting water usage."

In one illustrative example, the central server or cloud-computing architecture 164 creates a signature for the toilet in the master bathroom, and whenever that toilet is flushed, the central server or cloud-computing architecture 164 will know that the water usage at that time is associated with that toilet. Thus, the central server or cloud-computing architecture 164 can track the water usage of that toilet as well as each water-consumption application in the home. This information can be correlated to water bills or smart water meters so as to provide users with a breakdown of their water usage.

According to some embodiments, sound, vibration, and/or motion sensing components of the smart devices are used to detect sound, vibration, and/or motion created by mice and other rodents as well as by termites, cockroaches, and other insects (collectively referred to as "pests"). Based on the detected sound, vibration, and/or motion, the central server or cloud-computing architecture 164 makes inferences about pest-detection in the home and provides related services. For example, the central server or cloud-computing architecture 164 can run programs/algorithms that recognize what certain pests sound like, how they move, and/or the vibration they create, individually and/or collectively. According to one embodiment, the central server or cloud-computing architecture 164 can determine the "signatures" of particular types of pests.

For example, in the event the central server or cloud-computing architecture 164 detects sounds that may be associated with pests, it notifies the occupants of such sounds and suggests hiring a pest control company. If it is confirmed that pests are indeed present, the occupants input to the central server or cloud-computing architecture 164 confirmation that its detection was correct, along with details regarding the identified pests, such as name, type, description, location, quantity, etc. This enables the central server or cloud-computing architecture 164 to "tune" itself for better detection and create "signatures" or "fingerprints" for specific types of pests. For example, the central server or cloud-computing architecture 164 can use the tuning as well as the signatures and fingerprints to detect pests in other homes, such as nearby homes that may be experiencing problems with the same pests. Further, for example, in the event that two or more homes in a "neighborhood" are experiencing problems with the same or similar types of pests, the central server or cloud-computing architecture 164 can make inferences that nearby homes may also have such problems or may be susceptible to having such problems, and it can send warning messages to those home to help facilitate early detection and prevention.

In some embodiments, to encourage innovation and research and to increase products and services available to users, the devices and services platform 200 exposes a range of application programming interfaces (APIs) 210 to third parties, such as charities 222, governmental entities 224 (e.g., the Food and Drug Administration or the Environmental Protection Agency), academic institutions 226 (e.g., university researchers), businesses 228 (e.g., providing device warranties or service to related equipment, targeting advertisements based on home data), utility companies 230, and other third parties. The APIs 210 are coupled to and permit third-party systems to communicate with the central server or the cloud-computing system 164, including the services 204, the processing engine 206, the home data 202, and the derived home data 208. For example, the APIs 210 allow applications executed by the third parties to initiate specific data processing tasks that are executed by the central server or the cloud-computing system 164, as well as to receive dynamic updates to the home data 202 and the derived home data 208.

For example, third parties can develop programs and/or applications, such as web or mobile apps, that integrate with the central server or the cloud-computing system 164 to provide services and information to users. Such programs and application may be, for example, designed to help users reduce energy consumption, to preemptively service faulty equipment, to prepare for high service demands, to track past service performance, etc., or to perform any of a variety of beneficial functions or tasks now known or hereinafter developed.

According to some embodiments, third-party applications make inferences from the home data 202 and the derived home data 208, such inferences may include when are occupants home, when are they sleeping, when are they cooking, when are they in the den watching television, when do they shower. The answers to these questions may help third-parties benefit consumers by providing them with interesting information, products and services as well as with providing them with targeted advertisements.

In one example, a shipping company creates an application that makes inferences regarding when people are at home. The application uses the inferences to schedule deliveries for times when people will most likely be at home. The application can also build delivery routes around these scheduled times. This reduces the number of instances where the shipping company has to make multiple attempts to deliver packages, and it reduces the number of time consumers have to pick up their packages from the shipping company.

Figure 3:
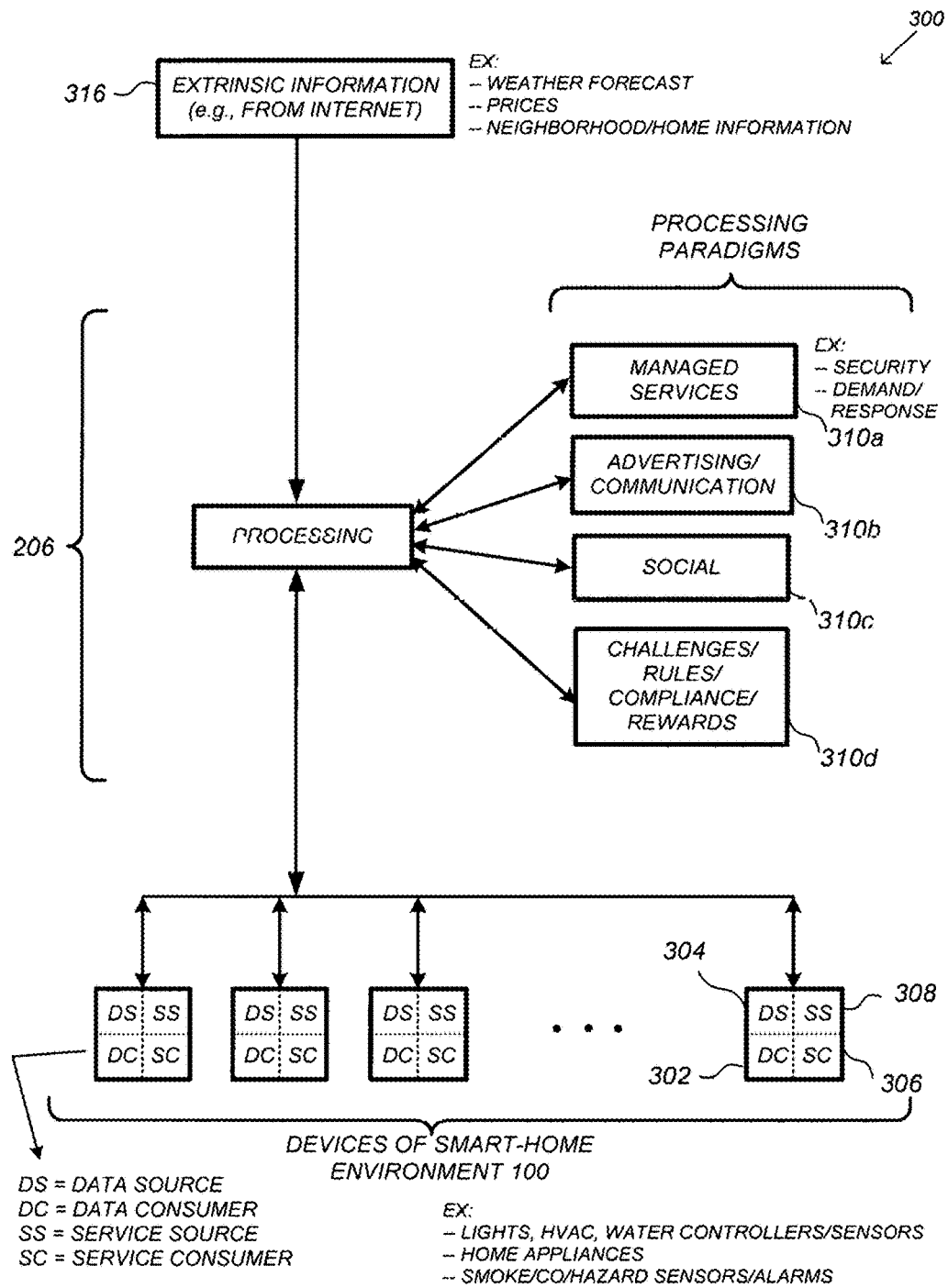
FIG. 3 illustrates an abstracted functional view of the extensible devices and services platform of FIG. 2, with reference to a processing engine as well as devices of the smart-home environment, according to an embodiment.

FIG. 3 illustrates an abstracted functional view of the extensible devices and services platform 200 of FIG. 2, with particular reference to the processing engine 206 as well as devices, such as those of the smart-home environment 100 of FIG. 1. Even though devices situated in smart-home environments will have an endless variety of different individual capabilities and limitations, they can all be thought of as sharing common characteristics in that each of them is a data consumer 302 (DC), a data source 304 (DS), a services consumer 306 (SC), and a services source 308 (SS). Advantageously, in addition to providing the essential control information needed for the devices to achieve their local and immediate objectives, the extensible devices and services platform 200 can also be configured to harness the large amount of data that is flowing out of these devices. In addition to enhancing or optimizing the actual operation of the devices themselves with respect to their immediate functions, the extensible devices and services platform 200 can be directed to "repurposing" that data in a variety of automated, extensible, flexible, and/or scalable ways to achieve a variety of useful objectives. These objectives may be predefined or adaptively identified based on, e.g., usage patterns, device efficiency, and/or user input (e.g., requesting specific functionality).

For example, FIG. 3 shows processing engine 206 as including a number of paradigms 310. Processing engine 206 can include a managed services paradigm 310*a* that monitors and manages primary or secondary device functions. The device functions can include ensuring proper operation of a device given user inputs, estimating that (e.g., and responding to) an intruder is or is attempting to be in a dwelling, detecting a failure of equipment coupled to the device (e.g., a light bulb having burned out), implementing or otherwise responding to energy demand response events, or alerting a user of a current or predicted future event or characteristic. Processing engine 206 can further include an advertising/communication paradigm 310*b* that estimates characteristics (e.g., demographic information), desires and/or products of interest of a user based on device usage. Services, promotions, products or upgrades can then be offered or automatically provided to the user. Processing engine 206 can further include a social paradigm 310*c* that uses information from a social network, provides information to a social network (for example, based on device usage), and/or processes data associated with user and/or device interactions with the social network platform. For example, a user's status as reported to their trusted contacts on the social network could be updated to indicate when they are home based on light detection, security system inactivation or device usage detectors. As another example, a user may be able to share device-usage statistics with other users. Yet another example, a user may share HVAC settings that result in low power bills and other users may download the HVAC settings to their smart thermostat 102 to reduce their power bills.

The processing engine 206 can include a challenges/rules/compliance/rewards paradigm 310*d* that informs a user of challenges, competitions, rules, compliance regulations and/or rewards and/or that uses operation data to determine whether a challenge has been met, a rule or regulation has been complied with and/or a reward has been earned. The challenges, rules or regulations can relate to efforts to conserve energy, to live safely (e.g., reducing exposure to toxins or carcinogens), to conserve money and/or equipment life, to improve health, etc. For example, one challenge may involves participates turning down their thermostat by one degree for one week. Those that successfully complete the challenge are rewarded, such as by coupons, virtual currency, status, etc. Regarding compliance, an example involves a rental-property owner making a rule that no renters are permitted to access certain owner's rooms. The devices in the room having occupancy sensors could send updates to the owner when the room is accessed.

The processing engine 206 can integrate or otherwise utilize extrinsic information 316 from extrinsic sources to improve the functioning of one or more processing paradigms. Extrinsic information 316 can be used to interpret data received from a device, to determine a characteristic of the environment near the device (e.g., outside a structure that the device is enclosed in), to determine services or products available to the user, to identify a social network or social-network information, to determine contact information of entities (e.g., public-service entities such as an emergency-response team, the police or a hospital) near the device, etc., to identify statistical or environmental conditions, trends or other information associated with a home or neighborhood, and so forth.

An extraordinary range and variety of benefits can be brought about by, and fit within the scope of, the described extensible devices and services platform 200, ranging from the ordinary to the profound. Thus, in one "ordinary" example, each bedroom of the smart-home environment 100 can be provided with a smart wall switch 108, a smart wall plug 110, and/or smart hazard detectors 104, all or some of which include an occupancy sensor, wherein the occupancy sensor is also capable of inferring (e.g., by virtue of motion detection, facial recognition, audible sound patterns, etc.) whether the occupant is asleep or awake. If a serious fire event is sensed, the remote security/monitoring service or fire department is advised of how many occupants there are in each bedroom, and whether those occupants are still asleep (or immobile) or whether they have properly evacuated the bedroom. While this is, of course, a very advantageous capability accommodated by the described extensible devices and services platform, there can be substantially more "profound" examples that can truly illustrate the potential of a larger "intelligence" that can be made available. By way of perhaps a more "profound" example, the same data bedroom occupancy data that is being used for fire safety can also be "repurposed" by the processing engine 206 in the context of a social paradigm of neighborhood child development and education. Thus, for example, the same bedroom occupancy and motion data discussed in the "ordinary" example can be collected and made available for processing (properly anonymized) in which the sleep patterns of schoolchildren in a particular ZIP code can be identified and tracked. Localized variations in the sleeping patterns of the schoolchildren may be identified and correlated, for example, to different nutrition programs in local schools.

Figure 4A:
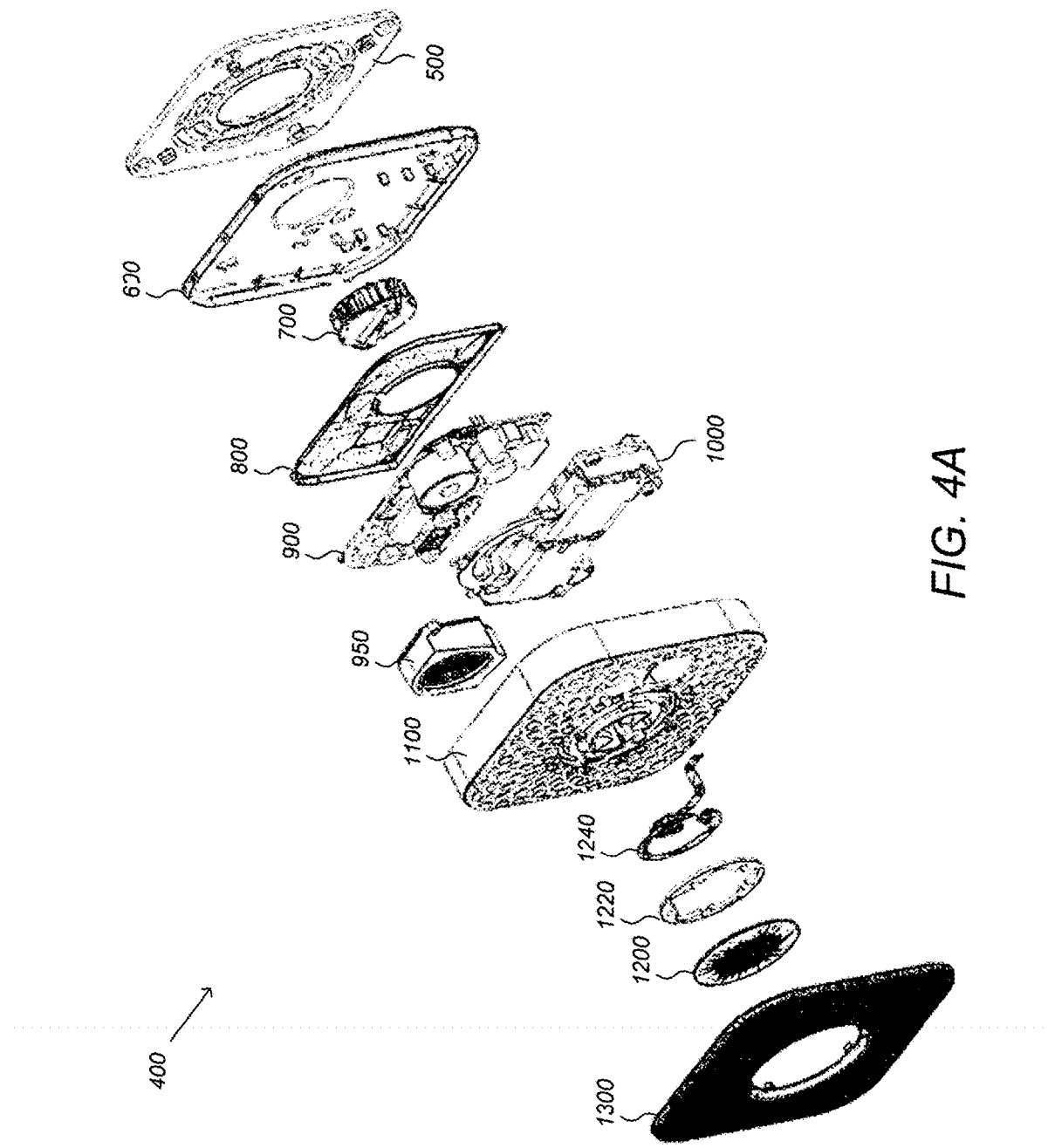
FIGS. 4A-F illustrate various perspective exploded and assembled views and a cross section view of an intelligent, multi-sensing, network-connected hazard detector, according to an embodiment.
Figure 4B:
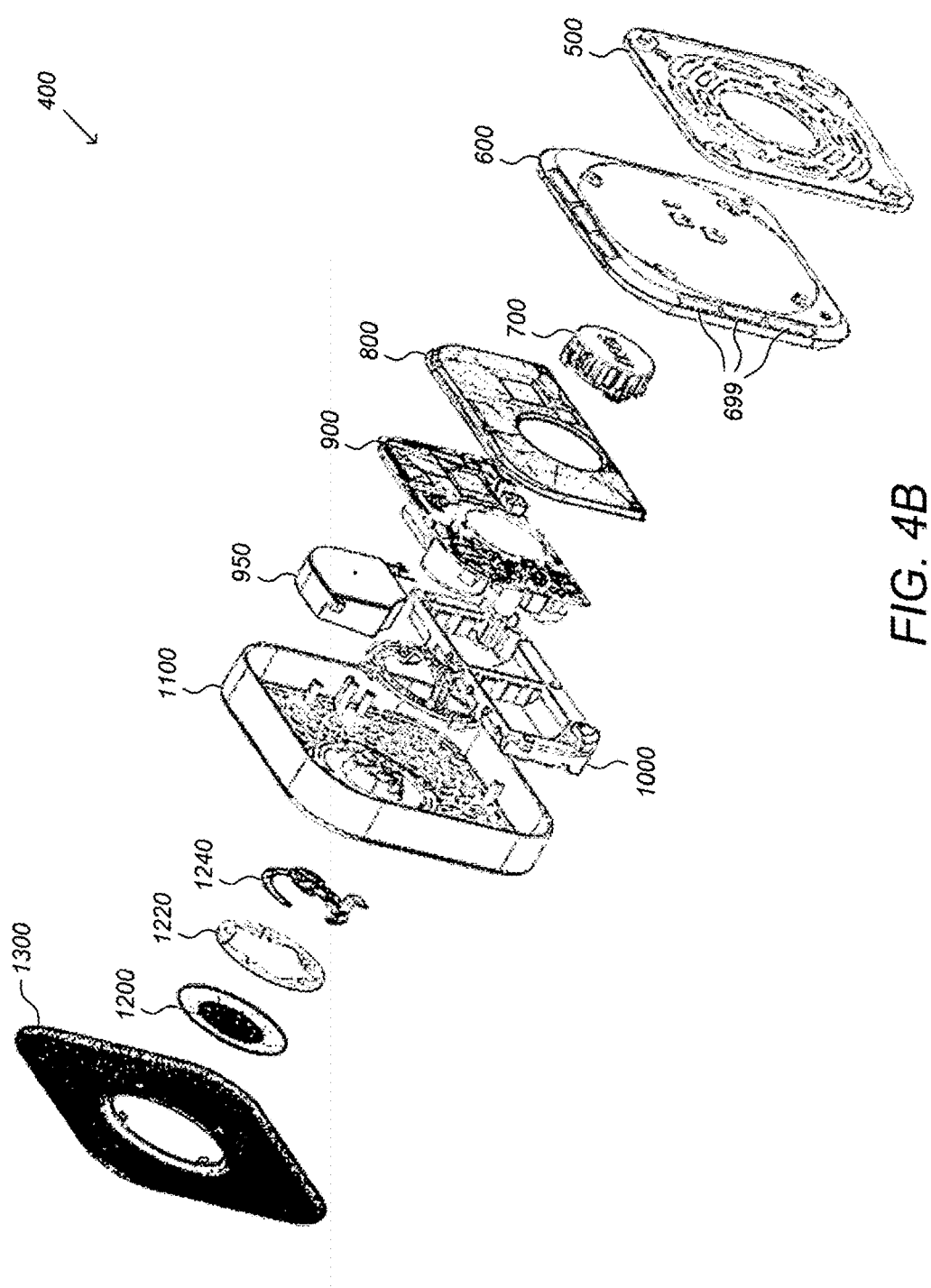
Figure 4C:
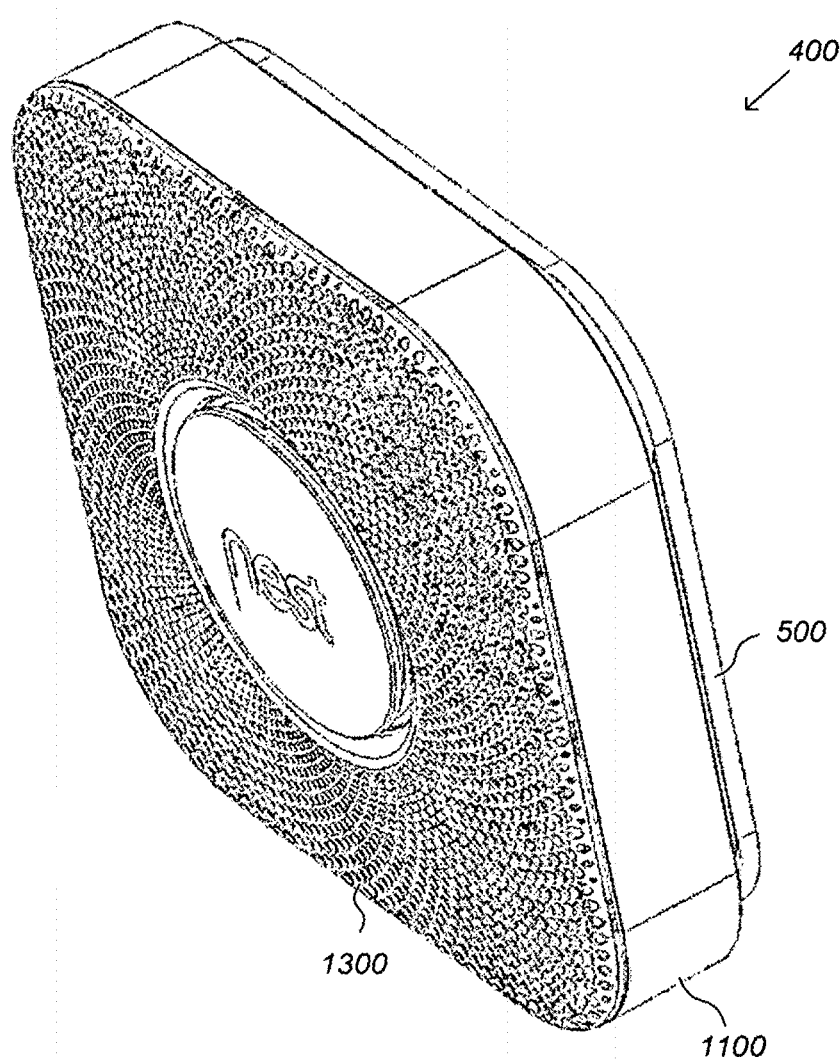
Figure 4D:
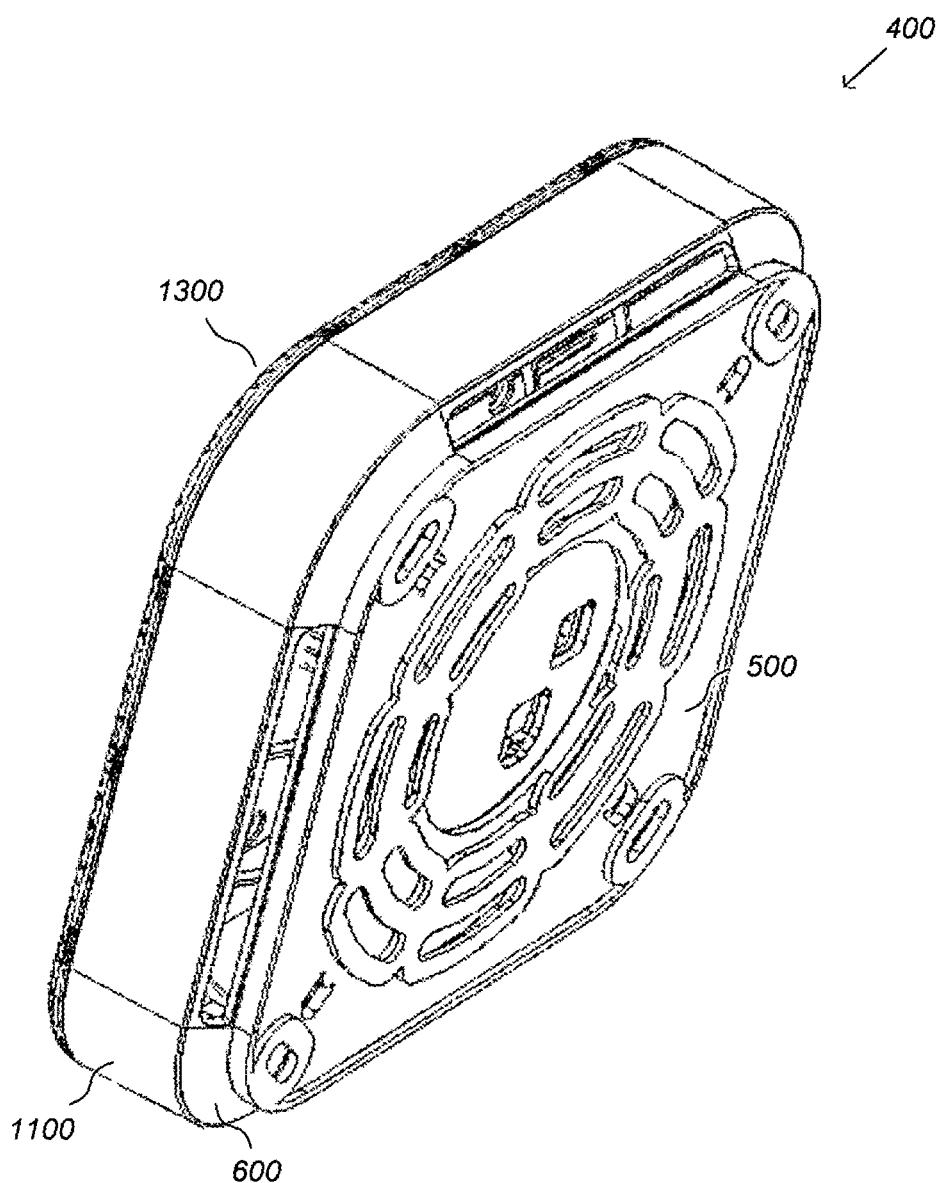
Figure 4E:
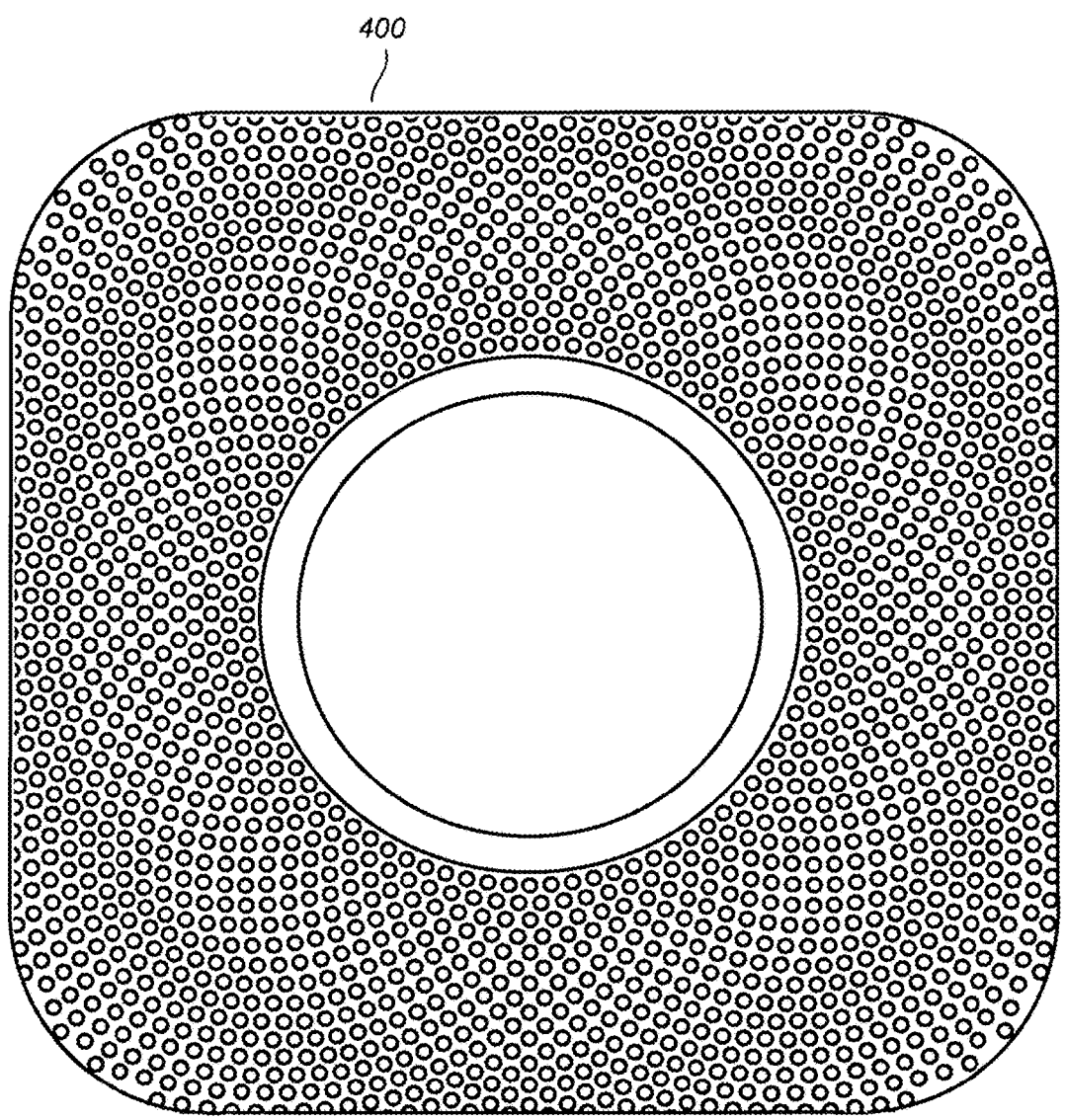
Figure 4F:
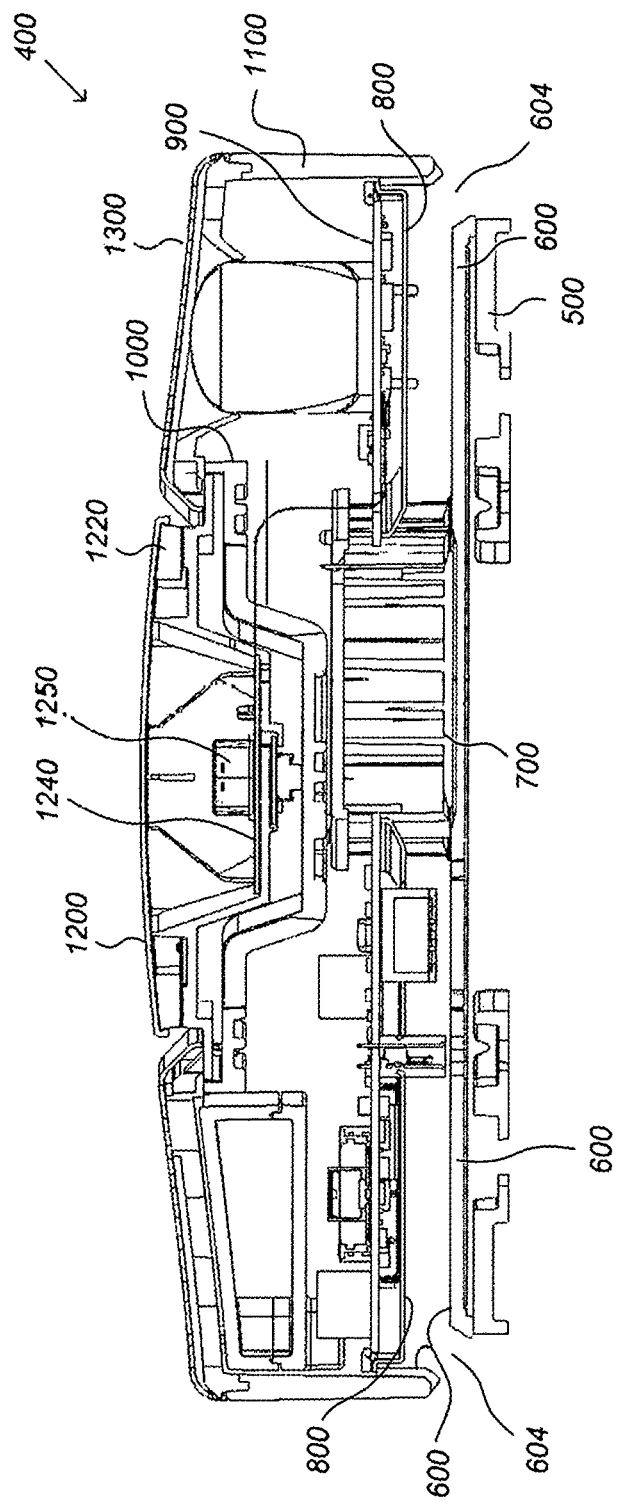

Referring now to FIGS. 4A-F, illustrated is a hazard detector 400 that may be advantageously incorporated into a smart home environment, for example, as one or more of the smart hazard detectors 104 of the smart home environment 100 of FIG. 1, supra. FIGS. 4A and 4B illustrate exploded front and rear perspective views, respectively, of the hazard detector 400, while FIGS. 4C and 4D illustrate front and rear perspective views, respectively, of the hazard detector 400 when assembled. FIG. 4E illustrates a front view of the hazard detector 400 and FIG. 4F illustrates a cross-sectional view of the hazard detector 400, showing the arrangement of several internal components. In one embodiment, hazard detector 400 is a smoke detector that is configured to detect the presence of smoke and sound an alarm to audibly warn an occupant or occupants of the home or structure of a potential fire or other danger. In other embodiments, hazard detector 400 may be a carbon monoxide detector, heat detector, and the like. In one embodiment, hazard detector 400 is a multi-sensing detector that includes a smoke detector, carbon monoxide detector, heat detector, motion detector, and the like. Many of the present teachings are particularly advantageous for embodiments in which the hazard detector 400 is a multi-sensing detector, particularly since combining the various sensing modes together into a single device can pose substantial challenges with respect to one or more of device compactness, component powering, and overall component governance and coordination. For convenience in describing the embodiments herein, the device 400 will be referred to hereinbelow as hazard detector 400, although it should be realized that hazard detector 400 may include various other devices and that the scope of the present teachings is not necessarily limited to hazard detectors in which smoke is required as one of the anomalies to be detected. Thus, for example, depending on the particular context as would be apparent to a person skilled in the art upon reading the instant disclosure, one or more of the advantageous features and embodiments described herein may be readily applicable to a multi-functional hazard sensor that detects carbon monoxide and motion only, or pollen and motion only, or noise pollution and pollen only, and so forth. Many other additional or alternative sensing functions can further be provided without departing from the scope of the present teachings including, but not limited to, temperature sensors, fire sensors, humidity sensors, barometric or other pressure sensors, ambient light sensors, other radiation sensors, accelerometers, vibration sensors, picture cameras, video cameras, and so forth. Nevertheless, the combining of smoke detection functionality with other sensing functions does bring about one or more particularly problematic issues that are addressed by one or more of the present teachings.

In one embodiment, hazard detector 400 is a roughly square or rectangular shaped object having a width of approximately 120 to 160 mm and a thickness of approximately 38 mm. Stated differently, hazard detector 400 is a multi-sensing unit having a fairly compact shape and size that may be easily attached to a wall or ceiling of a home or structure so as to be able, among other functionalities, to detect the presence of smoke and alert an occupant therein of the potential fire danger. As shown in FIGS. 4A and B, hazard detector 400 includes a mounting plate 500 that is removably coupled from a remainder of the unit, the mounting plate 500 being attachable to a wall or ceiling of the building or structure, the remainder of the hazard detector 400 then being secured by mateable mounting to the mounting plate 500. Hazard detector 400 also includes a back plate 600 and a front casing 1100 that may be coupled with or otherwise secured to back plate 600 to define a housing having an interior region within which components of the hazard detector 400 are contained. The back plate 600 is configured such that it can be mateably mounted to the mounting plate 500 by an installer/user to secure the hazard detector 400 in place. Vents 604 are formed in the back plate 600 at multiple locations around a periphery thereof to facilitate airflow from between the outside and inside of the hazard detector 400 housing. A circuit board 900 may be coupled with, attached to, or integral with the back plate 600. Various components may be mounted on circuit board

900. For example, a smoke chamber 700 may be coupled with or mounted on circuit board 900 and configured to detect the presence of smoke. In one embodiment, smoke chamber 700 may be mid-mounted relative to circuit board 900 so that air may flow into smoke chamber 700 from a position above circuit board 900 and below circuit board 900. A speaker 950 and alarm device (not numbered) may also be mounted on circuit board 900 to audibly warn an occupant of a potential fire danger when the presence of smoke is detected via smoke chamber 700, or when other hazardous condition(s) are detected. Other components, such as a motion sensor, carbon monoxide sensor, microprocessor(s), RF/wireless communication chips (e.g., Wi-Fi, 802.15.4), and the like may likewise be mounted on circuit board 900 as described herein.

In one embodiment, a protective plate 800 may be attached to or otherwise coupled with circuit board 900 to provide a visually pleasing appearance to the inner components of hazard detector 400 and/or to funnel or direct airflow to smoke chamber 700. For example, when a user views the internal components of hazard detector 400, such as through vents in back plate 600, protective plate 800 may provide the appearance of a relatively smooth surface and otherwise hide the components or circuitry of circuit board 900. Protective plate 800 may likewise function to direct a flow of air from the vents 604 of back plate 600 toward smoke chamber 700 so as to facilitate air flow into and out of smoke chamber 700.

Hazard detector 400 may also include a battery pack 1000 that is configured to provide power to the various components of hazard detector 400 when hazard detector 400 is not coupled with an external power source, such as a 120 V power source of the home or structure, and/or to serve as a backup power supply when hazard detector 400 is coupled with an external power source. In some embodiments, a cover plate 1300 may be coupled with the front casing 1100 to provide a visually pleasing appearance to hazard detector 400 and/or for other functional purposes. In a specific embodiment, cover plate 1300 may include a plurality of holes or openings that allow one or more sensors coupled with circuit board 900 to view or see through a surface of cover plate 1300 so as to sense objects external to hazard detector 400. The plurality of openings of cover plate 1300 may be arranged to provide a visually pleasing appearance when viewed by occupants of the home or structure. In one embodiment, the plurality of openings of cover plate 1300 may be arranged according to a repeating pattern, such as a sunflower-type pattern, a Fibonacci-type pattern, or other ordered or semi-ordered pattern. In one embodiment, the plurality of openings of cover plate 1300 may be arranged according to a random pattern or random-looking pattern.

A lens button 1200 may be coupled with or otherwise mounted to cover plate 1300. For some embodiments, the lens button 1200 is configured to serve a dual purpose as being a conventional user-pressable button while at the same time housing a component of a sensing system, serving as a component of a sensing system or otherwise facilitating the functionality of a sensing system. For some embodiments, lens button 1200 may be configured to allow one or more sensors to "view" or "sense" through the lens button 1200 for any of a variety of purposes. In one embodiment that is illustrated in FIG. 4F, a passive IR (PIR) sensor 1250 is positioned behind the lens button 1200 while an inner surface of the lens button 1200 is provided with an integral Fresnel lens or other radiation-directing component such that the PIR sensor 1250 can receive infrared energy passing through the surface of the lens button 1200, whereby a motion detection functionality is achieved to detect the presence of an occupant or occupants within the home or structure. Infrared absorption at specific wavelengths could also be measured to assess $CO_2$ and other gas concentrations in the room. This could be used as an air quality assessment or as a warning for hazardous conditions. In another embodiment an ambient light sensor could also be positioned behind the lens to obtain lighting conditions in the room. In another embodiment, an infrared camera could be positioned behind the lens to obtain a view of heat sources in the room. This could be used as an early warning device for dangerous levels of heat observed, as a way to determine the average temperature in the room, and/or as an occupancy indicator by detecting heat from people. In some embodiments, lens button 1200 may also function as a button that is pressable by a user to input various commands to hazard detector 400, such as to request a general status report, to instantiate a communication with a cloud server over a wireless link, to silence or "hush" an alarm or pre-alarm message that is triggered in response to a condition known to the occupant to be harmless or easily remedied, or for other purposes. Positioned distally behind lens button 1200 may be a light ring 1220 that is configured to receive light from a light generating component within the hazard detector 400, such as from one or more LEDs, and disperse the light therearound to provide a desired visual appearance, such as to provide a halo effect behind lens button 1200. Positioned distally behind light ring 1220 may be a flexible circuit board 1240 that includes one or more electrical components, such as a passive infrared sensor (hereinafter PIR sensor), LEDs, and the like. Flexible circuit board 1240 (hereinafter flex ring 1240) may be electrically coupled with circuit board 900 to communicate and/or receive instructions and/or signals from one or more microprocessors mounted on circuit board (not shown) during operation of hazard detector 400. Additional details of the components of hazard detector 400 are described in FIGS. 5A-13B.

FIGS. 4C and 4D illustrate hazard detector 400 with the various components assembled. Specifically, these figures show the mounting plate 500, front casing 1100, back plate 600, and cover plate 1300 in an assembled configuration with the various other components contained within an interior space of hazard detector 400. These figures also show the plurality of holes or openings of cover plate 1300 forming a visually pleasing design that is viewable by occupant of a room within which the hazard detector 400 is mounted. The lens button 1200 is shown attached to the hazard detector 400 so as to be centrally positioned with respect to cover plate 1300.

As briefly described above, light ring 1220 may be used to provide a halo appearance of light around and behind lens button 1200, being particularly useful as a method of communicating with a nearby user. For some embodiments, the light ring 1220 is configured to receive light from a plurality of light sources (e.g., a plurality of light pipes or light conduits, a plurality of strategically placed LEDs, or other methods of light transfer or creation) and to distribute that light in one of a spatially varying manner around the light ring (e.g., different light intensities and/or colors at different radial angles, ranges of radial angles, or radial zones around the center of the ring when viewed from the front), a time-varying manner, or temporospatially varying manner so as to provide certain predetermined visual effects that serve as certain predetermined communication signals for perception by nearby occupants. Although it is not outside the scope of the present teachings for the hazard detector 400 to be provided with a dot-matrix display or LCD screen (such as those provided on smartphones) for communicating status and other information to a user, the light ring 1220 and associated methodologies as described herein have been found to provide an informative, visually pleasing, and compelling user interface experience that promptly and effectively provides useful visual communication without requiring the close proximity and degree of eye focusing effort associated with reading a dot-matrix display screen.

For one embodiment representative of one such communication methodology, there are provided judiciously persistent, and yet at the same time pleasant, communications to nearby occupants regarding a status of the hazard detection unit 400 by the use of a modulated glow of halo light emitted by the light ring 1220. For some embodiments, the modulated glow of halo light is emitted responsive to one or more triggers indicating that it may be useful to communicate status information to a nearby occupant, wherein the time pattern, spatial pattern, color, or other visual characteristic of the modulation is representative or indicative of a particular condition to be communicated to the occupant and/or recommended action to be taken by the occupant. One example of a triggering event may be the shutting off of a room light as detected by an ambient light sensor of the hazard detection unit 400. Examples of the type of modulated glow can include a fade-in uniform glow of a pleasant color or non-alarming color, such as green, to communicate a reassurance that the status of the hazard detector 400 is "everything is okay." The fade-in glow can comprise, for example, a one-second ramp-up of light intensity from dark to bright, followed by a one-second glow at full brightness, followed by a one-second fade-out from bright to dark. Advantageously, the temporal variation enhances the ability of the user to notice the advisory light even when they were not directly looking at it, while at the same time the color and fade-in nature of the glow maintains a degree of pleasantness. Advantageously, at the same time, battery life of battery-powered versions of the hazard detection unit 400 is preserved by virtue of the temporary nature of the modulated glow. Another type of modulated glow, which can optionally be combined with a fade-in characteristic, is a rotating halo-sweep effect, which emulates the visual effect of one or more point light sources traveling around a perimeter of the circle, each of them leaving a comet-like tail of light in its wake.

Another example of a type of modulated glow can be a fade-in glow of a somewhat more concerning color, such as yellow, to suggest that the user may want to investigate one or more anomalous, but not necessarily severe, conditions that have been determined to be present. An example of such a condition could be that a charge level of a battery on-board the hazard detector 400 is starting to get low, although not low enough for mandatory replacement, and should be replaced in the reasonably not-too-distant future. It will be appreciated by one skilled in the art that this type of advance notification for a low-battery condition in a hazard detector will promote a relatively pleasant user experience in comparison to that provided by many conventional smoke and/or CO detectors currently on the market, which are configured to act only when the battery becomes low enough to require mandatory replacement in the form of intermittently emitted short loud chirps, chirps which can often awake sleeping occupants, whose frustration is then often exacerbated by a need to empirically localize which of multiple installed units is actually emitting the chirp, and whose safety can then often be compromised by a sleepy decision to simply remove the battery "temporarily" and replace it during waking hours. Notably, although the hazard detection unit 400 is preferably configured to indeed emit such short loud chirps when the battery does indeed require mandatory replacement for purposes of maintaining consistency with governmental or industry regulations, such unpleasantness is often advantageously avoided by virtue of the above-described advance yellow modulated-glow notifications which lead to battery replacement prior to reaching the low mandatory-replacement levels. It is to be appreciated that although "yellow" is used herein to identify a "concerning" color, it is representative of any of a variety of "concerning" colors or color combinations that can be used according to the present teachings to indicate an anomalous condition.

According to some embodiments, the triggered yellow modulated glow provided by the light ring can be indicative of the presence of one or more of a plurality of different potential anomalous conditions, and the yellow modulated glow serves as an invitation to the user to make an inquiry into the particular nature of the detected anomalous condition(s). For some embodiments, the yellow modulated glow is stored at a cloud server of a web-based service associated with the smart, network-connected hazard detector, to which the user can log on using their personal computer, tablet, or smartphone to investigate the particular status of the unit. For purposes of battery conservation in battery-only units that connect to the cloud service by Wi-Fi connection through a conventional home router, the hazard detection unit 400 is configured to upload status information to the cloud service by Wi-Fi connection only upon the occurrence of particular events (such as the user pressing the lens button 1200, alarm or pre-alarm conditions, the detection of a user waving their hand at the unit as detected by onboard PIR/ultrasonic sensors, etc.), or if no such events have occurred recently, then at least once every 12 or 24 hours. Alternatively or in conjunction with user inquiry to the cloud server, the nature of the particular anomalous condition indicated by the yellow modulated glow can be communicated directly by the hazard detector 400 using a real-time audio (or audiovisual) response to a user inquiry made directly thereto upon perceiving the yellow modulated glow. For some embodiments, the real-time audio response can be made to the user using a computer-synthesized or pre-recorded voice emitted using an onboard speaker (e.g., "The yellow light was shown because my battery is starting to get low.") For some embodiments, the user inquiry to evince this response upon seeing the yellow modulated glow can be made by virtue of pressing the lens button 1200. For some embodiments, the user inquiry is established by virtue of a back-and-forth wave gesture made by the user's hand while the user is facing the unit, the unit having one or more sensors capable of detecting the wave gesture motion as described in the commonly assigned U.S. Ser. No. 61/847,906, supra. For some embodiments, as discussed in U.S. Ser. No. 61/847,906, supra, a combination of PIR and ultrasonic sensor information is used to detect a user wave gesture motion without requiring optical sensing/optical recognition techniques, thereby providing an advantage of enabling the wave gesture recognition while also keeping electrical power requirements suitably low to preserve battery life in battery-only units. However, it is to be appreciated that the scope of the present teachings is not so limited, and that other inquiry methods and detection techniques can be used without departing from the scope of the present teachings including, but not limited to, optical recognition techniques (i.e., visually "seeing" the user waving their hand), audio or speech recognition techniques (e.g., the user clapping their hands twice or saying "please explain the yellow light" or similar such inquiries), ambient light sensing techniques (e.g., the user flipping the room light switch on and off three or more times), or other methods.

In one exemplary scenario provided according to one or more embodiments that shows the usefulness and appeal of such features, the hazard detection unit 400 may be installed in the bedroom of a child who is being tucked in by her mother for the night. After tucking in the child, the mother turns the light out as she walks toward the door. Just then, the hazard detection unit 400 senses the turning off of the light by virtue of the on-board ambient light sensor, and then proceeds to show a fade-in uniform glow for a short time (e.g., two to three seconds) of a pleasing green color using the light ring 1220. The mother sees the light out of the corner of her eye as she walks out the door and is pleasantly reassured that the hazard detection unit 400, which will be in her child's midst throughout the night, is signaling that no anomalies are detected, and she is pleased that she installed the hazard detection unit 400 in furtherance of keeping her child and family safe. In an alternative scenario in which the yellow modulated glow is presented and perceived by the mother, the mother hesitates, walks toward the unit, and waves her hand in a wave gesture. As she is waving or very shortly thereafter, she hears the unit say "My battery is starting to get low, please replace in the near future." While knowing she should take some action reasonable soon to have the battery replaced, she is pleasantly reassured in knowing her family will not be woken up by irritating chirps in the middle of the night, and that there are otherwise no anomalies reported other than the battery issue by the unit. As an alternative to hand wave gesturing to the unit, the mother can walk out and close the child's bedroom door, and then access her web site account corresponding to the unit using her computer, tablet, or smartphone to see the reason for the yellow modulated glow. Providing a smart, network-connected household hazard detector that uses a modulated light glow such as can be provided by a halo light having temporal, spatial, or temporospatial modulation to facilitate seamless, easily-perceived yet information-rich communications with users has been found to substantially increase user appeal, which can advantageously increase the ubiquity of smart, network-connected household hazard detectors, which can in turn prove to be a boon for household safety and public safety.

According to some embodiments, a judiciously invoked lighting feature, which is termed herein a pathlighting feature, is also provided by virtue of the light ring 1220 (or other light-emitting element mounted upon or associated with the hazard detector 400) in conjunction with one or more ambient light sensors mounted on or associated with the hazard detector 400. According to some embodiments, the hazard detection unit is configured to emit a predetermined amount of illumination at a predetermined power level upon the detection of motion by the one or more motion sensors of the hazard detector. According to some embodiments, the hazard detector is configured to detect the presence of one or more conditions indicating that there is an occupant likely requiring additional ambient light in moving from one location to another, and to actively emit an amount of light sufficient to facilitate that occupant movement. Preferably, a determination of conditions sufficient to trigger an emitting of supplemental light takes into account a combination of (i) at least one user-induced sensor reading by the hazard detector, such as the sensing of user movement in the room or hallway (such as by a PIR or active motion detector, low-light-sensitive video sensor, heat sensor, etc.) and/or the sensing of an audible user request (e.g., a voice command from the user saying "light my path" or "pathlight"), (ii) at least one current ambient light level reading, and (iii) at least one historical ambient light level reading. Thus, for example, if the user is not making motions consistent with a significant change of location in the room or hallway, or if the room is not dark enough to require additional ambient lighting in view of the historical lighting pattern of the room, then no light is output from the hazard detector.

For some embodiments that are particularly advantageous for battery-only hazard detector units in preserving power, the intensity of the light emitted is adaptive, such that the particular amount of marginal light supplied is not substantially greater than the particular amount of marginal light needed by the human occupant to achieve the goal of moving from one place to the other in the room or hallway in a reasonably safe manner. Preferably, the adaptation response of the human visual system is taken into account in determining both the need for additional illumination and the amount of additional illumination provided. Advantageously, in addition to preserving electrical power for embodiments in which the hazard detector is a battery-only unit, the limiting of the light intensity may also lead to a more optically comfortable experience for the moving occupant.

Thus, in one exemplary scenario illustrating the features and advantages of one or more described embodiments, a student who has been studying under relatively bright ambient lighting for several hours decides to pull down all window shades, turn off the light, and crawl into bed. However, 20 seconds after lying down, the student realizes they have not brushed their teeth and stands up at the side of the bed to walk toward the door. Upon detecting the student standing up at the bed, the hazard detector emits light at a first level as the student walks toward and out the door to the bathroom. When implemented according to some embodiments, that first light level is substantially brighter than a second level of light that would be provided by the hazard detector in an alternative scenario in which the student had performed all those same actions, but had instead been studying under relatively dim light for those several hours. This is because the student's eyes would not need as much light since they had already been adjusted to a low light level just before turning out the light 20 seconds earlier. Furthermore, that first light level is substantially brighter than a third level of light that would be provided by the hazard detector in a different alternative scenario in which the student had performed all those same actions, but had instead has been lying in bed for 20 minutes before realizing they had not brushed their teeth. The third level of light can be substantially dimmer than the first level of light, because the human visual response of the student has had 20 minutes to adapt to the darkness, such that relatively little light is needed for safe passage to the door of the room, and indeed such that the student may even have experienced some degree of discomfort (squinting) if the relatively bright first amount of light had been provided.

Further embodiments describing features or characteristics that may accompany or be used alternatively to the above-described status communication methods and/or pathlighting methods are presented here by way of example and not by way of limitation. For some embodiments, the wave gesture recognition feature associated with the above status communications method can have a default "enabled" status, but can be disabled by the user by logging on to their account at the web-based cloud service provider and accessing a corresponding feature enable/disable menu. For other embodiments, the wave gesture recognition feature can have a default "disabled" status, but can be enabled by the user by logging on to their online account. For some embodiments, the described automated pathlighting feature can have a default "disabled" status, but can be enabled by the user by logging on to their online account. For other embodiments, the pathlighting feature can have a default "enabled" status, but can be enabled by the user by logging on to their online account.

For some embodiments, a variety of different triggers by which the hazard detector may be caused to communicate status information to users can be used including, but not limited to: upon sensing a first entry of an occupant into a space, such as by motion detection, after predetermined period of vacancy in that space; upon sensing a substantial vibration, such as by an onboard accelerometer, that may be indicative of a nearby door being closed or opened; upon sensing an audio sound similar to that of a door being opened or closed; upon a user request for status actuated by pressing a button on the device; upon a user voice request for status information (e.g., "Present device status"); after sensing an entrance of a new occupant in an already-occupied room, such as by automated facial recognition, or by RFID, NFC, or other electromagnetic signature associated with the new entrant's smartphone or other wearable device; upon sensing a substantial pressure change that may be indicative of a window or door being opened or closed; upon a sensed or communicated "scene change" to a room in the form of modified lighting, modified window shade positioning, modified entertainment system settings, or other "scene change"; upon detecting the presence of more occupants than a predetermined number of occupants or more than a learned "normal" number of occupants; or more generally, upon the happening of one or more sensed events and/or received communications by which, when assessed in view of one or more predetermined or learned parameters, a conclusion or inference can be made that it would be useful to communicate a device status to an occupant. For some embodiments, a variety of different triggers by which the hazard detector may be caused to light a path for an occupant, or otherwise increase an ambient light level in a space, can be used including, but not limited to: receiving a voice command from the occupant; sensing that a bright television in a relatively dim room has been turned off; sensing general or specified audio activities during sleeping hours after a substantial period of quiet (e.g., the creaking of a bedframe or floorboards); or more generally upon the happening of one or more sensed events and/or received communications by which, when assessed in view of current and historical ambient light measurements and one or more other predetermined or learned parameters, a conclusion or inference can be made that it would be useful to increase an ambient light level in a space for the benefit of an occupant.

Still further embodiments describing features or characteristics that may accompany or be used alternatively to the above-described status communication methods and/or pathlighting methods are presented here by way of example and not by way of limitation. While the use of a halo light represents one particularly effective physical configuration for emitting modulated light patterns recognizable from multiple distances, other configurations such as multiple concentric haloes, multiple individual lights of varying shapes, a single individual point light judiciously time-modulated, or multiple individual point lights arranged in regularly or irregular patterns can be used. While communicating a status of the hazard detector itself based on information represents one particularly advantageous set of information to communicate, any of a variety of other statuses associated with the household or family can be communicated by the above-described status communication methods including, but not limited to: a general or specific security status of the home (showing, for example, the green modulated glow to communicate an "all is well" status, a yellow modulated glow if the garage door is still open at a late evening hour); a general or specific network status of the home network (e.g., the router/modem has lost broadband communication with the ISP); a general or specific household operational status (e.g., a yellow modulated glow if the sprinkler system malfunctioned last night); a general or specific household efficiency status (e.g., the gas pool heater has exceeded a predetermined cost threshold for the month); a general or specific household obligational status (e.g., a yellow modulated glow if a past-due e-mail from a utility company, paid content provider, or communications company has been received); or any of a variety of other predetermined or learned household-related or family-related statuses for which a trigger, conclusion, or inference can be established that it would be useful to communicate such household-related or family-related status to a user.

According to some embodiments in which an audible voice or audible sound is used to communicate with the user, the hazard detection unit is configured to automatically vary the loudness of the speaker according to a static and/or dynamic audio profile of the room or hallway in which it is installed. Thus, for example, if the communication is to be made during a time of high ambient noise (e.g., the kids are playing loudly or visitors are shouting at the football game on television), then the loudness of the speaker is increased, whereas if it is currently quiet and there has been an extended period of quiet, the loudness of the speaker can be decreased.

According to some embodiments, the hazard detector 400 is configured to further provide a pre-alarming capability, which can also be termed a "heads-up" capability, to provide a warning to the user that a pre-hazardous condition has been detected in which there are elevated readings corresponding to the type of hazard being detected, but those readings do not yet rise to levels corresponding to an actual alarm condition. Generally, a pre-alarm or heads-up condition is one that merits more immediacy of concern than those underlying the above-described persistent-yet-pleasant modulated glow level of communication. Whereas the above-described persistent-yet-pleasant modulated-glow level of communication is not accompanied by an audible advisory unless the user accepts the initial "invitation" of that light pattern (e.g., by gesture wave or pressing the device button), a pre-alarm or heads-up condition is indeed accompanied by an immediate audible message. Exemplary pre-alarm or heads-up conditions can be, for example, readings for carbon monoxide that are elevated but not high enough to warrant the sounding of a standard carbon monoxide alarm, or readings for smoke levels that are elevated but not high enough to warrant a sounding of a standard smoke alarm. Exemplary algorithms for detecting these types of pre-alarm conditions an corresponding alarm conditions are described in the commonly assigned U.S. Ser. No. 61/847,937, supra.

When a heads-up condition is detected, the hazard detector is configured to sound an audible, but not ear-piercing, "pre-alarm" or "heads-up" message that audibly informs the user of the pre-alarm condition. For some embodiments, a modulated light glow of a concerning color and/or spatiotemporal pattern accompanies the pre-alarm message. One example of such an audible message that may be provided in the context of a pre-alarm level of smoke for a hazard detector installed in a bedroom may comprise a bell or bell-like sound, followed by an voice message, "Heads Up. There is smoke in the bedroom." Preferably, once the pre-alarm condition has gone away (for example, the user has gone to the bedroom and snuffed out a cigarette that was in the ash tray, and that action was successful in clearing up the smoke), the hazard detector then also audibly advises that the condition has cleared (e.g., "Smoke has cleared in the bedroom.") In the event the pre-alarm condition worsens into an actual alarm condition, then the ear-piercing alarm sounds, preferably accompanied by an emergency-indicating halo glow (e.g., red or flashing red), and further accompanied, during any regulation-required or regulated-permitted silence intervals between alarming, by a voice alarm (e.g., "EMERGENCY. THERE IS SMOKE IN THE BEDROOM") or ("EMERGENCY, SMOKE IN THE BEDROOM, GET OUT NOW.")

While pre-alarming based on an environmental hazard levels such as smoke or carbon monoxide represents one particularly advantageous use of a heads-up feature, a variety of other heads-up alarms based on other potential threats, such as security or structural integrity threats, can be communicated by the heads-up methodology without departing from the scope of the present teachings. As discussed above, the level of threat for providing a heads-up message should generally be of more immediacy than for a "yellow" level persistent-yet-pleasant modulated-glow communication, but less of a threat than that for which an ear-piercing alarm if warranted. Thus, by way of example, whereas "My battery is starting to get low" may be associated with a yellow modulated glow persistent-yet-pleasant communication followed by an inquiring gesture, a heads-up or pre-alarm event associated with security or structural integrity may be "Heads up, water has been detected on the basement floor," and is provided immediately without requiring the user to "ask" by virtue of a button press or wave gesture, although the heads-up alarm may indeed be silenced/hushed by a button press or hand wave gesture. Further examples of potential security or structural integrity threats that may warrant a heads-up message include, by way of example, that it is past 7 PM and not all of the kids are home yet, that a large parcel has been left on your doorstep, that a current network intrusion has just been detected at the family gaming computer, or any of a variety of other predetermined potential security or structural integrity threats for which a trigger, conclusion, or inference can be established that an associated pre-alarm or heads-up message should be immediately provided.

FIG. 4F illustrates a cross-sectional view of the assembled hazard detector 400.

Specifically FIG. 4F illustrates the back plate 600 coupled to the mounting plate 500, which may be attached to a wall or ceiling of a home or structure. The front casing 1100 is attached to the back plate 600 to define the housing having an interior region within which components of the hazard detector 400 are contained. Cover plate 1300 is coupled with front casing 1100 to provide a visually appealing outer surface as previously described. Lens button 1200 is coupled with cover plate 1300 and positioned centrally relative thereto. Positioned under lens button 1200 is light ring 1220 and flex ring 1240. Circuit board 900 is coupled with back plate 600 and includes various components (e.g. one or more microprocessors, memory modules, wireless communication modules, power adapting modules, driver circuitry for a shrieking alarm device, an audio speaker, a CO detector, a heat sensor, a speaker, etc.) mounted thereon to be used for various purposes.

FIG. 4F also illustrates that the smoke chamber 700 is mid-mounted within the interior of the housing of hazard detector 400. As shown, mid-mounting is characterized in that the smoke chamber 700 extends through a hole formed in the circuit board 900 such that a top surface of the smoke chamber 700 is positioned above a top surface of the circuit board 900 and a bottom surface of the smoke chamber 700 is positioned below a bottom surface of the circuit board 900. In this configuration, an interior chamber of smoke chamber 700 is accessible to smoke from both the top surface of the circuit board 900 and the bottom surface of the circuit board 900. Stated differently, smoke chamber 700 is mounted on circuit board 900 such that air is flowable into an interior region of smoke chamber 700 from one or both sides of the circuit board 900 and flowable out of the interior region of smoke chamber 700 from an opposite side of the circuit board 900. In this manner, the flow of air and smoke in an essentially or substantially unimpeded manner into and out of the smoke chamber 700 is promoted.

In some embodiments, smoke chamber 700 may also be mid-mounted with respect to protective plate 800. In other words, smoke chamber 700 may extend through a hole formed in protective plate 800 such that a top surface of smoke chamber 700 is positioned above a top surface of protective plate 800 and a bottom surface of smoke chamber 700 is positioned below a bottom surface of protective plate 800. In this configuration, smoke chamber 700 is mid-mounted with respect to both the protective plate 800 and circuit board 900 so that air and smoke is flowable into smoke chamber 700 from both a top surface and a bottom surface of circuit board 900 and protective plate 800. Further, in this configuration protective plate 800 functions to guide or direct airflow toward smoke chamber 700. For example, the edges of protective plate 800 are positioned near the edge of hazard detector 400 and protective plate 800 provides a relatively smooth surface that directs air flow from near the edges of hazard detector 400 toward the smoke chamber 700, which is positioned substantially centrally within hazard detector 400. The substantially smooth or flat surface of protective plate 800 prevents air and smoke from contacting the components of circuit board 900 and thereby helps facilitate airflow into and out of smoke chamber 700.

The mid-mounting of smoke chamber 700 also helps prevent pressure buildup within hazard detector 400 since air and smoke is flowable along or adjacent one side of the circuit board 900 to smoke chamber 700, through smoke chamber 700, and flowable along or adjacent an opposite side of circuit board 900. For example, in some conventional hazard detectors having a smoke chamber mounted on one side of a circuit board, air pressure may increase near the smoke chamber since air and smoke is only able to flow to the smoke chamber along one side of the circuit board, but not an opposite side of the circuit board. Stated differently, the air and smoke may accumulate near the smoke chamber causing an increase in air pressure near the smoke chamber since the air is funneled towards the smoke chamber along a single surface of the circuit board, but not able to exit along any other route other than the single surface of the circuit board. The mid-mounting of smoke chamber 700 described herein allows air and smoke to be funneled toward the smoke chamber 700 along one side or surface of circuit board 900, pass through the smoke chamber 700, and exit along an opposite side or surface of circuit board 900.

Mid-mounting of smoke chamber 700 also decreases an orientational dependence of the hazard detector 400 in detecting smoke within the home or structure. For example, when testing smoke detectors, the smoke detectors are typically rotated to find the least sensitive smoke detection direction. The sensitivity of the smoke detectors are typically tested with the smoke detectors oriented in the least sensitive direction. Mid-mounting of the smoke chamber 700 within hazard detector 400 substantially reduces or eliminates orientation dependence in relation to the detection functionality. Stated differently, mid-mounting of the smoke chamber 700 essentially allows the hazard detector 400 to exhibit uniform smoke detection ability regardless of the orientation.

Mid-mounting of smoke chamber 700 may also facilitate in cooling the various components mounted on or otherwise coupled with circuit board 900. For example, airflow within hazard detector 400 may be increased due to the ability of air to flow in, around, and through smoke chamber 700. Airflow relative to one or more heat producing electrical components mounted on the circuit board, such as one or more microprocessors, may be increased because air does not accumulate atop the circuit board 900 or otherwise within hazard detector 400 due to the presence of the mid-mounted smoke chamber 700 and/or other mid-mounted components. The increased flow of air around the one or more heat producing electrical components may provide a degree of cooling for such components. In one embodiment a first microprocessor (not shown) may be coupled on a first side of circuit board 900 while a second microprocessor (not shown) is coupled on a second side of circuit board 900 opposite the first microprocessor. Air may flow between the first and second sides of circuit board 900 as described herein to provide a degree of cooling for the first microprocessor and/or second microprocessor. In another embodiment, the one or more heat producing electrical components may be advantageously positioned or mounted on circuit board 900 to create a thermal flow that promotes airflow to/through the smoke chamber 700 and/or relative to other components mounted on circuit board 900. For example, one or more microprocessors or resistors may be arranged on the circuit board to create free or natural convective air currents that cause air to flow through smoke chamber 700 and/or across other components mounted on the circuit board 900. In this manner, cooling of the one or more electrical components and/or airflow within hazard detector 400 may be increased.

In some embodiments, other components of the hazard detector 400 may likewise be mid-mounted relative to circuit board 900 and/or protective plate 800. For example, in one embodiment a CO detector is mid-mounted with respect to circuit board 900 and/or protective plate 800 such that a top surface of the CO detector is positioned above the top surface of the circuit board 900 and/or protective plate 800 while a bottom surface of the CO detector is positioned below a bottom surface of the circuit board 900 and/or protective plate 800. As such, air may be accessible to the CO detector from both the top surface and a bottom surface of the circuit board 900 and/or protective plate 800. In another embodiment, an additional airflow dependent sensor, such as in air quality sensor, a pollen detector, flow rate sensor, and the like, may be mid-mounted with respect to the circuit board 900 and/or protective plate 800 so that air is accessible to the additional air flow dependent sensor from both the top surface and bottom surface of the circuit board 900 and/or protective plate 800.

As described herein, an advantageous feature of the mid-mounted smoke chamber 700 is the reduction or elimination of pressure regions within the hazard detector 400 and adjacent the smoke chamber 700 since smoke and other gases may easily flow through the smoke chamber 700 and hazard detector 400. To further promote the flow of air, smoke, and other gases through the smoke chamber 700, the hazard detector 400 may be equipped with one or more micro-fans that draw air into the hazard detector 400 from one region and cause the air to flow out of the hazard detector 400 in another region. The micro-fans can be positioned to cause the air to pass through the smoke chamber 700 and circuit board 900 to prevent air pressure buildup near the smoke chamber 700. In addition to or as an alternative to micro-fans, silent-running modules having no moving parts that electrostatically accelerate air ionized by virtue of a coronal discharge effect can be used. The increased flow of air may provide additional cooling benefits to the various components mounted on circuit board 900.

Circuit board 900 may also include a micro-air flow detector that is designed to monitor and measure a flow of air passing by the circuit board 900 and/or through the smoke chamber 700. In some embodiments, the top and bottom surface of the circuit board 900 may each include an air flow detector so that the air flow relative to the top and bottom surfaces of circuit board 900 may be monitored and measured. If abnormalities are detected, such as a significant drop in air flow relative to one or both surfaces, an occupant of the building may be alerted to a potential problem with the hazard detector 400. For example, the occupant may be alerted to it blocked or clogged air passageway of hazard detector 400. To detect abnormalities, the hazard detector 400 may be designed to monitor the air flow patterns for a defined amount of time so as to learn the air flow patterns of the home or structure and/or an average air flow rate of the home or structure.

In another embodiment, the home or structure may include a plurality of hazard detectors 400 that are positioned in various rooms, hallways, equipment rooms, and the like. The air flow data associated with each location may be measured and monitored and recorded in a centralized database. This data may be analyzed to help determine the air flow currents or patterns of the home or structure. This information may then be used to optimize placement of hazard detectors 400 within the building so as to position the hazard detectors 400 in locations that are most likely to be exposed to smoke quickly. In some embodiments, a message may be transmitted to an occupant of the building that illustrates the measured air flow patterns and/or suggests a placement scheme based on the analyzed data. The data collected in the centralized database may be provided to and used by homebuilders, city planners, and the like to determine how to improve the efficiency of homes and/or residential areas.

Figure 5A:
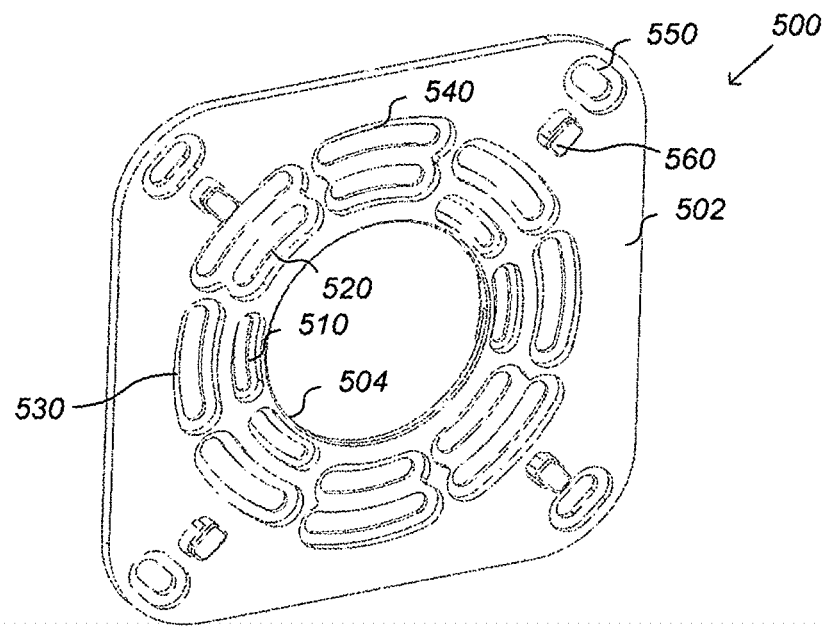
FIGS. 5A-C illustrate a front view and perspective views of a mounting plate of the hazard detector of FIGS. 4A-F, according to an embodiment.
Figure 5B:
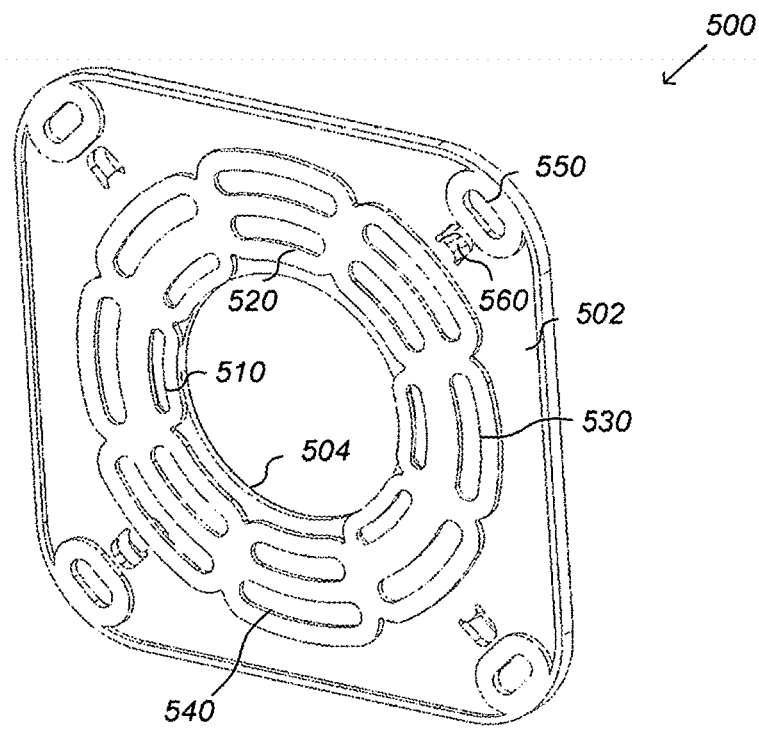
Figure 5C:
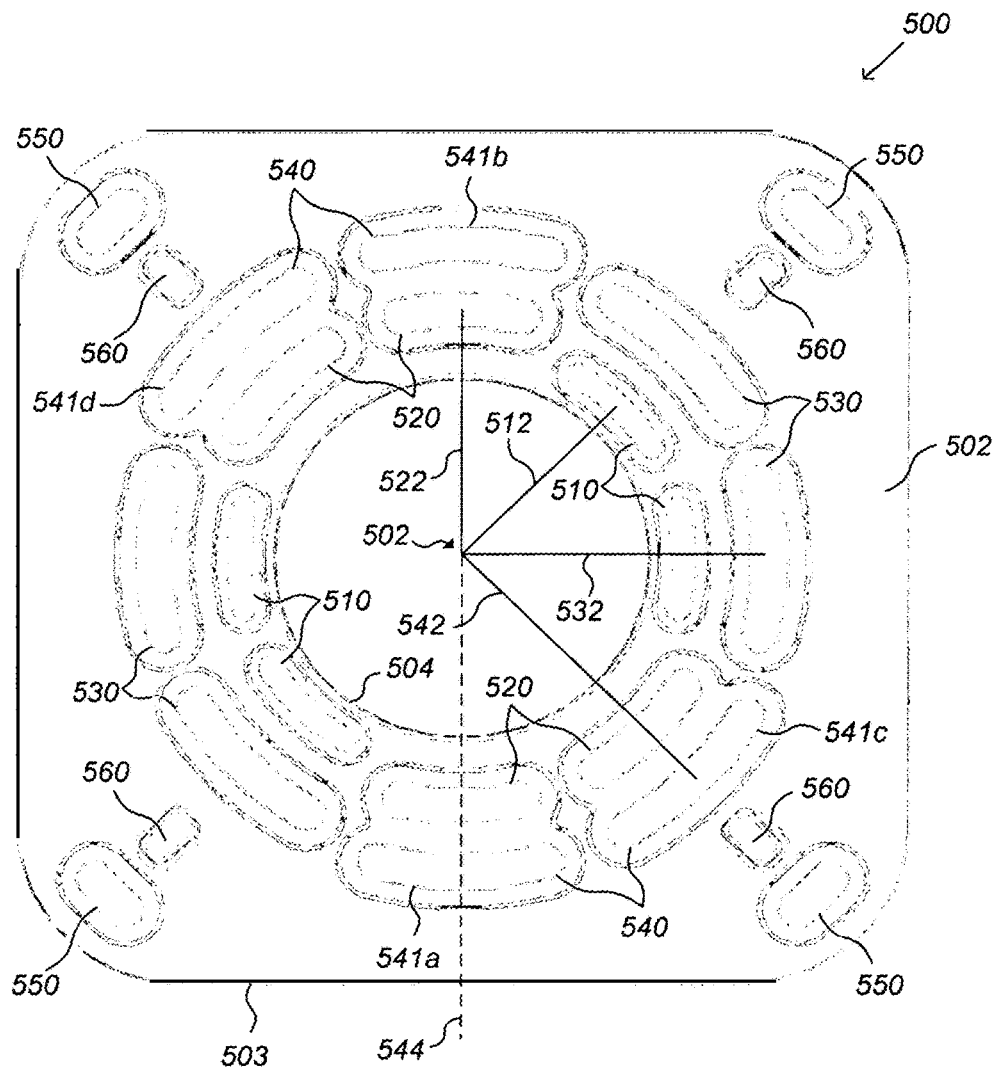

Referring now to FIGS. 5A-5C, illustrated are a front view and front and rear perspective views of the mounting plate 500 that allows hazard detector 400 to be coupled with a wall or ceiling of a structure or home within which the hazard detector is to be positioned to detect a potential fire or other hazard. Mounting plate 500 includes a body 502 that includes a plurality of holes or apertures that allow the mounting plate 500 to be mounted to the wall or ceiling in numerous positions. In some embodiments, mounting plate 500 is designed to cover a hole in the wall or ceiling that is cut around an electrical gang box or wall box. Measured diagonally, electrical gang boxes or wall boxes are typically about 100 mm across. As such, a hole in the wall or ceiling is typically about this size (i.e., about 100 mm across). To cover and hide the hole in the wall, mounting plate 500 may be sized about or slightly larger than 100 mm across. For example, in one embodiment, mounting plate 500 is sized to be about 110 mm to 120 mm or larger measured diagonally, which provides a 5 mm to 10 mm overlap margin per side (i.e., 10 mm to 20 mm total) compared with the wall hole cut around the gang or wall box.

In other embodiments, mounting plate 500 may be mounted to a wall or ceiling without a hole that is cut around an electrical gang box or wall box. In some embodiments, body 502 comprises a thickness between about 1.5 and 6 mm, although a thickness of about 3 mm is more common. The backplate 600, which is removably coupled with mounting plate 500 is typically sized slightly larger than the mounting plate 500 such that the mounting plate 500 is hidden from view when the components are coupled together to provide a visual appearance of the hazard detector being positioned adjacent the wall, yet slightly offset therefrom.

Body 502 includes a centrally located or positioned aperture 504 through which electrical wiring may be inserted to "hardwire", or otherwise electrically couple, the hazard detector 400 with the wiring of the home or structure. Body 502 also includes a plurality of hooked members or bayonets 560 that extend axially outward from an outward facing surface of the body 502 and that engage with corresponding apertures (e.g., apertures 606 of FIGS. 6A and 6B) positioned on or near an inward facing surface of the back plate 600 to allow the mounting plate 500 to removably couple with back plate 600. As shown in FIGS. 5A and 5B, body 502 may include four hooked members 560 positioned near respective edges of body 502. Each hooked member 560 faces outwardly from body 502 so as to be insertable within the corresponding apertures 606 of the back plate 600.

Mounting plate 500 also includes four holes 550 that are positioned near opposite corners of body 502. Holes 550 are mainly used when hazard detector 400 is being mounted to a wall or ceiling without attaching the mounting plate 500 to an electrical box, wall box, gang box, and the like, such as when the hazard detector 400 is not going to be hardwired to the electrical wires of the home or structure. Stated differently, holes 550 are mainly used when the hazard detector 400 is mounted directly to the wall or ceiling without coupling the mounting plate 500 to an electrical box. One common situation in which the hazard detector 400 is mounted to the wall or ceiling without coupling the mounting plate 500 to an electrical box is when the hazard detector 400 is mounted with drywall or wallboard in a home or structure. A screw, nail, or other mechanical fastening device may be easily inserted through holes 550 to attach the mounting plate 500 to the wall or ceiling of the structure or building (e.g., drywall, wallboard, and the like) within which the hazard detector is to be positioned.

Body 502 further includes a plurality of apertures that are spaced and arranged circumferentially around aperture 504. Specifically, body 502 includes a first set of apertures 510, a second set of apertures 520, a third set of apertures 530, and a fourth set of apertures 540. Each of these apertures are arranged according to an attachment standard of electrical boxes or gang boxes that are common in one or more countries or regions around the world, such as in the United States and Europe. The spacing and arrangement of these apertures allow the mounting plate 500 to be easily fit to a wall box or gang box regardless of the specific attachment standard(s) used in a given country. Further, these apertures are slotted to allow the mounting plate 500 and hazard detector 400 to be mounted to a wall or ceiling while having some degree of rotational freedom relative to the wall or ceiling. For example, the slotted apertures allow the mounting plate 500 and hazard detector 400 to be mounted at a roughly 90° or 45° configuration relative to the wall or some other feature of the room and subsequently rotated plus or minus 45-60° relative thereto.

Each set of apertures, 510, 520, 530, and 540, includes four slotted apertures spaced and arranged circumferentially around aperture 504. The four slotted apertures are arranged into pairs with each slotted aperture of a pair being spaced approximately 180 degrees apart so that the slotted apertures of the pair are positioned on opposite sides of aperture 504. For example, a first slotted aperture 541a and second slotted aperture 541b of aperture set 540 form an aperture pair and are positioned approximately 180 degrees apart on opposite sides of aperture 504. First slotted aperture 541a is arranged about body 502 so that an axis 544 that extends from a central axis 502 of aperture 504 and through a center point or region of first slotted aperture 541a forms a roughly 90° angle with an edge 503 of body 502. A third slotted aperture 541c and fourth slotted aperture 541d of aperture set 540 also form an aperture pair and are positioned approximately 180 degrees apart on opposite sides of aperture 504. Third slotted aperture 541c is arranged about body 502 so that an axis 542 that extends from central axis 502 and through a center point or region of third slotted aperture 541c forms a roughly 45° angle with edge 503 and/or axis 544. The slotted apertures of aperture sets 510, 520, and 530 are similarly arranged about body 502.

This slotted aperture pair configuration allows the mounting plate 500 and hazard detector 400 to be secured to the wall or ceiling in a manner wherein an edge of the hazard detector is angled at roughly 90° or 45° relative to a floor, wall, and/or ceiling of the room within which the hazard detector 400 is positioned. The mounting plate 500 and hazard detector 400 may then be rotated within the slotted apertures (510, 520, 530, and 540) as desired by the user (e.g., up to between 45-60°) to fine tune the positioning of the hazard detector 400 relative to the wall or floor and/or to adjust the hazard detector 400 so that an edge of the hazard detector 400 is angled at some desired degree relative to the wall or floor. In this manner, the user may make the hazard detector 400 appear to have a relatively box or square configuration relative to a wall or ceiling so that an edge of the hazard detector 400 is approximately level with respect to a floor or wall of the room. In another configuration, the user may arrange the hazard detector 400 to have a relatively diamond-shaped configuration relative to the wall or ceiling so that an edge of the hazard detector 400 is angled at approximately 45° with respect to a floor or wall of the room. Other hazard detector configurations are likewise possible by rotating the hazard detector 400 within the slotted apertures (510, 520, 530, and 540) so that an edge of the hazard detector 400 is angled at essentially any desired degree (e.g., between 30-60°) with respect to a floor or wall of the room.

According to one embodiment, the first set of apertures 510 is arranged on body 502 circumferentially around aperture 504 and dimensioned according to a first attachment standard of a first electrical box or gang box. The first attachment standard defines a distance or spacing range of the first set of apertures 510. In one embodiment, the first attachment standard defines a hole or aperture spacing of about 60 mm for the first set of apertures 510. Stated differently, the first attachment standard may define that each slotted aperture 510 has a roughly 30 mm radius 512 from central axis 502 of aperture 504. Arranging and dimensioning the first set of apertures 510 according to the first attachment standard allows the mounting plate 500 to be coupled with the first electrical box or gang box when the first electrical box or gang box is attached to a wall or ceiling of a building or structure. The second set of apertures 520 is arranged on body 502 circumferentially around aperture 504 and dimensioned according to a second attachment standard of a second electrical box or gang box. The second attachment standard defines a distance or spacing range of the second set of apertures 520. In one embodiment, the second attachment standard defines a hole or aperture spacing of about 71 mm for the second set of apertures 520. Stated differently, the second attachment standard may define that each slotted aperture 520 has a roughly 35.5 mm radius 522 from central axis 502 of aperture 504. Arranging and dimensioning the second set of apertures 520 according to the second attachment standard allows the mounting plate 500 to be coupled with the second electrical box or gang box when the second electrical box or gang box is attached to a wall or ceiling of a building or structure.

Similarly, the third set of apertures 530 is arranged on body 502 circumferentially around aperture 504 and dimensioned according to a third attachment standard of a third electrical box or gang box. The third attachment standard defines a distance or spacing range of the third set of apertures 530. In one embodiment, the third attachment standard defines a hole or aperture spacing of about 83.5 mm for the third set of apertures 530. Stated differently, the third attachment standard may define that each slotted aperture 530 has a roughly 41.75 mm radius 532 from central axis 502 of aperture 504. Arranging and dimensioning the third set of apertures 530 according to the third attachment standard allows the mounting plate 500 to be coupled with the third electrical box or gang box when the third electrical box or gang box is attached to a wall or ceiling of a building or structure. The fourth set of apertures 540 are arranged on body 502 circumferentially around aperture 504 and dimensioned according to a fourth attachment standard of a fourth electrical box or gang box. The fourth attachment standard defines a distance or spacing range of the fourth set of apertures 540. In one embodiment, the fourth attachment standard defines a hole or aperture spacing of about 88 mm for the fourth set of apertures 540. Stated differently, the fourth attachment standard may define that each slotted aperture 540 has a roughly 44 mm radius 542 from central axis 502 of aperture 504. Arranging and dimensioning the fourth set of apertures 540 according to the fourth attachment standard allows the mounting plate 500 to be coupled with the fourth electrical box or gang box when the fourth electrical box or gang box is attached to a wall or ceiling of a building or structure.

In some embodiments, each slotted aperture (510, 520, 530, and 540) may be configured to allow the mounting plate 500 to be rotated between about 10 degrees and 30 degrees relative to an electrical box the mounting plate 500 is coupled with. In another embodiment, each slotted aperture (510, 520, 530, and 540) may be configured to allow the mounting plate 500 to rotate about 15 degrees relative to an electrical box the mounting plate 500 is coupled with. In this manner, the total rotational freedom of the mounting plate 500, and thus the hazard detector 400, relative to an electrical box provided by the slotted apertures (510, 520, 530, and 540) may be between about 20 degrees and 60 degrees.

In some embodiments, the more arcuate or slotted each slotted aperture (510, 520, 530, and 540) is made, the larger the rotational freedom provided to the mounting plate 500. Conversely, the more arcuate or slotted each slotted aperture (510, 520, 530, and 540) is made, the more space each slotted aperture (510, 520, 530, and 540) occupies on body 502, which may cause adjacent slotted aperture to overlap and interfere with one another. A slot shape or configuration that allows the mounting plate 500 to rotate between about 10 degrees and 30 degrees relative to an electrical box has been found to provide a good balance of rotational freedom while minimizing adjacent slotted aperture overlap. In another embodiment each slotted aperture may be configured to allow the mounting plate 500 to rotate between about 10 degrees and 20 degrees relative to an electrical box, and in a specific embodiment, each slot may be configured to allow the mounting plate 500 to rotate about 15 degrees relative to the electrical box. A slotted aperture configuration allowing between 10 degrees and 20 degrees of rotation freedom provides a sizing advantage over the slotted aperture configuration allowing 10 to 30 degrees of rotation freedom (i.e., less slotted aperture overlap concerns), but also restricts the overall rotational freedom. The slot configuration allowing approximately 15 degrees provides an optimal advantage of rotational freedom and slotted aperture size. In some embodiments, some or all slotted apertures may be sized differently. In another embodiment, each slotted aperture within a slotted aperture pair may be sized the same while other slotted aperture pairs are sized differently. Various combinations are possible as desired.

In one embodiment, two of the attachment standards (i.e., the first, second, third, or fourth attachment standards) correspond to attachment standards that are used in a first country or region of the world, such as the United States, while the other two attachment standards correspond to attachment standards that are used in a second country or region of the world, such as in Europe. Since mounting plate 500 includes slotted apertures sets (510, 520, 530, and 540) that are configured to fit each of the four attachment standards, mounting plate 500 is adaptable and mountable to various electrical boxes, wall boxes, or gang box regardless of the attachment standards used and regardless of the region where the hazard detector 400 is being used. This essentially allows the hazard detector 400 to be mounted to an electrical, wall, or gang box regardless of the specific attachment standard used in the home or structure.

In one embodiment, the mounting plate 500 may be configured to easily adapt to the various mounting standards of other electrical devices (e.g., thermostats, ceiling fans, lighting fixtures, and the like) to enable the mounting plate 500 to easily attach numerous electrical devices with numerous electrical boxes. For example, the different electrical devices may each use an attachment standard that is different from other electrical devices or relatively unique to a product, manufacturing company, and the like. Thus, mounting the various electrical devices with an electrical box may be a relatively difficult task. The mounting plate 500 described herein may include a plurality of sets of hooked members (e.g., 560) that are each arranged according to popular mounting standards so that the mounting plate 500 may be easily attached to various electrical devices as well as being easily attached to various electrical boxes.

In one embodiment, a second mounting plate (not shown) may be used to enable coupling of various electrical devices with various electrical boxes. For example, a first mounting plate (not shown) may include a plurality of slotted aperture sets (not shown) that are dimensioned and arranged according to various electrical box attachment standards as described herein. The first mounting plate may be easily attached to a specific electrical box having a specific attachment standard as described above. A second mounting plate (not shown) may also include a plurality of slotted aperture sets (not shown) that are each dimensioned and arranged according to popular mounting standards of electrical devices. The second mounting plate may be easily attached to a specific electrical device by inserting fasteners through apertures of the slotted aperture sets that correspond to the specific mounting standard of the electrical device. The first and second mounting plates may then be coupled together, such as by inserting hooked members (not shown) of the first mounting plate through corresponding apertures (not shown) of the second mounting plate. The use of the second mounting plate may also allow the electrical device to be easily uncoupled from the electrical box for repair, replacement, cleaning, and the like.

Figure 6A:
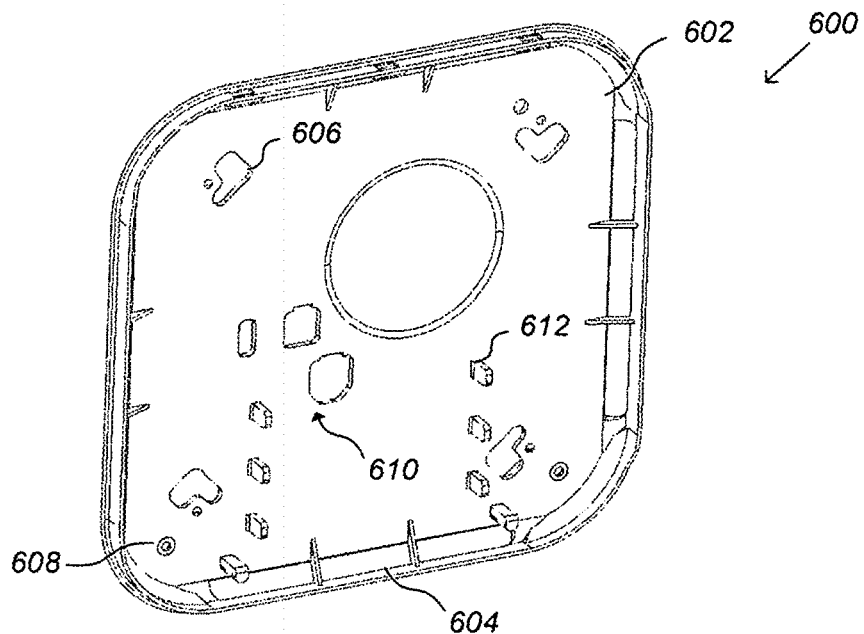
FIGS. 6A-B illustrate front and rear perspective views of a back plate of the hazard detector of FIGS. 4A-F, according to an embodiment.
Figure 6B:
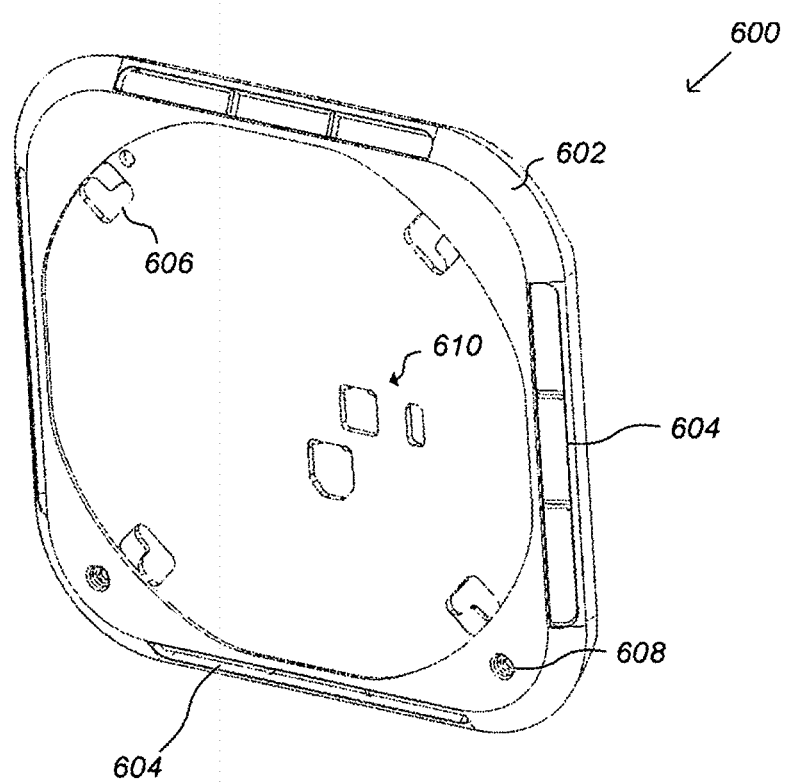

Referring now to FIGS. 6A and 6B, illustrated are front and rear perspective views of back plate 600. Back plate 600 includes a body 602 having a plurality of apertures 606 that are configured to mate with hooks 560 of mounting plate 500 to secure the back plate 600 and hazard detector 400 to the mounting plate 500 and to a wall or ceiling of a structure or home. Back plate 600 covers a rear portion of the internal components of hazard detector 400 to encase the internal components within the hazard detector device. In addition, some of the other components of hazard detector 400 (e.g., circuit board 900 and the like) are mounted or otherwise coupled with the back plate 600. Back plate 600 couples with the front casing 1100 to define a housing within which the components are contained. In some embodiments, back plate 600 and front casing 1100 may be permanently coupled together, while in other embodiments front casing 1100 may be removable from back plate 600 so that the internal components are accessible to the user, for example to change batteries of the hazard detector 400.

As shown, back plate 600 includes vents 604 within body 602 that allow air to flow into hazard detector 400. As described herein, an edge or edges of protective play 800 may be positioned adjacent or near vents 604 to direct air and smoke to flow from vents 604 towards an internally mounted smoke chamber 700. Body 602 also includes one or more apertures 610 through which electrical wires of the home or structure may be inserted to hardwire the hazard detector 400 to the home or structure's electrical wiring. Body 602 may also include one or more posts 612 that are used to mount and/or position various components of hazard detector 400 within the housing defined by back plate 600 and front casing 1100. Body 602 may further include various apertures or ports 608 through which screws or other mechanically fastening devices may be inserted to attach the various internal components of hazard detector 400 to back plate 600.

Figure 7A:
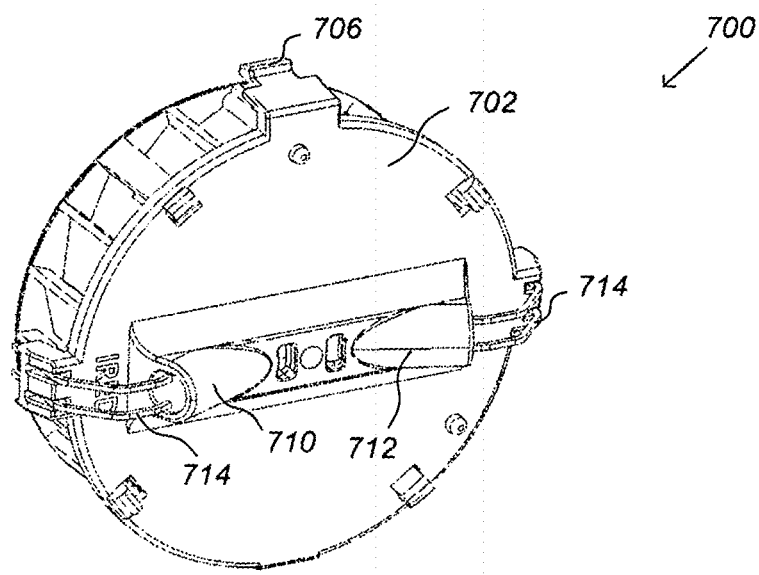
FIGS. 7A-E illustrate various perspective views of a smoke chamber of the hazard detector of FIGS. 4A-F, according to an embodiment.
Figure 7B:
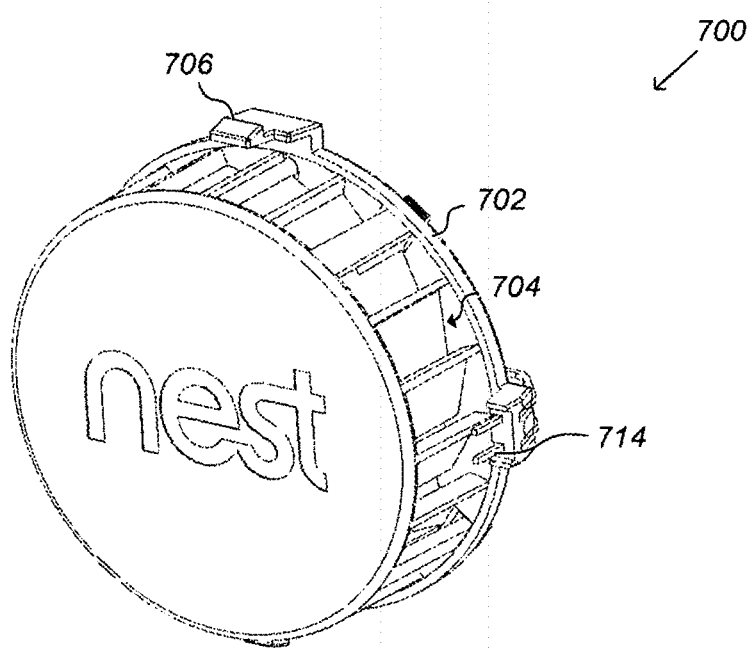

Referring now to FIGS. 7A and 7B, illustrated is an embodiment of a smoke chamber 700. As shown, smoke chamber 700 comprises a body 702 having a roughly cylindrical configuration, although other configurations are possible. In some embodiments, body 702 may have a diameter of between about 30 and 50 mm. In another embodiment, body 702 may have a diameter of between about 35 and 45 mm. In a specific embodiment, body 702 may have a diameter of about 42 mm. Body 702 may also have a height of between about 10 and 15 mm, with a specific embodiment having a height of about 12.5 mm. Smoke chamber 700 further includes a plurality of baffles 704 positioned circumferentially around the smoke chamber 700. An opening of the baffles may be approximately 1.2 mm or smaller to prevent bugs and other objects larger than 1.3 mm from entering the smoke chamber 700 while allowing air and smoke to freely enter therein. Smoke chamber 700 may be an optical smoke sensing device, ionization type smoke sensing device, photoelectric smoke sensing device, and the like. In one embodiment, smoke chamber 700 may be and optical device that includes a light source 710 (e.g. LED and the like) and a light detecting source 712 (e.g. photodiode and the like) for detecting the presence of smoke. With the light source 710 and/or light detecting source 712, body 702 may have a height of between about 15 and 20 mm, with a specific embodiment having a height of about 18.9 mm. An axis of the light source 710 may be offset from an axis of the photodiode 712, such as by 30°, so that light emitted by light source 710 is not readily detected by the photodiode 712 unless smoke or other particles are within the interior region of smoke chamber 700. The smoke detecting components (e.g., light source 710 and light detecting source 712) may be electrically coupled via wires 714 to the circuit board 900 so that upon detecting the presence of smoke an alarm device may be triggered or so that other information may be communicated to components mounted on or otherwise electrically coupled with the circuit board 900. Body 702 may include one or more flanges 706 that are used to couple the smoke chamber 700 with the circuit board 900 and/or protective plate 800, or otherwise secure the smoke chamber 700 relative thereto.

In some embodiments, smoke chamber 700 may include other components in addition to smoke detecting components. For example, an additional light source (e.g. UV, infrared, visible light, or laser) or light detecting source component (e.g., Photodiode, phototransistor, or silicon photomultiplier) may be used within smoke chamber 700 to detect the presence of pollen, a quality of the air, humidity, and the like via techniques such as spectroscopy, measuring IR absorption or observing fluorescence. The additional light source or light detecting source component could be used to increase the sensitive area inside the smoke chamber so that more particles in the chamber can be seen. The additional light source or light detecting source component could be used to help distinguish between smoke and a false alarm. In another embodiment, it could be used as a particle counter or pollen counter to give an indication of general air quality. Information about the pollen count may be provided to an occupant or occupants of the home or structure, or recorded on a central database, to help individuals be aware of possible allergy issues. In another embodiment, the additional components within smoke chamber 700 may be used to determine if the room is relatively humid, which may cause the hazard detector 400 to falsely trigger the alarm device. Differing light sources and wavelengths could be used to identify particle sizes to distinguish between water, smoke, or pollen. If the smoke chamber 700 determines that the humidity is relatively high, the sensitivity of the smoke detecting components may be reduced so as to reduce the occurrence of false alarms. In this manner, smoke chamber 700 may function as a multi-sensing unit. In other embodiments, the additional components may be positioned at locations within hazard detector 400 other than the smoke chamber.

Figure 7C:
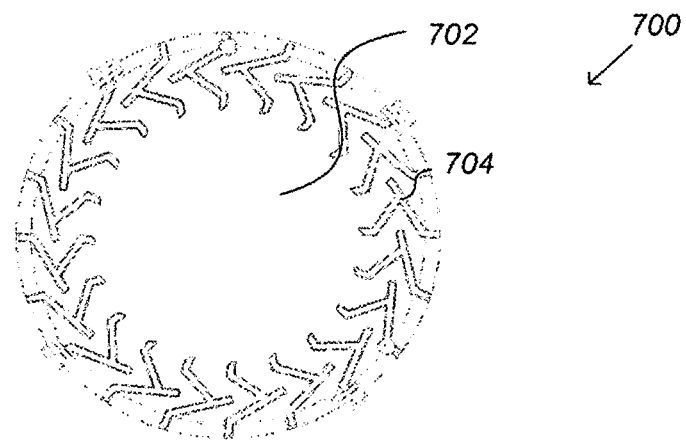
Figure 7D:
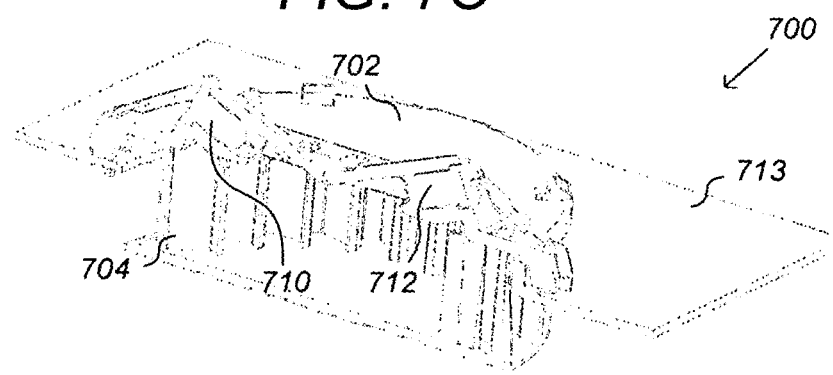
Figure 7E:

FIGS. 7C-E illustrate various cross section views of smoke chamber 700. Specifically, FIG. 7C illustrates a front cross sectional view where the cross sectional plane is orthogonal to an axis of smoke chamber 700 at approximately a mid-point axially along smoke chamber 700. FIG. 7C illustrates the baffles 704 positioned circumferentially around the body 702 of smoke chamber 700. As described herein, the baffles 704 may allow smoke to enter into smoke chamber 700 while preventing light, insects, dust, etc. from entering therein. FIG. 7D illustrates a cross sectional view taken along a plane orthogonal to the cross sectional plane of FIG. 7C and passing through light source 710 and photodiode 712. FIG. 7D provides another perspective of the interior portion of smoke chamber 700 and the baffles 704 positioned circumferentially around body 702. FIG. 7E illustrates another cross section view taken along a plane orthogonal to the cross sectional planes of FIGS. 7C and 7D. FIG. 7E provides yet another perspective of the interior portion of smoke chamber 700 and the baffles 704 positioned circumferentially around body 702. FIGS. 7D and 7E also illustrate the smoke chamber 700 being mid-mounted relative to a component 713 of hazard detector 400 (e.g., circuit board 900, protective plate 800, and the like). As shown, in the mid-mounted configuration, air, smoke, and other gas is flowable into the interior of smoke chamber 700 from both the top and bottom surface of component 713.

Figure 7F:
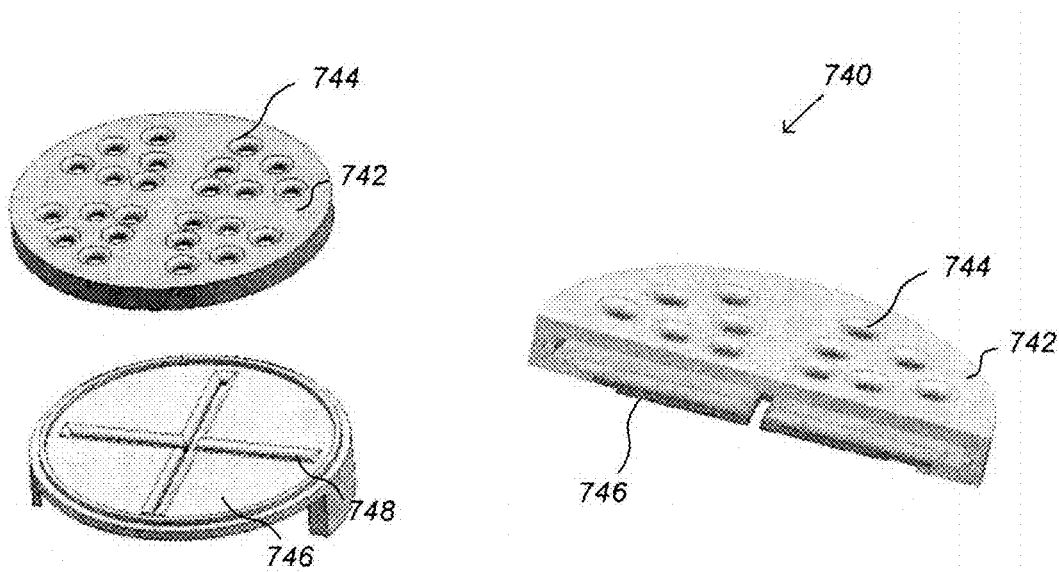
FIGS. 7F-G illustrate top and/or bottom surfaces of the smoke chamber of FIGS. 7A-E that include baffles through which air and smoke may flow, according to an embodiment.
Figure 7G:
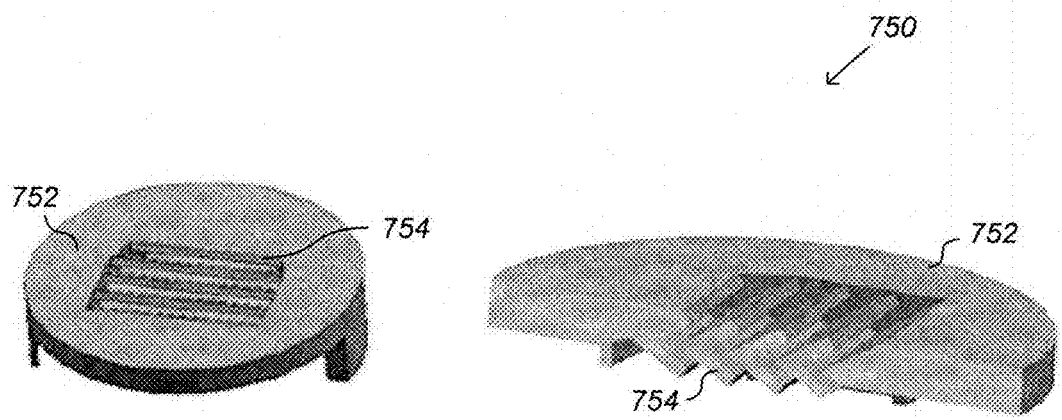

As shown in FIGS. 7F and 7G, in some embodiments, a smoke chamber may include additional baffles positioned on a top surface (i.e. near components 710 and 712) or a bottom surface so that smoke is flowable into the interior of the smoke chamber from the top surface, the bottom surface, and/or a side or sides of the smoke chamber. In one embodiment, the smoke chamber may include baffles positioned on each surface so that smoke is flowable into the interior of the smoke chamber from virtually any direction relative to the smoke chamber. With regard to optical or photoelectric smoke chambers, a particular concern with adding baffles to the top or bottom surface is limiting or eliminating the penetration of light into the smoke chamber, which may falsely trigger the alarm device. In hazard detectors employing such smoke sensor technology, the baffles must be capable of allowing smoke and air to enter into the smoke chamber while limiting or eliminating light from entering therein.

FIG. 7F illustrates one embodiment of a top or bottom surface 740 that includes baffles that are designed to limit the penetration of light into the smoke chamber. Specifically, a first plate 742 may include a plurality of openings or holes 744. The first plate 742 may be positioned over a second plate 746 having one or more slots 748. When the first plate 742 and second plate 746 are coupled together, the holes 744 and slots 748 may be offset to prevent or limit light from entering into the interior region of the smoke chamber while allowing smoke and air to enter therein. FIG. 7F also illustrates a cross section view of the coupled components. FIG. 7G also illustrate an embodiment of a top or bottom surface 750 that includes baffles that are designed to limit the penetration of light. Specifically, a single plate 752 may include diagonally shaped vanes or baffles 754 that prevent or limit light from entering into the interior region of the smoke chamber while allowing smoke and air to enter therein. The baffles 754 of plate 752 may include a labyrinth design to prevent light from penetrating into the interior region of the smoke chamber.

Figure 8A:
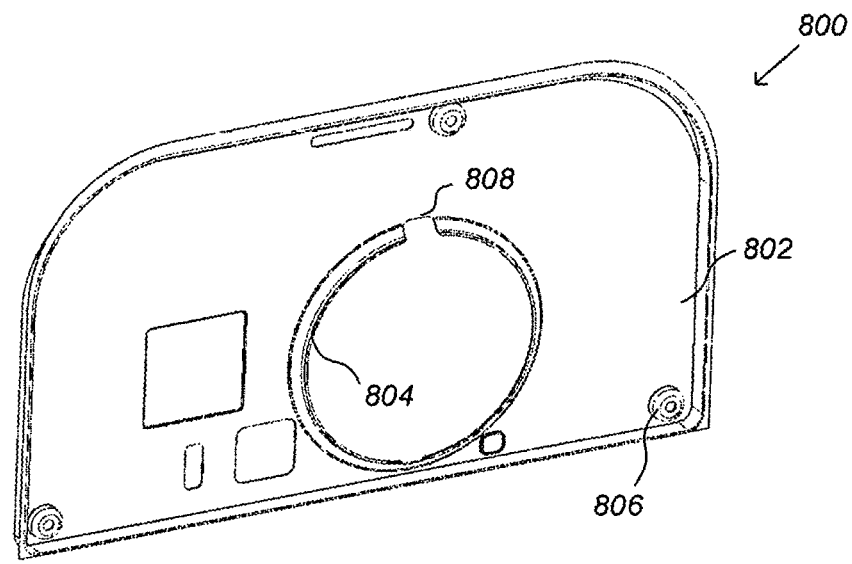
FIGS. 8A-B illustrate front and rear perspective views of a protective plate of the hazard detector of FIGS. 4A-F, according to an embodiment.
Figure 8B:
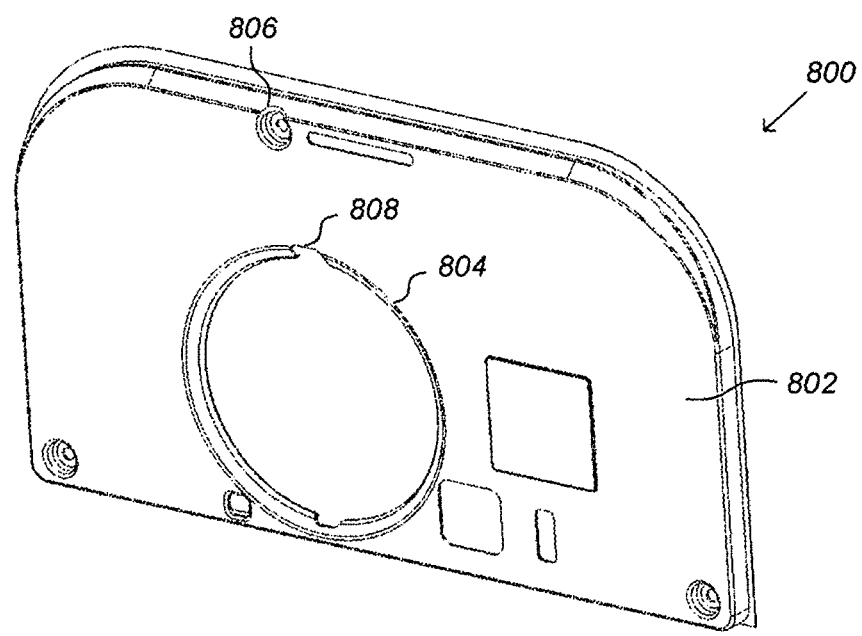

Referring now to FIGS. 8A and 8B, illustrated is a front and rear perspective view of a protective plate 800. Protective plate 800 includes a body 802 having a relatively centrally located aperture 804 through which the smoke chamber 700 is insertable to mid-mount the smoke chamber 700 relative to protective plate 800 as previously described. Body 802 also includes a pair of notches 808 positioned on opposite sides of the centrally located aperture 804 through which wires 714 are positioned to electrically couple smoke chamber 700 with circuit board 900. Body 802 also includes a plurality of holes 806 that allow the protective plate 800 to be attached to or otherwise coupled with circuit board 900 and/or back plate 600. As shown in FIG. 4F, when mounted with circuit board 900, protective plate 800 covers the various components mounted on the rear or bottom surface of circuit board 900. In this manner, protective plate 800 functions to prevent the components of circuit board 900 from being touched or viewed by a user, such as when the back plate 600 is removed to change batteries of hazard detector 400 or for various other reasons. In addition, if a user views the interior of hazard detector 400 through one of the vents 604 of back plate 600, the protective plate 800 hides the components of circuit board 900 from the user's view and provides a visually pleasing surface, thereby helping the hazard detector 400 have a cleaner and more pleasing appearance.

Protective plate 800 also optimizes air flow to smoke chamber 700 as well. For example, as previously described, the outer edges of protective plate 800 are positioned adjacent or near vents 604 of back plate 600 so that air and smoke entering hazard detector 400 via vents 604 is directed or funneled from the edge of hazard detector 400 towards smoke chamber 700. The relatively flat and smooth surface of protective plate 800 helps funnel or channel the air flow towards smoke chamber 700. Since smoke chamber 700 is mid-mounted relative to protective plate 800, smoke and air easily flow into smoke chamber 700 from a bottom surface of protective plate 800. Protective plate 800 may have one or more beveled or chamfered edges as shown positioned near smoke chamber 700 and/or one or more edges of protective plate 800.

Figure 9A:
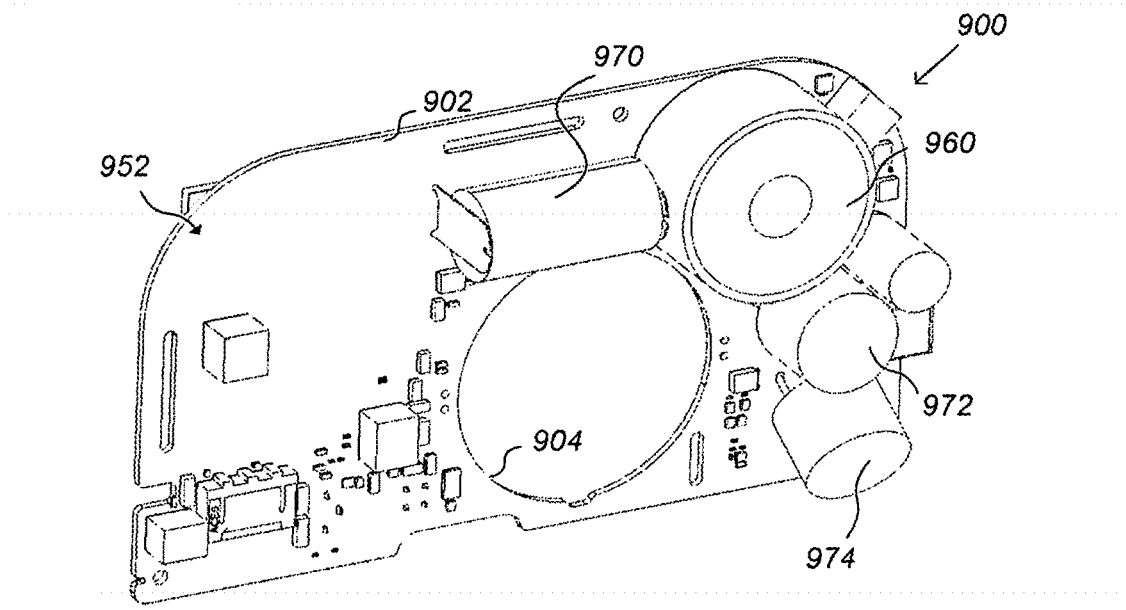
FIGS. 9A-B illustrate front and rear perspective views of a circuit board of the hazard detector of FIGS. 4A-F, according to an embodiment.
Figure 9B:
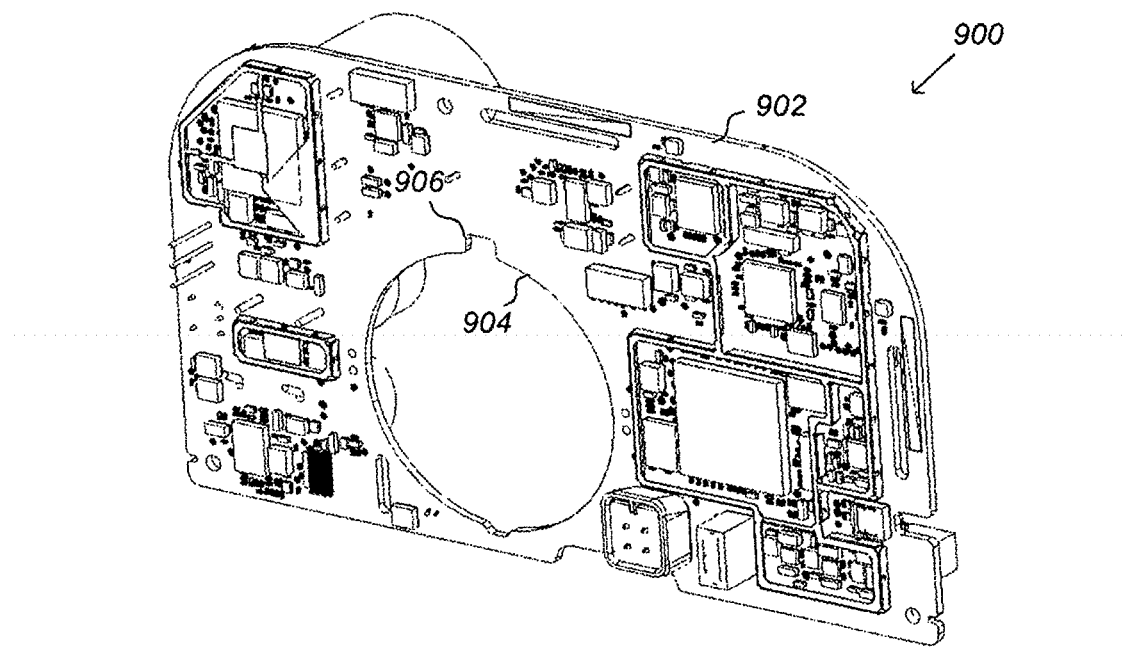

Referring now to FIGS. 9A and 9B, illustrated are front and rear perspective views of circuit board 900. Circuit board 900 includes a main body 902 having a front side or surface and a rear side or surface. As described herein, various electrical components are mounted on circuit board 900. In some embodiments, these components may be mounted on the front surface of circuit board 900, on the rear surface of circuit board 900 opposite the front surface, or on both surfaces of the circuit board 900. For example, in a specific embodiment one or more microprocessors and/or other processor related components may be mounted on the rear surface of circuit board 900 facing protective plate 800 while one or more functional components (e.g. an alarm device, CO detector, speaker, motion sensors, Wi-Fi module, Zigbee module, and the like) are mounted on a front surface of circuit board 900 facing a room of the home or structure in which the hazard detector 400 is positioned. Other components may be mid-mounted relative to circuit board 900 so that opposing surfaces are positioned on opposing sides of the circuit board 900 as described herein.

As shown in FIG. 9A, in a specific embodiment the front surface of circuit board 900 may include a CO detector 970 that is configured to detect presence of carbon monoxide gas and trigger an alarm device 960 if the carbon monoxide gas levels are determined to be too high. The alarm device 960 (which can be a piezoelectric buzzer having an intentionally shrill or jarring sound) may likewise be mounted on the front surface of circuit board 900 so as to face an occupant of the room in which the hazard detector 400 is positioned to alarm the occupant of a potential danger. Alarm device 960 may be configured to produce one or more sounds or signals to alert the occupant of the potential danger. The front surface may further include an area 952 in which a speaker 950 is positioned. Speaker 950 may be configured to provide audible warnings or messages to the occupant of the room. For example, speaker 950 may alert the occupant of a potential danger and instruct the occupant to exit the room. In some embodiments, speaker 950 may provide specific instructions to the occupant, such as an exit route to use when exiting the room and/or home or structure. Other messages may likewise be communicated to the occupant, such as to alert the occupant that the batteries are low, that CO levels are relatively high in the room, that hazard detector 400 needs periodic cleaning, or alert the occupant of any other abnormalities or issues related to hazard detector 400 or components thereof.

Circuit board 900 may also include one or more motion sensors mounted on the front surface thereof. The motion sensors may be used to determine the presence of an individual within a room or surrounding area of hazard detector 400. This information may be used to change the functionality of hazard detector 400 and/or one or more other devices connected in a common network as described previously. For example, this information may be relayed to a smart thermostat to inform the thermostat that occupants of the home or structure are present so that the smart thermostat may condition the home or structure according to one or more learned or programmed settings. Hazard detector 400 may likewise use this information for one or more purposes, such as to quiet the alarm device (e.g. gesture hush) as described herein or for various other reasons.

In one embodiment, a first ultrasonic sensor 972 and a second ultrasonic sensor 974 may be mounted on the front surface of circuit board 900. The two ultrasonic sensors, 972 and 974, may be offset axially so as to point in slightly different directions. In this orientation, each ultrasonic sensor may be used to detect motion of an individual based on an orientation of the hazard detector 400 relative to the room and/or occupant. Detecting the motion of the individual may be used to quiet the alarm device as described herein (i.e., gesture hush) or for any other reason. In one embodiment, an axis of the first ultrasonic sensor 972 may be oriented substantially outward relative to hazard detector 400 while an axis of the second ultrasonic sensor 974 is oriented an angle relative to the axis of first ultrasonic sensor 972. The first ultrasonic sensor 972 may sense motion of an individual when the hazard detector 400 is mounted on a ceiling of the home or structure. Because the first ultrasonic sensor 972 is oriented substantially outward relative to hazard detector 400, the first ultrasonic sensor 972 essentially looks straight down on individuals beneath hazard detector 400. The second ultrasonic sensor 974 may similarly sense motion of the individual when the hazard detector 400 is mounted on a wall of the home or structure. Because the second ultrasonic sensor 974 is oriented at an angle relative to the first ultrasonic sensor 972 and hazard detector 400, the second ultrasonic sensor essentially looks downward toward the floor when the hazard detector 400 is mounted on a wall of the home or structure, rather than looking directly outward as first ultrasonic sensor 972. In one embodiment, the angular offset of the two ultrasonic sensors may be approximately 30° or any other desired value.

In another embodiment, the two ultrasonic sensors, 972 and 974, may be replaced by a single ultrasonic sensor that is configured to rotate within hazard detector 400 so that the single ultrasonic sensor is capable of looking straight outward similar to first ultrasonic sensor 972 or capable of looking downward similar to second ultrasonic sensor 974. The single ultrasonic sensor may be coupled to circuit board 900 via a hinge that allows the ultrasonic sensor to rotate based on the orientation of hazard detector 400. For example, when hazard detector 400 is mounted to a ceiling of the home or structure, gravity may orient the ultrasonic sensor so as to look straight downward; whereas when hazard detector 400 is coupled to a wall of the home or structure, gravity may cause the ultrasonic sensor to rotate via the hinge and look downward toward a floor and relative to hazard detector 400. In another embodiment, a motor may be coupled with the single ultrasonic sensor so as to rotate the ultrasonic sensor based on the orientation of hazard detector 400. In this manner, the ultrasonic sensor may always point in a direction that is likely to detect motion of an individual within the room or space surrounding the hazard detector 400. In yet another embodiment, the single ultrasonic sensor may have a wide field of view that is able to substantially accommodate both mounting positions of the two ultrasonic sensors, 972 and 974.

As shown in FIGS. 9A and 9B, body 902 of circuit board 900 also includes a substantially centrally located aperture 904 through which smoke chamber 700 is inserted so as to mid-mount the smoke chamber 700 relative to circuit board 900. Aperture 904 may also include a pair of notches 906 through which wires 714 are inserted to electrically couple the smoke chamber 700 with circuit board 900. As previously described, mid-mounting of the smoke chamber 700 through an aperture 904 allows smoke and air to enter smoke chamber 700 from both the front surface or side of circuit board 900 and the rear surface or side of circuit board 900. Various aspects of the electrical components on the circuit board 900 are now described, the positions thereon of many of which will be apparent to the skilled reader in view of the descriptions herein and FIGS. 9A-9B. Included on the circuit board 900 can be several components, including a system processor, relatively high-power wireless communications circuitry and antenna (e.g., Wi-Fi), relatively low-power wireless communications circuitry and antenna (e.g., ZigBee, Z-Wave, or other 802.15.4-based protocol), non-volatile memory, audio speaker 950, one or more interface sensors, a safety processor, safety sensors, alarm device 960, a power source, and powering circuitry. The components are operative to provide failsafe safety detection features and user interface features using circuit topology and power budgeting methods that minimize power consumption. According to one preferred embodiment, a bifurcated or hybrid processor circuit topology is used for handling the various features of the hazard detector 400, wherein the safety processor is a relatively small, relatively lean processor that is dedicated to core safety sensor governance and core alarming functionality as would be provided on a conventional smoke/CO alarm, and wherein the system processor is a relatively larger, relatively higher-powered processor that is dedicated to more advanced features such as cloud communications, user interface features, occupancy and other advanced environmental tracking features, and more generally any other task that would not be considered a "core" or "conventional" safety sensing and alarming task.

By way of example and not by way of limitation, the safety processor may be a Freescale KL15 microcontroller, while the system processor may be a Freescale K60 microcontroller. According to one embodiment, the safety processor is programmed and configured such that it is capable of operating and performing its core safety-related duties regardless of the status or state of the system processor. Thus, for example, even if the system processor is not available or is otherwise incapable of performing any functions, the safety processor will continue to perform its core safety-related tasks such that the hazard detector 400 still meets all industry and/or government safety standards that are required for the smoke, CO, and/or other safety-related monitoring for which the hazard detector 400 is offered (provided, of course, that there is sufficient electrical power available for the safety processor to operate). The system processor, on the other hand, performs what might be called "optional" or "advanced" functions that are overlaid onto the functionality of the safety processor, where "optional" or "advanced" refers to tasks that are not specifically required for compliance with industry and/or governmental safety standards. Thus, according to one embodiment, although the system processor is designed to interoperate with the safety processor in a manner that can improve the overall performance, feature set, and/or functionality of the hazard detector 400, its operation is not required in order for the hazard detector 400 to meet core safety-related industry and/or government safety standards. Being generally a larger and more capable processor than the safety processor, the system processor will generally consume more power than the safety processor when both are active.

Similarly, when both processors are inactive, the system processor will still consume more power than the safety processor. The system processor can be operative to process user interface features and monitor interface sensors (such as occupancy sensors, audio sensors, cameras, etc., which are not directly related to core safety sensing). For example, the system processor can direct wireless data traffic on both high and low power wireless communications circuitry, access non-volatile memory, communicate with the safety processor, and cause audio to be emitted from speaker 950. As another example, the system processor can monitor interface sensors to determine whether any actions need to be taken (e.g., shut off a blaring alarm in response to a user detected action to hush the alarm). The safety processor can be operative to handle core safety related tasks of the hazard detector 400. The safety processor can poll safety sensors (e.g., smoke, CO) and activate alarm device 960 when one or more of safety sensors indicate a hazard event is detected. The safety processor can operate independently of the system processor and can activate alarm device 960 regardless of what state the system processor is in. For example, if the system processor is performing an active function (e.g., performing a WiFi update) or is shut down due to power constraints, the safety processor can still activate alarm device 960 when a hazard event is detected.

In some embodiments, the software running on the safety processor may be permanently fixed and may never be updated via a software or firmware update after the hazard detector 400 leaves the factory. Compared to the system processor, the safety processor is a less power consuming processor. Using the safety processor to monitor the safety sensors, as opposed to using the system processor to do this, can yield power savings because safety processor may be constantly monitoring the safety sensors. If the system processor were to constantly monitor the safety sensors, power savings may not be realized. In addition to the power savings realized by using safety processor for monitoring the safety sensors, bifurcating the processors can also ensure that the safety features of the hazard detector 400 always work, regardless of whether the higher level user interface works. The relatively high power wireless communications circuitry can be, for example, a Wi-Fi module capable of communicating according to any of the 802.11 protocols.

By way of example, the relatively high power wireless communications circuitry may be implemented using a Broadcom BCM43362 Wi-Fi module. The relatively low power wireless communications circuitry can be a low power Wireless Personal Area Network (6LoWPAN) module or a ZigBee module capable of communicating according to a 802.15.4 protocol. For example, in one embodiment, the relatively low power wireless communications circuitry may be implemented using an Ember EM357 6LoWPAN module. The non-volatile memory can be any suitable permanent memory storage such as, for example, NAND Flash, a hard disk drive, NOR, ROM, or phase change memory. In one embodiment, the non-volatile memory can store audio clips that can be played back using the speaker 950. The audio clips can include installation instructions or warning in one or more languages. The interface sensors can includes sensors that are monitored by system processor, while the safety sensors can include sensors that are monitored by the safety processor. Sensors 220 and 232 can be mounted to a printed circuit board (e.g., the same board processor 210 and 230 are mounted to), a flexible printed circuit board, a housing of system 205, or a combination thereof.

The interface sensors can include, for example, an ambient light sensor (ALS) (such as can be implemented using a discrete photodiode), a passive infrared (PIR) motion sensor (such as can be implemented using an Excelitas PYQ1348 module), and one or more ultrasonic sensors (such as can be implemented using one or more Manorshi MS-P1640H12TR modules). The safety sensors can include, for example, the smoke detection chamber 700 (which can employ, for example, an Excelitas IR module), the CO detection module 970 (which can employ, for example, a Figaro TGS5342 sensor), and a temperature and humidity sensor (which can employ, for example, a Sensirion SHT20 module). The power source can supply power to enable operation of the hazard detector and can include any suitable source of energy. Embodiments discussed herein can include AC line powered, battery powered, a combination of AC line powered with a battery backup, and externally supplied DC power (e.g., USB supplied power). Embodiments that use AC line power, AC line power with battery backup, or externally supplied DC power may be subject to different power conservation constraints than battery only embodiments.

Preferably, battery-only powered embodiments are designed to manage power consumption of its finite energy supply such that hazard detector 400 operates for a minimum period of time of at least seven (7), eight (8), nine (9), or ten (10) years. Line powered embodiments are not as constrained. Line powered with battery backup embodiments may employ power conservation methods to prolong the life of the backup battery. In battery-only embodiments, the power source can include one or more batteries, such as the battery pack 1000. The batteries can be constructed from different compositions (e.g., alkaline or lithium iron disulfide) and different end-user configurations (e.g., permanent, user replaceable, or non-user replaceable) can be used. In one embodiment, six cells of Li—FeS$_2$ can be arranged in two stacks of three. Such an arrangement can yield about 27000 mWh of total available power for the hazard detector 400.

Figure 9C:
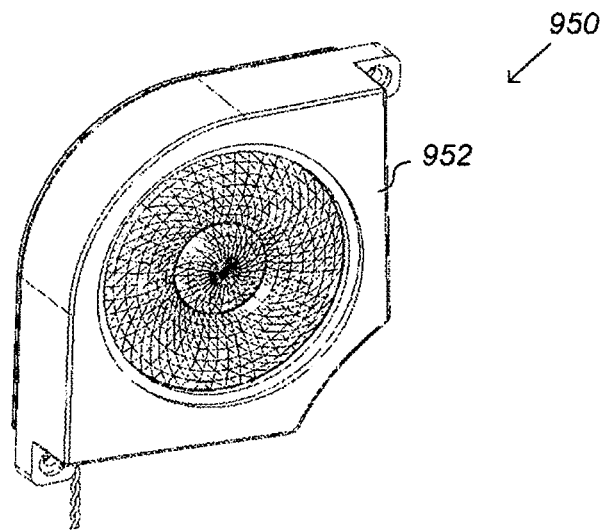
FIGS. 9C-D illustrate front and rear perspective views of a speaker that is mountable on the circuit board of the hazard detector of FIGS. 9A-B, according to an embodiment.
Figure 9D:
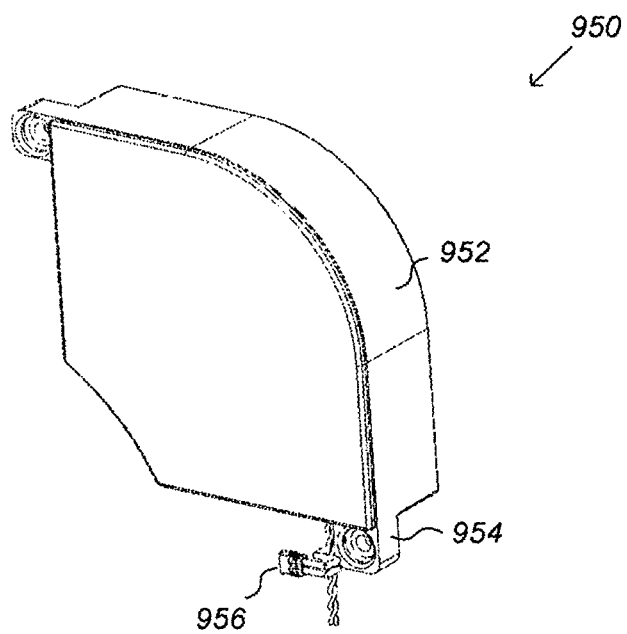

Referring now to FIGS. 9C and 9D, illustrated are front and rear perspective views of a speaker 950 that is electrically coupled with circuit board 900 so as to receive instructions therefrom. Speaker 950 includes a speaker body 952 and one or more mounting flanges 954 that allow the speaker 950 to be coupled with or mounted on front casing 1100. Speaker 950 also includes a plug 956 or other mounting component that allows the speaker 950 to be electrically coupled with circuit board 900. As previously described, speaker 950 may be used to audibly alert an occupant of a room within which hazard detector 400 is positioned, or to provide other messages to the occupant of the room. For example, speaker 950 may be used to alert a firefighter or other rescuer regarding the occupants remaining in the home or structure after a fire or other danger is detected or may be used to inform an occupant of a safest route out of the home or structure.

Figure 10A:
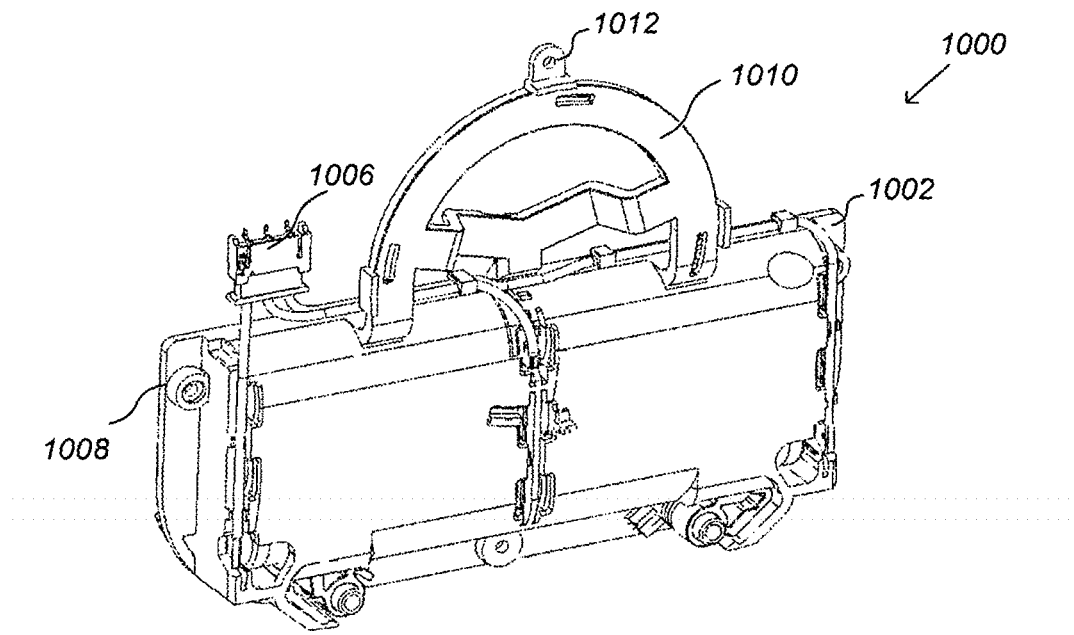
FIGS. 10A-B illustrate front and rear perspective views of a battery pack of the hazard detector of FIGS. 4A-F, according to an embodiment.
Figure 10B:
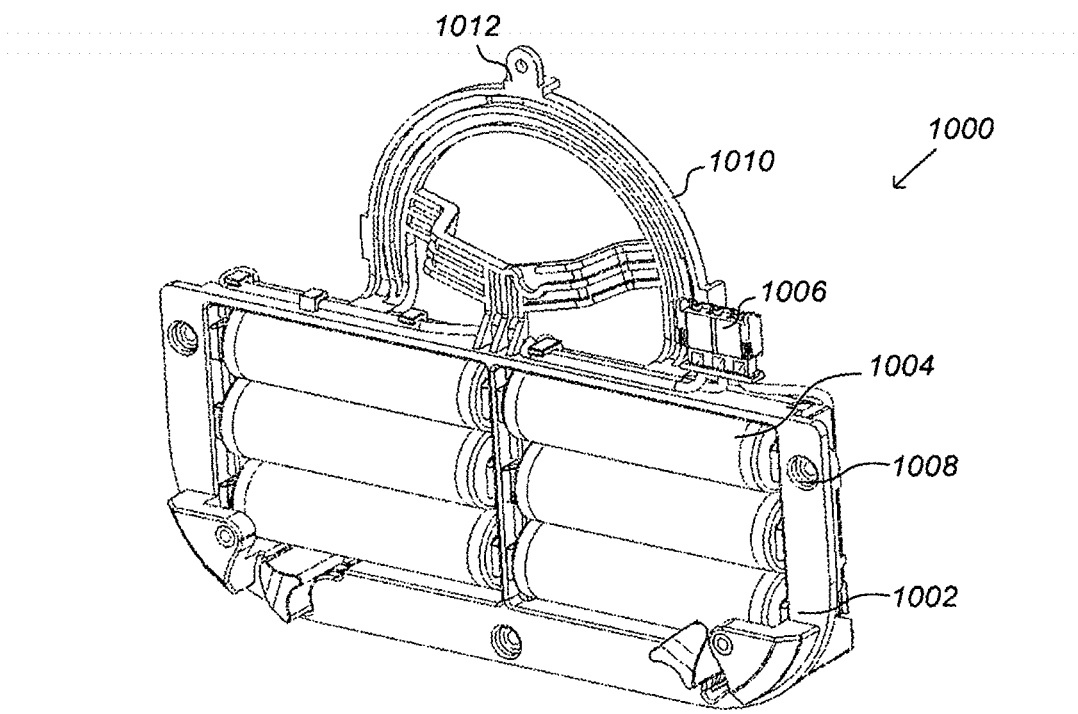

Referring now to FIGS. 10A and 10B, illustrated are front and rear perspective views of a battery pack 1000 of hazard detector 400. Battery pack 1000 includes a body 1002 within which batteries are positioned to power hazard detector 400. Specifically as shown in FIG. 10B, body 1002 includes a battery receptacle area 1004 within which the batteries are inserted. The batteries of hazard detector 400 may be rechargeable or one time use batteries as is common in the art. In some embodiments, hazard detector 400 may be designed to be a replaceable unit so that upon discharge of the batteries the entire hazard detector unit is replaced. In other embodiments, the back plate 600 and front casing 1000 of hazard detector 400 may be removed by a user so as to be able to access and replace the batteries.

Body 1002 includes one or more holes or apertures 1008 that allow the battery pack 1000 to be coupled with or otherwise mounted to the hazard detector 400, such as by attaching the battery pack 1002 to front casing 1100, back plate 600, and/or the like. Battery pack 1000 also includes an electrically coupling component 1006 that is configured to connect with circuit board 900 to provide power to the circuit board and the various components mounted thereon, such as the smoke chamber 700, the ultrasonic sensors 972 and 974, the microprocessors, the PIR sensor(s), and the like.

Battery pack 1000 further includes a radially arranged flange 1010 that is designed to function operationally with a button of front casing 1100. In some embodiments, radial flange portion 1010 is configured to support the button of front casing 1100. In other embodiments, radial flange portion 1010 may be designed to limit a vertical travel of the button as is pressed by user. The radial flange portion 1010 may be coupled with the front casing via a coupling component 1012, such as by inserting a screw through the coupling component 1012 which is then inserted into the front casing 1100.

Figure 11A:
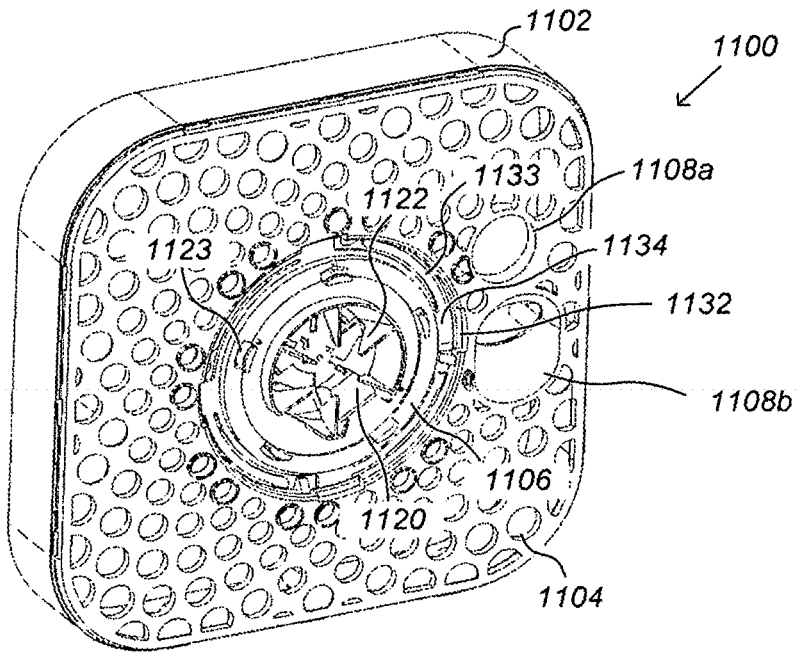
FIGS. 11A-J illustrate various views of a front casing of the hazard detector of FIGS. 4A-F, according to an embodiment.
Figure 11B:
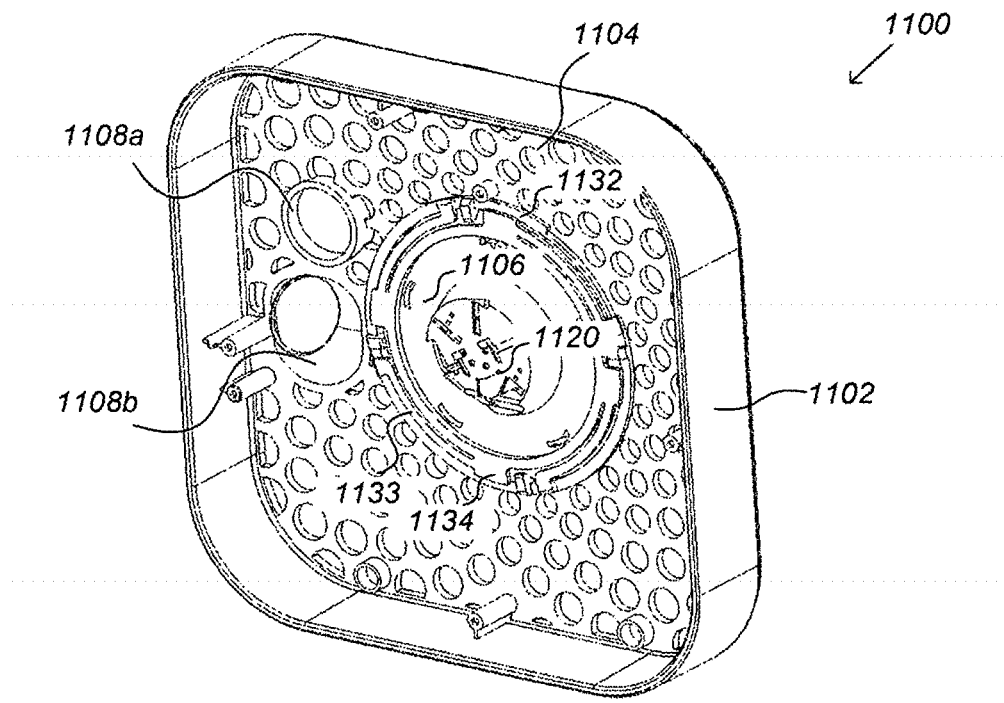
Figure 11C:
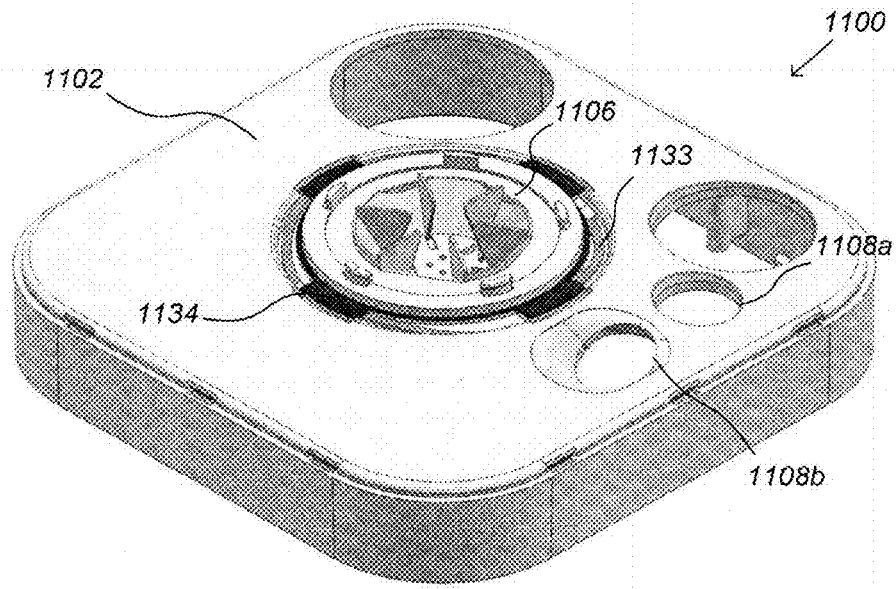
Figure 11D:
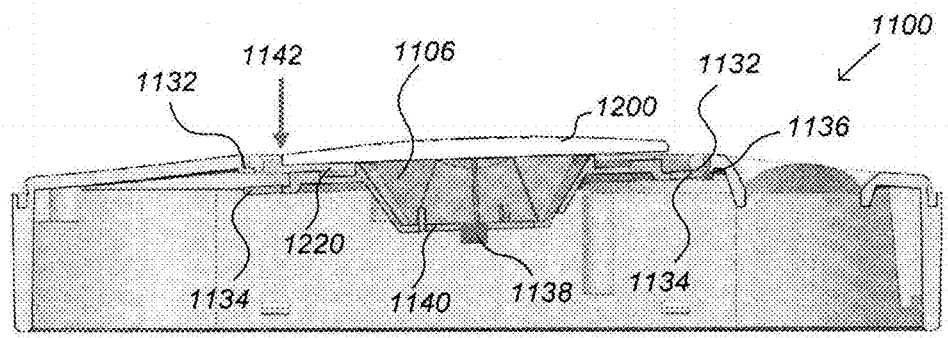
Figure 11E:
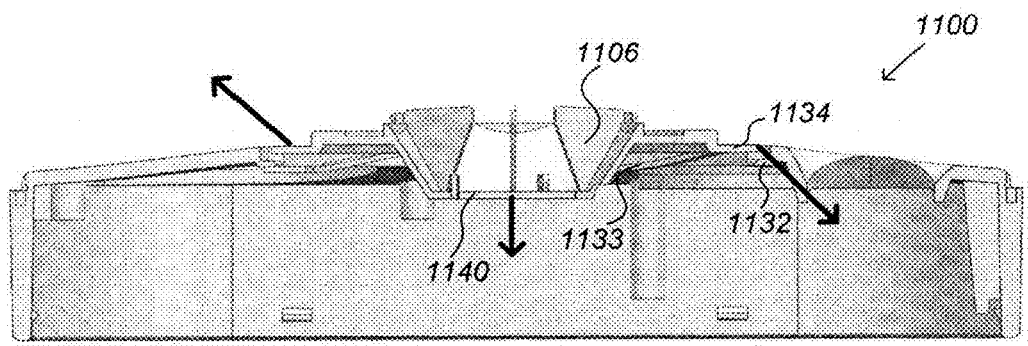
Figure 11F:
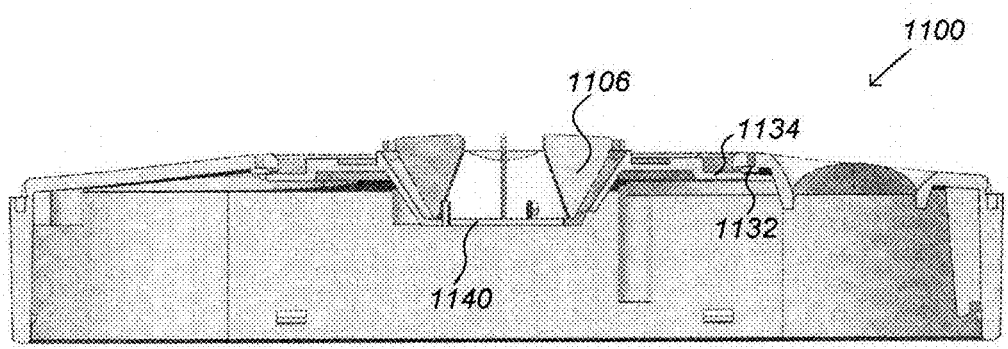

Referring now to FIGS. 11A-C, illustrated are front and rear perspective views of the front casing 1100. FIGS. 11D-F illustrate cross section views of front casing 1100 taken along a plane parallel to and passing through a central axis of the front casing and orthogonal to one of the sides of front casing 1100. As shown in FIGS. 11A-C, front casing 1100 includes a body portion or main body 1102 having a front surface and a plurality of sides arranged therearound that define a recessed region. As described herein, front casing 1100 is coupled with back plate 600 to define a housing of smoke chamber 400. The housing includes an interior region due to the recessed region of front casing 1100. The various components described herein that are positioned between the back plate 600 and front casing 1100 are contained within the interior region of the housing. As shown in the figures, front casing 1100 may comprise a roughly square configuration although other configurations (e.g., circular, oval, rectangular, and the like) are possible. In one embodiment, the square front casing 110 may be approximately 132 mm by 132 mm.

Referring now to FIGS. 11A-D, the body portion 1102 of front casing 1100 includes a central region within which the lens button 1200, light ring 1220, and flex ring 1240 are positioned. The central region includes a button portion 1106 that may be flexed axially inward relative to body portion 1102 as lens button 1200 is pressed inwardly 1142 by a user, such as to provide input to hazard detector 400. In one embodiment, the input to hazard detector 400 may be used to signal the hazard detector 400 to perform a desired action, such as for hushing an alarm or pre-alarm condition or for other reasons. Button portion 1106 includes a plurality of arms 1133 that are attached to an inner surface of an aperture region of front casing 1100. The arms 1133 are also attached respectively to a plurality of tabs 1134 that each extend radially outward from a circumferential edge of button portion 1106. The arms 1133 allow the button portion 1106 to be pressed axially inward relative to front casing 1100 while maintaining the tabs 1134 in a "loaded state" when the button portion 1106 is not pressed axially inward. The term "loaded state" means that the tabs 1134 are springably pressed axially outward against an inwardly facing surface 1132 of body portion 1102 when the button portion 1106 is not pressed axially inward. In some embodiments, the tabs 1134 may press axially outward against a ledge of the inwardly facing surface 1132. The arms 1133 also provide button portion 1106 and the components coupled therewith (e.g., lens button 1200, light ring 1220, and flex ring 1240) with rotational and positional stability by keeping the button portion 1106 centered relative to body portion 1102 and preventing button portion 1106 from rotating circumferentially relative to body portion 1102.

Maintaining the tabs 1134 in the loaded state in which the tabs 1134 are pressed axially outward against the inwardly facing surface 1132 of body portion 1102 allows the button portion 1106 to pivotably rotate about one or more points of contact 1136 between the tabs 1134 and the inwardly facing surface 1132 when the lens button 1200 is pressed substantially off-center or off-axis relative to a central axis of button portion 1106. FIG. 11D illustrates the button portion 1106 pivotably rotating about a point of contact 1136 between a tab 1134 and the inwardly facing surface 1132 as the lens button 1200 is pressed substantially off-axis (i.e., arrow 1142). Pressing the lens button 1200 and/or button portion 1106 substantially off-center or off-axis means that the respective component is pressed at a position radially away from an axis of the button portion 1106 that causes one side of the button portion 1106 to rotate while an opposite side of the button portion 1106 remains pressed axially outward against the inwardly facing surface 1132 of body portion 1102. In some embodiments, the lens button 1200 and/or button portion 1106 need not be pressed far from axis of button portion 1106 to cause the one sided rotation of button portion 1106 described above, although in other embodiments the lens button 1200 and/or button portion 1106 may need to be pressed relatively far from the axis of button portion 1106 to cause this rotation.

Pivot point(s) or points of contact 1136 are created by contact between one or more tabs 1134 and the inwardly facing surface or inner ledge(s) 1132 axially below which the tabs 1134 are positioned. The button portion 1106 pivots about these points of contact 1136 as the lens button 1200 is pressed off-center axially. Deflection of the button portion 1106 axially inward causes a bottom surface 1140 of the button portion 1106 to contact a switch 1138 positioned axially inward of the button portion 1106, which in turn provides a signal to circuit board 900. In this manner, a user may provide a button-press input to hazard detector 400. If the lens button 1200 is pressed roughly on-center relative to the central axis of button portion 1106, the arms 1133 allow the entire lens button 1200 and button pion 1106 to travel substantially downward axially so that no pivot point 1136 is created. Maintaining the tabs 1134 in the loaded state and creating the pivot point 1136 as described above allows the button (1200 and 1106) to have a substantially more consistent and stable button feel, regardless of the location of a downwardly applied force.

Referring now to FIGS. 11E-F, in some embodiments, the front casing 1100 and button portion 1106 may be formed as a single integral piece or component, thereby eliminating any issues arising from coupling separate components together as in conventional devices. The front casing 1100 and button portion 1106 may be formed (e.g., integrally molded) so that arms 1133 are "preloaded" or biased in an axially upward state or otherwise configured to bias the tabs 1134 axially upward against the inwardly facing surface 1132 of body portion 1102. As shown in FIG. 11E, front casing 1100 may be formed so that the arms 1133 hold or maintain the tabs 1134 in a first state in which the tabs 1134 are positioned axially outward relative to the inwardly facing surface or inner ledges 1132 of body portion 1102. In some embodiments, recesses or pockets may be formed above the inwardly facing surface 1132 within which the tabs 1134 reside when in the first state or when the front casing 1100 is initially formed. As shown in FIG. 11F, the arms 1133 may be flexed axially inward to reposition the button portion 1106 and tabs 1134 in a second state relative to body portion 1102 and the inwardly facing surface 1132. Repositioning the button portion 1106 and tabs 1134 to the second state involves positioning the tabs 1134 axially inward relative to the inwardly facing surface 1132. Since the arms 1133 are formed to hold or maintain the tabs 1134 in the first state axially outward of the inwardly facing surface 1132, repositioning the tabs 1134 so that the tabs 1134 are disposed axially inward of the inwardly facing surface 1132 stresses or loads the arms 1133 and causes the arms to load or press the tabs 1134 axially outward against a the inwardly facing surface or inner ledges 1132. In this manner, the pivot point or points of contact 1136 are created and the lens button 1200 and button portion 1106 are caused to rotate as the lens button 1200 and/or button portion 1106 are pressed axially off-center as previously described.

As shown by the arrows in FIG. 11E, the tabs 1134 may be repositioned from axially outward relative to inwardly facing surface 1132 to a position axially inward relative to inwardly facing surface 1132 by moving one tab 1134 angularly outward relative to body portion 1102 while simultaneously moving an opposite tab 1134 angularly inward relative to body portion 1102. The opposite tab 1134 (i.e., the tab moved angularly inward) may then be repositioned axially inward of and under the inwardly facing surface 1132. The front casing 1100 may then be rotated and opposing tabs 1134 moved angularly outward and angularly inward as described above to move a second tab 1134 under the inwardly facing surface 1132.

To reposition a tab 1134 under the inwardly facing surface 1132 when an opposing tab 1134 is already positioned under the inwardly facing surface, the entire button portion 1106 may be moved angularly inward relative to body portion 1102 so that the tab 1134 that is positioned axially outward of the inwardly facing surface 1132 may be so moved axially inward and repositioned under the inwardly facing surface 1132. In this manner each of the tabs 1134 may be repositioned from axially outward of the inwardly facing surface 1132 to axially inward of the inwardly facing surface.

Referring now to FIGS. 11A-C, button portion 1106 includes a plurality of posts 1123 that are configured to couple with light ring 1220 as described hereinbelow and further below with respect to FIGS. 12C-12D. Button portion 1106 also includes a plurality of axially outward extending flanges 1122 that correspond to similarly shaped flanges of flex ring 1240 and that facilitate in orienting and coupling the flex ring 1240 with button portion 1106. Button portion 1106 further includes an aperture 1120 through which a tail end or ribbon 1244 of flex ring 1240 is inserted to allow the tail end or ribbon 1244 of flex ring 1240 to be electrically coupled with circuit board 900.

Front casing 1100 also includes a first aperture 1108a and a second aperture 1108b through which the first ultrasonic sensor 972 and second ultrasonic sensor 974 are positioned. Stated differently, the first ultrasonic sensor 972 may be configured to be inserted partially or fully through the first aperture 1108a so that the first ultrasonic sensor 972 is able to view external object or individuals through front casing 1100. Likewise, the second ultrasonic sensor 974 may be configured to be inserted partially or fully through a second aperture 1108b so that the second sonic sensor 974 is able to view external objects or individuals through the front casing 1100. In some embodiments, the front surface of the first ultrasonic sensor 972 and/or second ultrasonic sensor 974 may be positioned in front of the front surface of front casing 1100 so that the front surface of the first ultrasonic sensor 972 and/or second ultrasonic sensor 974 is positioned essentially between the front casing 1100 and the cover plate 1300. In this arrangement, the first ultrasonic sensor 972 and/or second ultrasonic sensor 974 need only view external objects through the cover plate 1300 rather than viewing external objects through both cover plate 1300 and front casing 1100. An axis of first aperture 1108a may be directed substantially outward relative to front casing 1100 to allow the first ultrasonic sensor 972 to view objects substantially directly outward from hazard detector 400. An axis of second aperture 1108b may be angularly offset from the axis of first aperture 1108a to allow the second ultrasonic sensor 974 to view objects at an angle offset and downward relative to first aperture 1108a and hazard detector 400 as previously described. In some embodiments, the angular offset between the axis of first aperture 1108a and the axis of second aperture 1108b may be roughly 30°. In other embodiments the angular offset may be between about 15° and 45°, 20° and 40°, and the like.

Body portion 1102 of front casing 1100 further includes a plurality of openings 1104 that allow air to substantially freely flow to one or more internal components through the front casing 1100. Air flows through the plurality of openings 1104 in a relatively unimpeded manner, thereby increasing airflow to the internal components of hazard detector 400, such as smoke chamber 700. In this manner, detection of the presence of smoke or other conditions may be enhanced due to the increased air flow. In one embodiment, a collective area of the openings 1104 of front casing 1100 is between about 10% and about 60% of the area of front casing 1100's front surface. A collective area of between 10% and 60% is believed to increase airflow into the hazard detector 400 and/or into smoke chamber 700. In a specific embodiment, a collective area of the openings 1104 of front casing 1100 is at least 20% of the surface area of front casing 1100. A collective area of at least 20% of openings 1104 is likewise believed to greatly enhance airflow into hazard detector 400 and/or to one or more internal components positioned axially inward of front casing 1100, such as smoke chamber 700, CO detector, one or more microprocessors, and the like. In another embodiment, the collective area of openings 1104 of front casing 1100 is between about 10% and about 40% of the surface area of front casing 1100. Among other advantages, this collective area facilitates and/or optimizes airflow into hazard detector 400 and/or to the internal components.

In one embodiment, front casing 1100 is at least 2 millimeters thick and composed of a Polycarbonate (PC) and/or Acrylonitrile Butadiene Styrene (ABS) plastic material, such as those manufactured by LG Chem ltd. and sold under the tradename Lupoy® GP1006FM. In another embodiment, the front casing 1100 is composed of a ABS+PC plastic material, such as those manufactured by LG Chem ltd. and sold under the tradename Lupoy® GN5001RFH. The materials used in the front casing 1100 are typically flame rated V0 or higher to allow the front casing 1100, in view of the opening/hole pattern shown, to exhibit acceptable flame retardance despite having multiple openings or holes. In some embodiments, the diameter of each of the openings 1104 may be varied along the front surface of front casing 1100. The above described inventions and material of front casing 1100 allows the front casing to exhibit acceptable flame retardance despite having a plurality of holes and a relatively large portion of the front surface open.

Figure 11G:
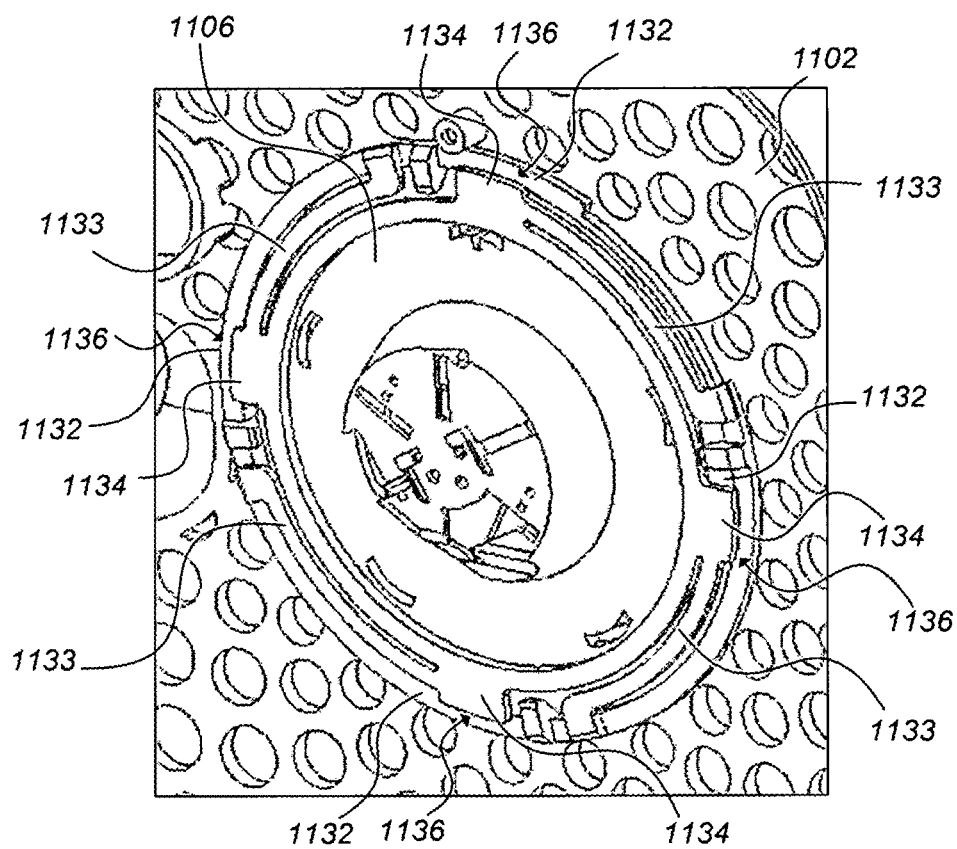

FIG. 11G illustrates a close up perspective view of the arrangement of the button portion 1106 and body portion 1102 of front casing 1100. Specifically, FIG. 11G illustrates the inwardly facing surface 1132 of body portion 1102 that is positioned opposite an outwardly facing surface (not shown) of body portion 1102 that faces a room within which the hazard detector 400 is positioned. The button portion 1106 is attached to the body portion 1102 via the plurality of arm 1133. FIG. 11G illustrates four arms 1133 coupling the button portion 1106 to the body portion 1102, although more or fewer arms 1133 may be used. As described above, the arms 1133, button portion 1106, and body portion 1102 may be formed as a single component, such as by molding the components together. The arms 1133 allow the button portion 1106 to be axially movable relative to the body portion 1102 such as to activate the switch 1138 positioned axially behind the button portion 1106. The arms 1133 also rotation and positionally stabilize the button portion 1106 relative to body portion 1102 as described above.

The tabs 1134 extend radially outward from a peripheral edge of the button portion 1106. FIG. 11G illustrates the button portion 1106 including four tabs 1134, although more or fewer tabs 1134 may be used as desired. Each tab 1134 is positioned under and contacts the inwardly facing surface 1132 of the body portion 1102 such that when a force is applied to the button portion 1106, or a lens button 1200 coupled therewith, at a position substantially offset from a central axis of the button portion 1106, the button portion 1106 pivots about one or more contact points 1136 between the tabs 1134 and the inwardly facing surface 1132 of the body portion 1102. As described above, the arms 1133 are coupled with the button portion 1106 and the body portion 1102 in a manner that biases the button portion 1106 axially outward relative to the body portion 1102. This causes the tabs 1134 to press against the inwardly facing surface 1132 of the body portion 1102 and creates the contact points 1136.

As shown in FIG. 11G, each of the arms 1133 includes a proximal end and a distal end with a main body extending therebetween. Each arm 1133 is fixed to the body portion 1102 at the proximal end and fixed to the button portion 1106 at the distal end. The main body of each arm 1133 extends circumferentially around a portion of the button portion 1106. The distal end of each arm 1103 is coupled with a tab 1134 of the button portion 1106. The button portion 1106 is positioned substantially centrally relative to the body portion 1102.

Figure 11H:
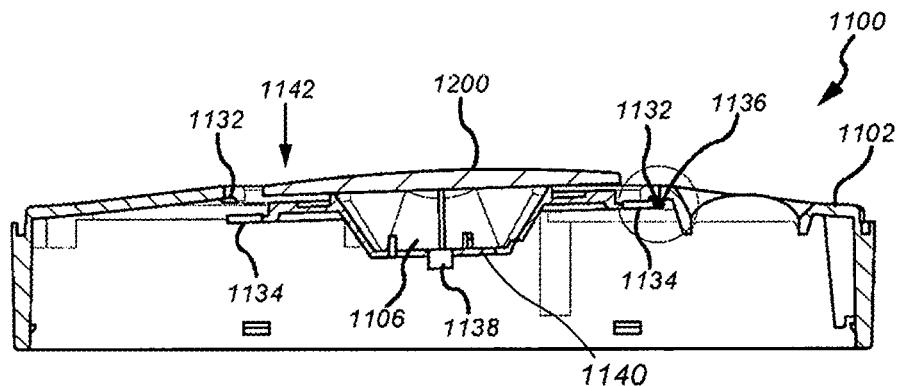
Figure 11I:
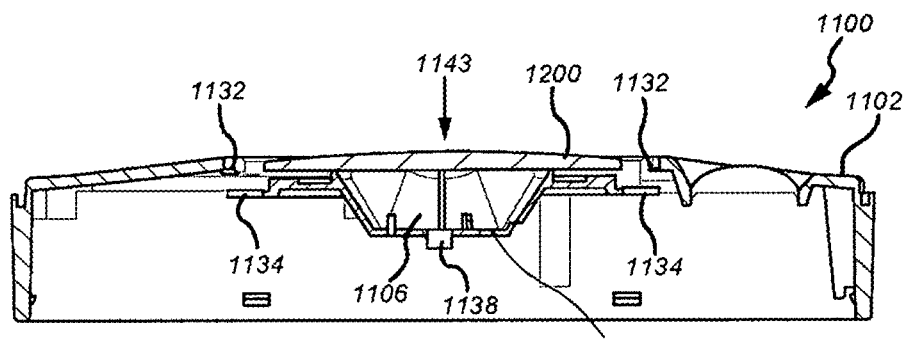
Figure 11J:
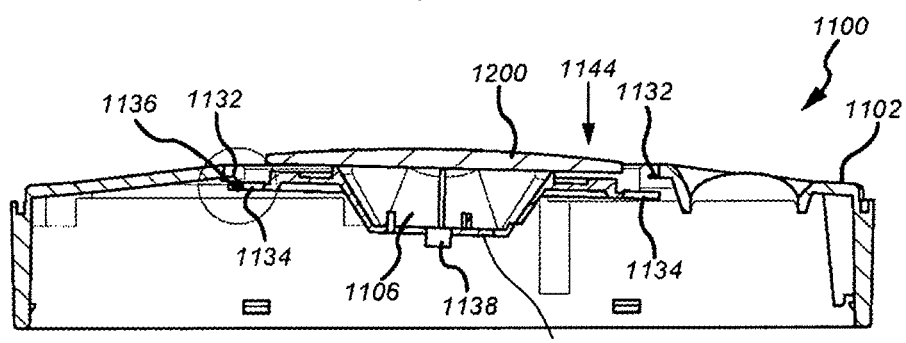

FIGS. 11H-J illustrate the movement and/or rotation of the button portion 1106 and lens button 1200 as they are pressed by a user. Specifically, FIG. 11H shows the lens button 1200 being pressed 1142 axially inward on a left edge portion of the lens button 1200, or in other words, substantially off-axis from the axis of button portion 1106. Pressing on the left edge portion of the lens button 1200 causes one or more tabs 1134 positioned on or near the right edge of the button portion 1106 to contact 1136 the inwardly facing surface 1132 of the body portion 1102 (i.e., shown in the circle area). The lens button 1200 and button portion 1106 pivot about the contact point 1136 between the tab(s) 1134 and the inwardly facing surface 1132, which causes the button portion 1106 to move axially inward and rotate relative to body portion 1102 and contact switch 1138 positioned axially inward of the button portion 1106. Preferably, the relatively small contact switch 1138 is selected to be of a kind that provides an appreciably loud and appreciably stiffly reboundable clicking action when in its depressed, so that a tactile and audible click feedback can carry back to the user through the various plastic and springable elements that form the button function. As described previously, the arms (not shown in FIGS. 11H-J) bias the button portion 1106 axially outward relative to body portion 1102 so that in a non-pressed condition, the tabs 1134 are pressed axially outward against the inwardly facing surface 1132 of body portion 1102. Thus, when the user stops pressing 1142 the left edge of lens button 1200, the left edge of lens button 1200 and button portion 1106 will rotate outward so that all of the tabs 1134 press axially outward against the inwardly facing surface 1132.

FIG. 11I shows the lens button 1200 being pressed 1143 axially inward on or near the axis of button portion 1106. Pressing "on-axis" of the lens button 1200 and button portion 1106 essentially causes the entire button portion 1106 to move axially inward such that none of the tabs 1134, or very few tabs, contact the inwardly facing surface 1132 of the body portion 1102. In such instances, the lens button 1200 and button portion 1106 do not pivot about any contact point 1136 between the tabs 1134 and the inwardly facing surface 1132. The button portion 1106 still moves axially inward relative to the body portion 1102 to contact switch 1138 positioned axially inward of the button portion 1106. The arms (not shown) bias the button portion 1106 axially outward relative to body portion 1102 so that in a non-pressed condition, the tabs 1134 are pressed axially outward against the inwardly facing surface 1132 of body portion 1102. Thus, when the user stops pressing 1143 on or near the center of lens button 1200, the lens button 1200 and button portion 1106 move axially outward so that all of the tabs 1134 press axially outward against the inwardly facing surface 1132.

FIG. 11J shows the lens button 1200 being pressed 1144 axially inward on a right edge portion of the lens button 1200, or in other words, substantially off-axis from the axis of button portion 1106. Pressing on the right edge portion of the lens button 1200 causes one or more tabs 1134 positioned on or near the left edge of the button portion 1106 to contact 1136 the inwardly facing surface 1132 of body portion 1102 (i.e., shown in the circle area). The lens button 1200 and button portion 1106 pivot about the contact point 1136 between the tab(s) 1134 and the inwardly facing surface 1132, which causes the button portion 1106 to move axially inward and rotate relative to body portion 1102 and contact switch 1138 positioned axially inward of the button portion 1106. The arms (not shown) bias the button portion 1106 axially outward relative to body portion 1102 so that in a non-pressed condition, the tabs 1134 are pressed axially outward against the inwardly facing surface 1132 of body portion 1102. Thus, when the user stops pressing 1144 the right edge of lens button 1200, the right edge of lens button

1200 and button portion 1106 rotates outward so that all of the tabs 1134 press axially outward against the inwardly facing surface 1132.

The configurations of FIGS. 11A-J provide a satisfying springable "click" button feel for enhancing the user experience, the button being relatively easy to press but having enough tactile and audible feedback so that the users recognize when the action has been performed, such as when the button portion 1106 contacts switch 1138. For example, the user may feel the button portion 1106 move axially inward and contact the switch 1138 and thus recognize that input has been provided to the hazard detector 400.

Figure 16:
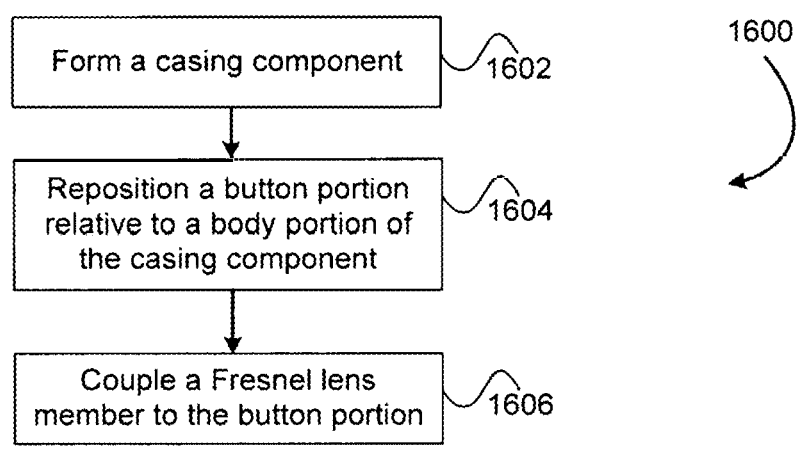
FIG. 16 illustrates a method of making a casing having a pressable button portion, according to an embodiment.

Referring now to FIG. 16, illustrated is a method 1600 of making a casing having a pressable button portion. At block 1602, a casing component is formed. The casing component includes a body portion, a button portion, and a plurality of arms that attach the button portion to the body portion. The body portion includes an outwardly facing surface and an inwardly facing surface opposite the outwardly facing surface. The button portion includes a plurality of tabs that extend radially outward from a peripheral edge of the button portion. The plurality of arms attach the button portion to the body portion with the plurality of tabs being positioned axially outward relative to the inwardly facing surface of the body portion. The plurality of arms allows the button portion to be movable relative to the body portion. At block 1604, the button portion is repositioned relative to the body portion so that the plurality of tabs are positioned axially inward of the inwardly facing surface of the body portion. Repositioning the button portion in this manner causes the plurality of arms to bias the button portion axially outward relative to the body portion so that the plurality of tabs press against the inwardly facing surface of the body portion.

Contact between the plurality of tabs and the inwardly facing surface of the body portion causes the button portion to pivot relative to the body portion when a force is applied to the button portion substantially off-axis from a central axis of the button portion. In some embodiments, the body portion, button portion, and the plurality of arms are integrally molded as a single component. In some embodiments, a Fresnel lens member may be coupled to the button portion (block 1606). The Fresnel lens member may function as a pressable button and as a lens for a passive infrared (PIR) sensor positioned axially inward of the Fresnel lens member.

A similar method of making a casing having a pressable button portion may include forming a casing component having a body portion and a button portion. The casing component may be formed such that one or more tabs that extend radially outward from a peripheral edge of the button portion are positioned axially outward relative to an inwardly facing surface of the body portion. The method may also include repositioning the button portion relative to the body portion such that the one or more tabs of the button portion are positioned axially inward of the inwardly facing surface of the body portion. Repositioning the button portion relative to the body portion in this manner causes the one or more tabs to be biased radially outwardly against the inwardly facing surface of the body portion.

In some embodiments, the method may further include coupling a Fresnel lens member to the button portion. The Fresnel lens member may function as a pressable button and as a lens for a passive infrared (PIR) sensor positioned axially inward of the Fresnel lens member. The body portion and the button portion may be integrally molded as a single component.

As described herein, the front casing 1100 may be formed (e.g., molded) so that the button portion 1106 is an integrally connected to the body portion 1102. Forming these components as a single piece may increase manufacturing and assembly efficiency. Other components of the hazard detector 400 may likewise be formed to increase some form of efficiency. For example, in some embodiments, the front casing 100 and/or cover plate 1300 may be formed with perforated surfaces instead of holes so that a user may punch holes into the front casing 1100 and/or cover plate 1300 after the hazard detector 400 is purchased and/or mounted to a wall or ceiling. In this manner, the pattern and/or sizing of the holes may be varied as desired from front casing 1100 and/or cover plate 1300 stock components. Stated differently, the perforated front casing 1100 and/or cover plate 1300 may be stock components that provide configurable hole patterns and/or hole sizing as desired.

Similarly, the protective plate 800 that is coupled with the circuit board 900 may have trimmable edges that allow a stock protective plate component to be manufactured and easily trimmed to size depending on the size of the hazard detector 400 for which the protective plate 800 will be used. In one embodiment, the protective plate 800 may have perforated regions that allow various holes, slots, apertures, and the like to be formed in the protective plate 800, such as for mid-mounting of various hazard detector components.

The cover plate 1300, mounting plate 500, and/or back plate 600 may likewise have trimmable edges that allow the dimensions of these components to be adjusted as desired. These components may also have perforated regions or portions that allow various holes, slots, apertures, and the like to be formed in these components so as to create air vents, decorative hole pattern designs, and the like. In this manner the component count that is required to produce a variety of shaped and sized hazard detectors may be greatly reduced.

Figure 12A:
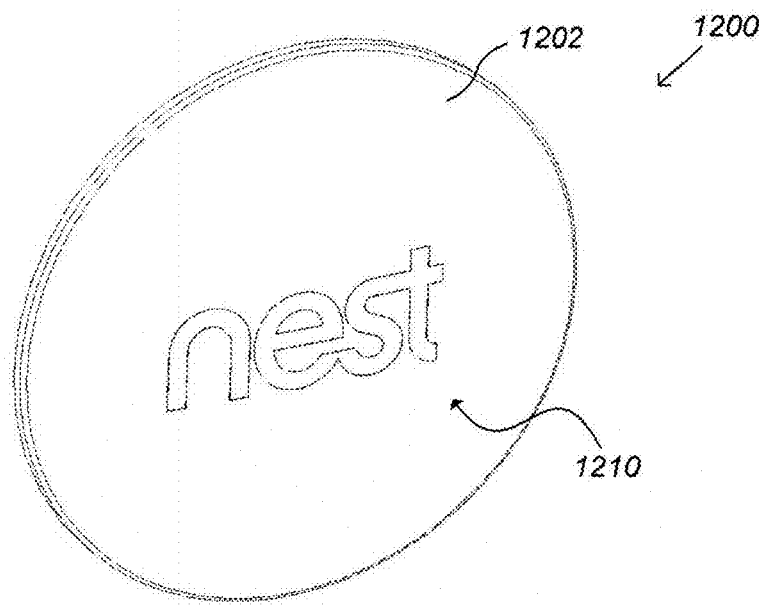
FIGS. 12A-B illustrate front and rear perspective views of a lens button of the hazard detector of FIGS. 4A-F, according to an embodiment.
Figure 12B:
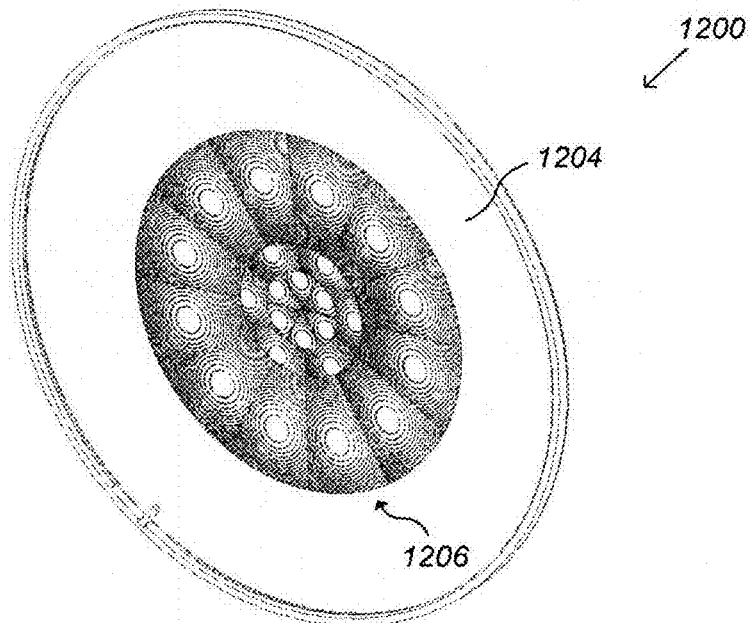

Referring now to FIGS. 12A and 12B, illustrated are front and rear perspective views of a button cap component 1200 (hereinafter lens button 1200). Lens button 1200 includes a front surface 1202 that faces a room in which the hazard detector 400 is positioned and a rear surface 1204 that is opposite the front surface. Lens button 1200 is configured to be coupled with front casing 1100, and specifically the button portion 1106 of front casing 1100, by attaching lens button 1200 to light ring 1220, and coupling light ring 1220 to the button portion 1106 of front casing 1100. In some embodiments, lens button 1200 may be coupled directly to the button portion 1106 without being coupled to the light ring 1220.

Lens button 1200 provides a visually appealing surface that may be pressed by a user to provide input to hazard detector 400 and/or for various other purposes, such as quieting an alarm device. Pressing lens button 1200 effectuates axial movement of the button portion 1106 of the front casing 1100, which causes the button portion 1106 to contact a switch positioned behind the button portion 1106 so that input may be provided to the hazard detector by an occupant. Lens button 1200 is further configured to be transparent to one or more sensors positioned behind lens button 1200. For example, in one embodiment, a PIR sensor is positioned behind lens button 1200. The PIR sensor is able to view external objects through lens button 1200 to determine if an occupant is present within a room in which hazard detector 400 is positioned.

The rear surface 1204 of lens button 1200 may have a Fresnel lensing component or element 1206 (hereinafter Fresnel lens element 1206) integrally formed thereon that allows one or more PIR sensors, or another sensor (e.g., CCD camera), positioned behind lens button 1200 to view far into the room in which hazard detector 400 is positioned. Lens button 1200 is typically positioned axially in front of the PIR or other sensor(s) to direct infrared radiation onto the sensor device. Further, the Fresnel lens element 1206 is formed on the rear surface 1204 of lens button 1200 so as to be hidden from external view. Lens button 1200 provides a visually pleasing contour that may match a contour of the exterior of cover plate 1300 so that when coupled with cover plate 1300, lens button 1200 and cover plate 1300 have a visually continuous contour. Similarly, the Fresnel lens element 1206 may be contour-matched to a contour of the rear surface 1204 of lens button 1200. The Fresnel lens element 1206 may be made from a high-density polyethylene (HDPE) that has an infrared transmission range appropriate for sensitivity to human bodies.

In one embodiment, Fresnel lens element 1206 may include a plurality of concentrically arranged rings that each include a plurality of lenslets and that each provide a slightly different viewing cone. Each concentrically arranged ring may provide a progressively larger viewing area or cone than a concentrically arranged located radially closer to a central axis of lens button 1200. In one embodiment, an internal angle of the viewing cones provided by Fresnel lens element 1206 may vary from between about 15° and about 150° so as to provide a viewing radius on a floor or wall positioned directly in front of the hazard detector 400 at a distance of approximately 10 feet of between about 0.5 m and about 8.8 m. In this manner, the PIR sensor, or other sensor, positioned behind lens button 1200 may easily detect the presence of an occupant within a room in which hazard detector 400 is positioned.

Figure 12C:
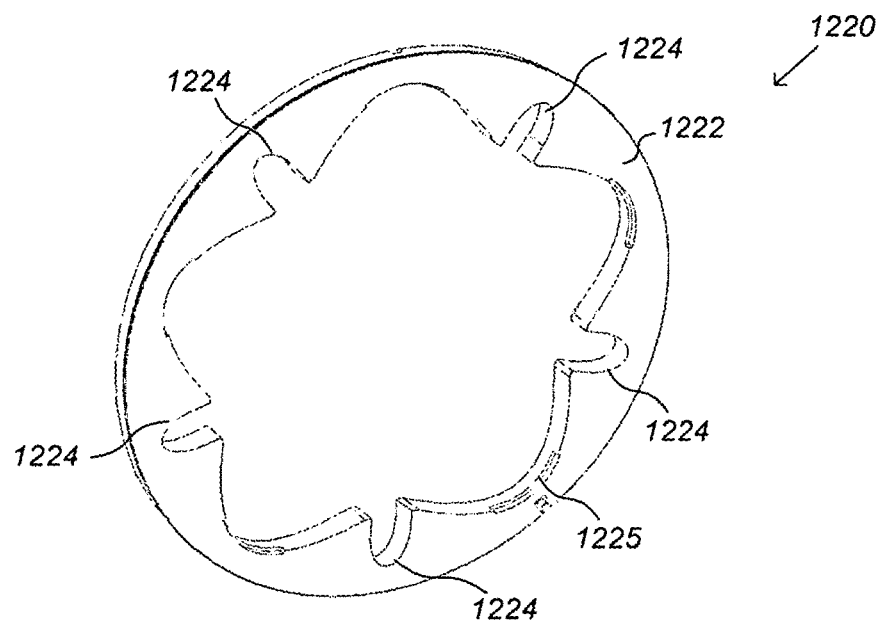
FIGS. 12C-D illustrate front and rear perspective views of a light guide of the hazard detector of FIGS. 4A-F, according to an embodiment.
Figure 12D:
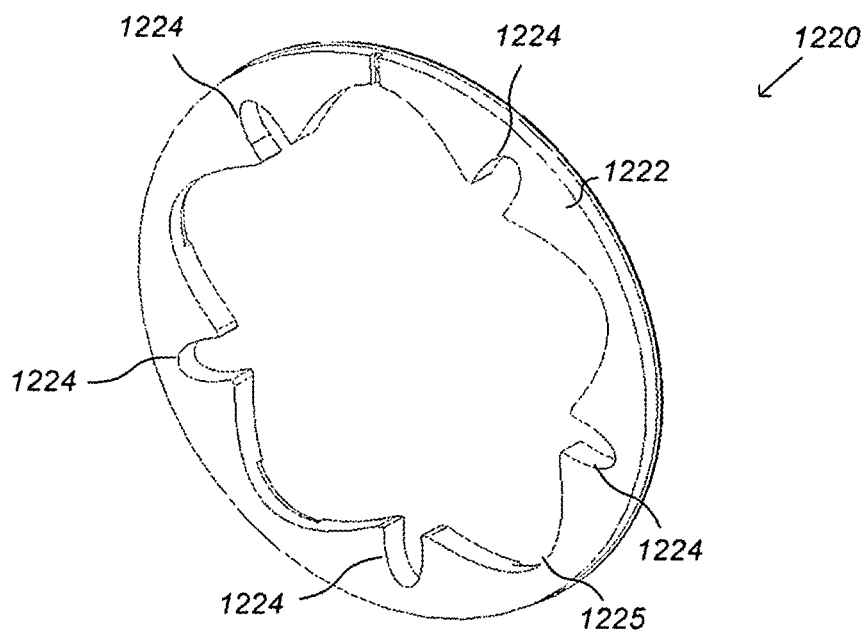
Figure 12E:
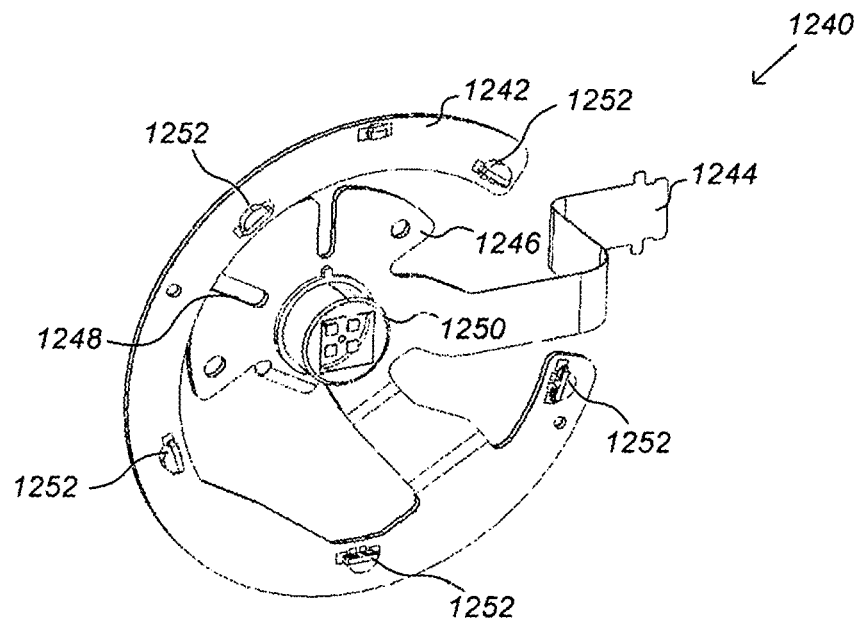
FIGS. 12E-F illustrate front and rear perspective views of a flexible strip of the hazard detector of FIGS. 4A-F, according to an embodiment.
Figure 12F:
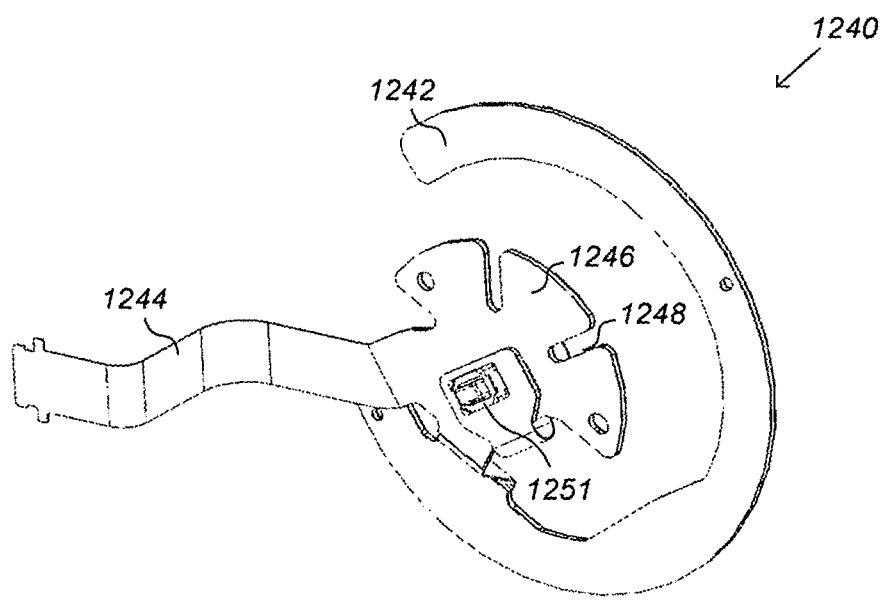
Figure 12G:
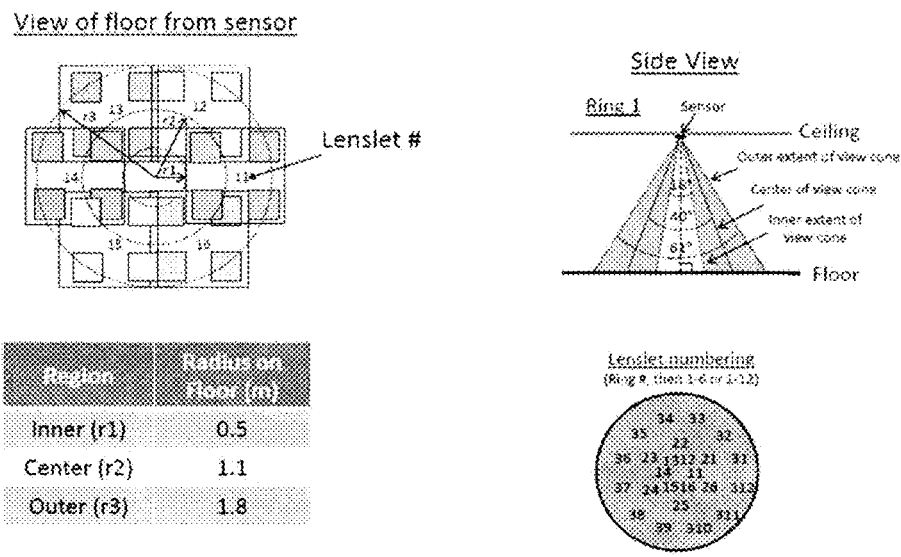
FIGS. 12G-J illustrate aspects of a Fresnel lens element of the lens button of FIGS. 12A-B, according to an embodiment.
Figure 12H:
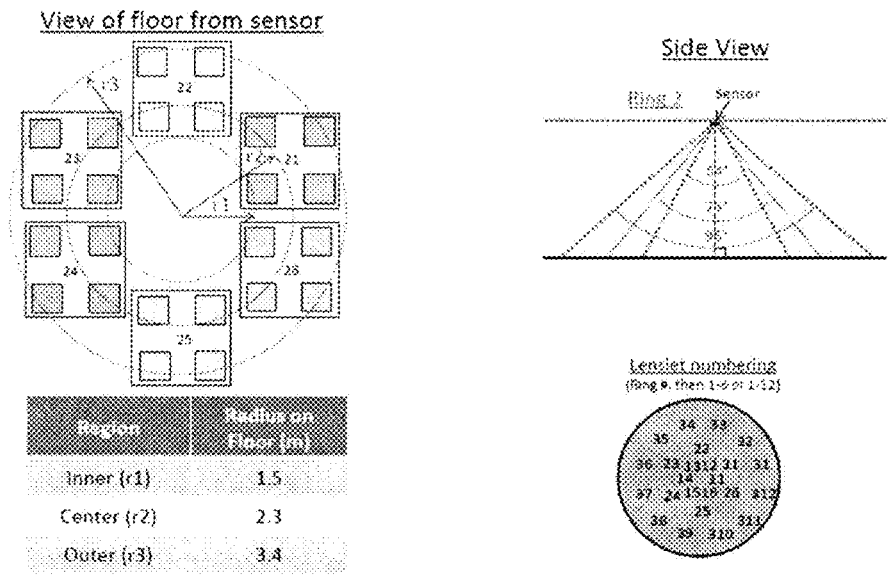
Figure 12I:
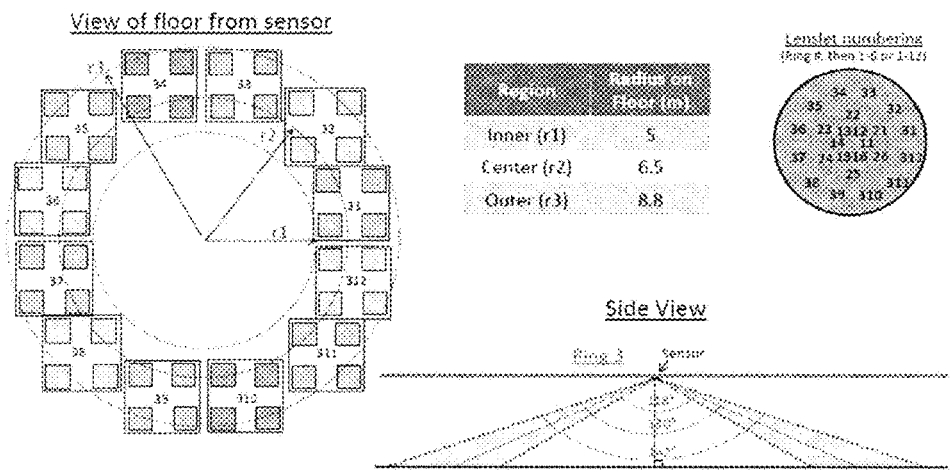
Figure 12J:
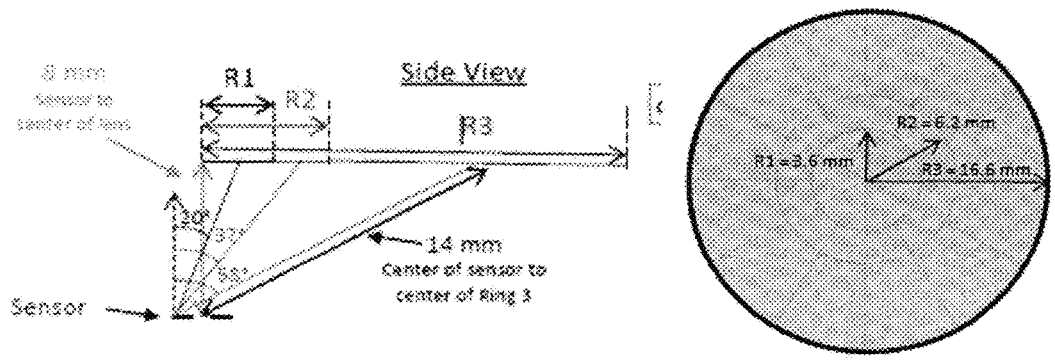

Referring now to FIGS. 12G-I, according to one embodiment, the Fresnel lens element 1206 may include 3 concentrically arranged rings that each include a plurality of lenslets. Each of the lenslets is a separate Fresnel lens. Each lenslet should be designed based on a location and orientation in the detector with respect to the PIR sensor(s) 150, as well as depending on the monitoring area desired to be viewable by the PIR sensor(s) via the lenslet. In selecting the number of lenslets, there is a tradeoff between light collection and size of each zone. It has been found the described Fresnel lens element 1206 is suitable for a wide-range of applications, although other numbers and sizes of lenslets can be used.

According to one embodiment, the Fresnel lens element 1206 may have a radius of curvature of between about 150 and 350 mm. A greater radius of curvature may be better because it typically provide a smaller incident light angle, which may reduce light loss. Greater radius of curvature, however, may be more difficult to produce. The described range of 150 to 350 mm has been found to provide an ideal amount of light loss and manufacturability. In other embodiments, the Fresnel lens element 1206 may have a radius of curvature of between about 200 and 300 mm, or about 250 mm, which provide even greater light loss and manufacturability aspects. According to one embodiment, the Fresnel lens element 1206 may provide a total of 24 lenslets that each view a different portion of the room in which the device is located. The 24 lenslets may focus infrared light from various directions onto the PIR sensor so that the sensor is able to detect the heat of an individual or object within the room and/or passing the hazard detector 400.

As shown in FIG. 12G, a first or inner ring may include 6 lenslets (i.e., 11, 12, 13, 14, 15, and 16) that provide viewing cones having internal angles of roughly 18°, 40°, and 61° respectively. The viewing cones provide a viewing radius on a floor or wall positioned approximately 10 feet in front of the hazard detector 400 of approximately 0.5 m (meters), 1.1 m, and 1.8 m respectively. As shown in FIG. 2J, the first or inner ring may have a radius of between about 3 and 4 mm from a central axis of the Fresnel lens element 1206, and more commonly have a radius of about 3.6 mm from the central axis. A center of the first or inner ring, which corresponds to a center of Fresnel lens element 1206 and lens button 1200, may be positioned between 1 and 30 mm axially above the PIR sensor. The spacing of the PIR sensor and lens depends on the number of lenslets used, the field of view desired, the size of the lens, and the like. In another embodiment, the center of the first or inner ring may be positioned between 5 and 15 mm axially above the PIR sensor. This spacing has been demonstrated to provide a good viewing coverage range while maintaining a relatively compact hazard detector profile. In one embodiment, the center of the first or inner ring may be positioned about 8 mm axially above the PIR sensor, which has been demonstrated to provide an optimal sensor coverage area and compact detector size. An angle measured from the central axis of the Fresnel lens element 1206 to a central portion of the first or inner ring may be about 20°.

As shown in FIG. 12H, a second or middle ring may also include 6 lenslets (i.e., 21, 22, 23, 24, 25, and 26) that provide viewing cones having internal angles of roughly 54°, 75°, and 96° respectively. The viewing cones provide a viewing radius on the floor or wall positioned approximately 10 feet in front of the hazard detector 400 of approximately 1.5 m, 2.3 m, and 3.4 m respectively. As shown in FIG. 2J, the second or middle ring may have a radius of between about 5 and 7 mm from the central axis of the Fresnel lens element 1206, and more commonly have a radius of about 6.2 mm from the central axis. An angle measured from the central axis of the Fresnel lens element 1206 to the central portion of the second or middle ring may be about 37°.

As shown in FIG. 12I, a third or outer ring may include 12 lenslets (i.e., 31, 32, 33, 34, 35, 36, 37, 38, 39, 310, 311, and 312) that provide viewing cones having internal angles of roughly 118°, 130°, and 142° respectively. The viewing cones provide a viewing radius on the floor or wall positioned approximately 10 feet in front of the hazard detector 400 of approximately 5 m, 6.5 m, and 8.8 m respectively. As shown in FIG. 2J, the third or outer ring may have a radius of between about 14 and 18 mm from a central axis of the Fresnel lens element 1206, and more commonly have a radius of about 16.6 mm from the central axis. A central portion of the third or outer ring may be between 12 and 16 mm measured diagonally at a 58° angle from the PIR sensor. In one embodiment, the center of the third or outer ring may be about 14 mm measured diagonally at the 58° angle from the PIR sensor. The 58° angle may correspond to an angle measured from the central axis of the Fresnel lens element 1206 to the central portion of the third or outer ring. In some embodiments, the effective focal length of each lenslet and/or placement of the focal center points of each lenslet may be designed so as to compensate for the lenslets being on a spherical or contoured surface so that the Fresnel lens element 1206 can match the contour of the cover plate 1300 and/or hazard detector 400. In some embodiments, the lens button 1200 may be opaque so as to hide one or more sensors and/or components positioned behind the lens button 1200.

As shown in FIG. 12A, a front surface of lens button 1200 includes indicia 1210, such as a logo, wording, lettering, or any combination thereof. The indicia 1210 is transparent to the one or more sensors and/or components positioned behind the lens button 1200 so as to not interfere with light or other signals that are detected by the sensors and/or components. When coupled with the hazard detector 400 and/or cover plate 1300, the indicia 1210 of lens button 1200 provides an orientation control by identifying a proper orientation of the hazard detector 400 about a wall or ceiling. For example, with reference to FIG. 4C, when the lens button 1200 is coupled with the hazard detector 400, a user will instantly recognize a proper orientation of the hazard detector 400 about a wall or ceiling since misorientation of the hazard detector 400 will result in the indicia 1210 (e.g., logo, wording, lettering, and the like) appearing incorrect, such as upside down, sideways, and the like about a wall or ceiling.

The inherent orientation capability provided by the indicia 1210 saves the user time and effort in correctly positioning and mounting the hazard detector about a wall, since the user is able to instantly recognize the correct orientation without having to rely on installation instructions. As described previously, the hazard detector 400 should be positioned and mounted to a wall so that the second ultrasonic sensor 974 essentially looks downward toward the floor. The indicia 1210 is aligned with the second ultrasonic sensor 974 so that when the indicia appears correct (i.e., the wording, logo, lettering, and the like are properly and logically oriented), the second ultrasonic sensor 974 is properly oriented to look downward toward the floor. As such, the indicia 1210 facilitates proper positioning of the hazard detector 400 upon installation such that proper operation is achieved with respect to the sensing of one or more features of the surrounding environment in which the hazard detector is installed. Although the indicia 1210 are particularly advantageous for achieving proper device alignment for facilitating ultrasonic sensing of the movements of a room occupant, which can in turn be beneficial for sensing certain human-to-device signaling or communications capabilities such as the gesture hush or wave hush capability disclosed in U.S. 61/847,906, supra, it is to be appreciated that the scope of the various advantages that can be facilitated or achieved by proper alignment of the hazard detector 400 by virtue of the indicia 1210, which at the same time preserves or promotes the visually pleasing qualities of the hazard detector, is not so limited.

Referring now to FIGS. 12C and 12D, illustrated are front and rear perspective views of a light ring 1220 that may be used to disperse light provided by an LED or other light source so as to provide a halo effect behind and around lens button 1200. Light ring 1220 includes a body portion 1222 and may be coupled with lens button 1200 via adhesive bonding, one or more fasteners, or any other method known in the art. In turn, light ring 1220 may be coupled with front casing 1100 such as by orienting light ring 1220 with respect to button portion 1106 of front casing 1100 and pressing light ring 1220 axially downward relative to front casing 1100 so that recessed portions 1225 of light ring 1220 mate and couple with posts 1123 of front casing 1100. Posts 1123 may fit over the recessed portions 1225 of light ring 1220 and secure light ring 1220 adjacent button portion 1106. Light ring 1220 also includes a plurality of second recesses 1224 within which LEDs (not shown) or other light sources or light conductors may be positioned to illuminate light ring 1220. In operation, light ring 1220 disperses light provided by the LEDs, or other light sources, circumferentially around the lens button 1200 to produce a halo light effect behind and around lens button 1200.

Referring now to FIGS. 12E and 12F, illustrated are front and rear perspective views of a flexible circuit board or flex ring 1240 that may electrically couple components positioned in front of circuit board 900, such as lens button 1200, with circuit board 900. Flex ring 1240 includes a tail end or ribbon 1244 that is insertable into a component of circuit board 900 to electrically couple lens button 1200, light ring 1220, and/or one or more components with circuit board 900. Flex ring 1240 also includes a central portion that may include a PIR sensor 1250 that is positioned so as to be axially behind lens button 1200. The PIR sensor 1250 faces a room within which the hazard detector 400 is positioned. As discussed herein, the PIR sensor 1250 has a field of view into the room such that objects or individuals present in the room and within the field of view are detectable by the PIR sensor 1250. The PIR sensor 1250 is also communicatively coupled with circuit board 900 to provide information thereto and/or receive information therefrom.

The central portion of flex ring 1240 further includes a plurality of flanges 1246 that mate with the flanges 1122 of front casing 1100 so as to properly orient flex ring 1240 relative to front casing 1100 and/or couple flex ring 1240 therewith. Specifically, a channel 1248 between flanges 1246 may fit around flange 1122 of front casing 1100 to orient and couple flex ring 1240 with front casing 1100. Flex ring 1240 further includes a circumferentially arranged ring portion 1242 having a plurality of LED lights 1252, or other source of light or an end of a light conduit, coupled therewith. The plurality of LED lights 1252 are arranged so as to be insertable within recessed portions 1224 of light ring 1220. LED lights 1252 illuminate light ring 1220 to disperse light circumferentially around lens button 1200 and produce the spatially, temporally, or spatiotemporally modulated halo light effects previously described hereinabove. A bottom surface of the central portion of flex ring 1240 includes a contact switch 1251, which corresponds to the contact switch 1138 of FIGS. 11A-11J, supra, that is actuated as lens button 1200 is pressed by a user. In this manner, input is provided to the hazard detector 400 by the user as previously described.

In some embodiments, components in addition to or instead of the PIR sensor 1250 may be positioned behind the lens button 1200. For example, in one embodiment a microphone (not shown) may be positioned behind the lens button 1200 or elsewhere on the hazard detector 400. The microphone can be operated to listen to noises that occur within the room in which the hazard detector 400 is positioned. In a specific embodiment, the microphone can be activated and the noise transmitted to another room for various purposes, such as monitoring the activity level of a newborn child or determining if an intruder has entered the home.

In another embodiment, the color of the light ring 1220 positioned behind axially the lens button 1200 may be adjusted to provide information or messages to an occupant of the home or structure. For example, the light ring 1220 of the hazard detector 400 in a parent's room can be adjusted to glow red if the PIR sensor 1250 of another hazard detector 400 located in a child's room fails to detect the presence of the child. Similarly, the light ring 1220 may glow yellow and/or flash when the hazard detector 400 senses the presence of an individual (e.g., an intruder) entering a doorway of the home after a certain period of time (e.g., after 11:00 p.m.).

In another embodiment, the color of the light ring 1220 of the hazard detector 400 may be adjusted based on the time of year. For example, the produced halo light may glow orange around the thanksgiving holiday and may glow white each time snow fall occurs in the area. In another embodiment, the color of the light ring 1220 may be adjusted to indicate potential issues within the home, such as a malfunctioning appliance or other component. For example, a smart thermostat may detect an abnormality with the heating system of the home and relay this information to the hazard detector 400. The hazard detector 400 may flash red to indicate to the occupant that a potential issue has been detected and/or to warn the occupant to investigate the potential issue. An email or message may be sent to the occupant by one of the smart home devices (e.g., smart hazard detector 400, smart thermostat, and the like) to notify the occupant of the detected issue. In some embodiments, the light ring 1220 may flash a number of times, or change color, to indicate the room in which the potential abnormality was detected. For example, the hazard detector 400 could flash once for a first room (e.g., kitchen), twice for a second room (e.g., master bedroom), and the like.

In some embodiments, the PIR sensor 1250 may be replaced with an optical CCD sensor. In such embodiments, the Fresnel lens 1206 may be a true optical imaging lens for light in the visible spectrum. The CCD sensor may provide optical pictures and/or video of individuals and/or objects within the room and within the field of view of the CCD sensor. The lens 1206 may also serve as a user-pressable button. In other embodiments, the PIR sensor 1250, Fresnel lens 1206, and/or CCD sensor may be incorporated in any of a variety of different smart-home devices, such as security cameras, doorbells, garage door openers, entertainment devices, and so forth. Essentially, these components may be incorporated into any device where an occupancy detecting function of a PIR sensor and/or CCD sensor might be useful and where there is a need for a front selectable button.

Figure 13A:
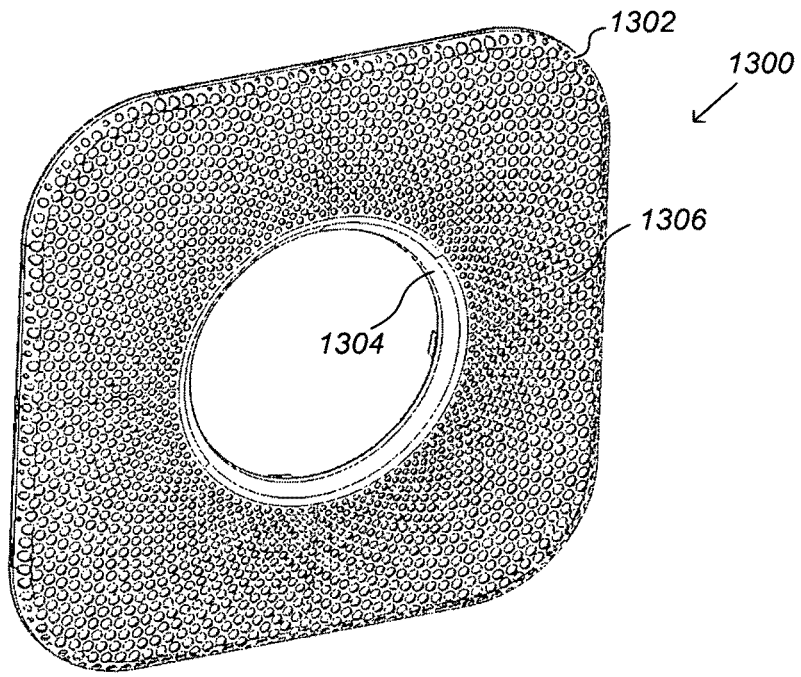
FIGS. 13A-B illustrate front and rear perspective views of a cover plate of the hazard detector of FIGS. 4A-F, according to an embodiment.
Figure 13B:
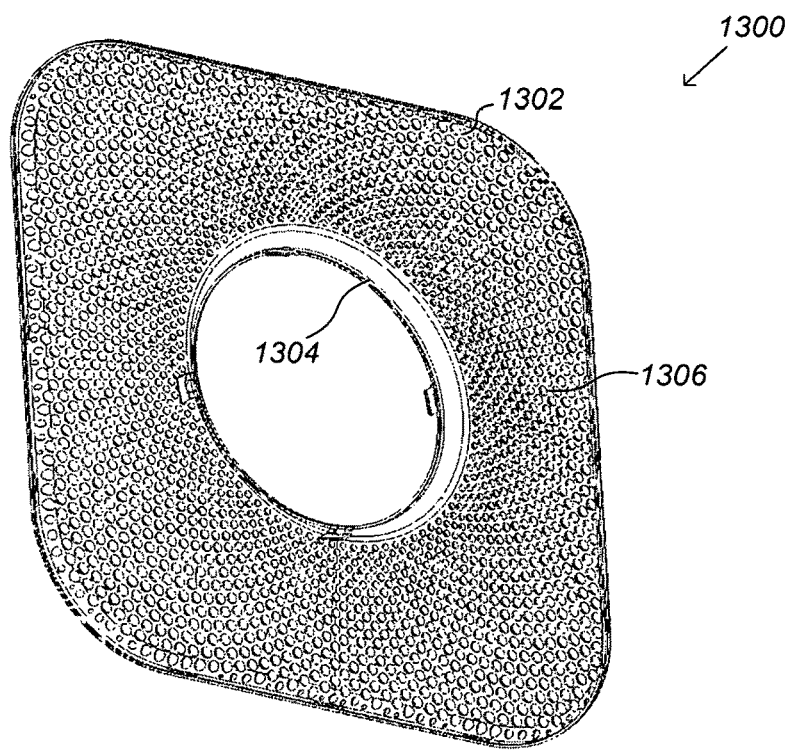

Referring now to FIGS. 13A and 13B, illustrated are front and rear perspective views of a cover plate 1300 that may be coupled with a front surface of front casing 1100. Cover plate 1300 is configured to face an occupant of a room in which hazard detector 400 is positioned. Cover plate 1300 includes a body portion 1302 having a plurality of openings 1306 that provide a visually pleasing appearance to an occupant of the room in which hazard detector 400 is positioned. The openings 1306 may be circular in shape and, in one embodiment, have a diameter of between about 1.25 and 2.5 millimeters. Openings 1306 may cover a relatively large portion of body 1302. In some embodiments, cover plate 1300 may comprise a square configuration having dimensions of approximately 134 mm by 134 mm. Cover plate 1300 may have a thickness of about or at least 0.5 mm and more commonly about 0.6 mm, although other thicknesses are possible. In one embodiment, the diameter of one or more openings 1306, or substantially all openings, may be about the same as a wall thickness or spacing between edges of adjacent openings 1306 of cover plate 1300. In another embodiment, the openings 1306 may be about twice the wall thickness between adjacent openings 1306.

In one embodiment, the size of the openings 1306 may be varied such that body 1302 comprises a plurality of different sized openings 1306. Similarly, the shape of openings 1306 may be varied so that configurations other than circular configurations are included (e.g., oval, square, rectangular, diamond, triangular, and the like). Body portion 1302 of cover plate 1300 also includes a centrally located aperture 1304 within which lens button 1200 and light ring 1220 are positioned.

As described previously, the ultrasonic sensors (i.e. 972 and 974) are positioned distally behind cover plate 1300. Openings 1306 are configured and dimensioned so that an occupant of the room in which hazard detector 400 is positioned is unable to see the internal components of hazard detector 400 behind cover plate 1300, such as ultrasonic sensors 972 and 974. Openings 1306 further allow air to flow substantially freely behind cover plate 1300 and to the one or more internal components positioned there behind. Air flows through the cover plate 1300 in a relatively unimpeded manner, such that air flow into the hazard detector 400 and/or to one or more internal components is substantially increased due to the openings 1306 of cover plate 1300. In addition, openings 1306 allow objects or individuals in front of cover plate 1300 to be viewable by the one or more sensors positioned behind cover plate 1300. For example, the ultrasonic sensors 972 and/or 974, or other sensors, position behind cover plate 1300 are capable of detecting objects and/or persons from behind the cover plate 1300. The sensors 972 and/or 974, however, are not viewable by occupants of the room in which the detector 400 is positioned.

As described herein, cover plate 1300 includes a relatively large population of relatively small openings 1306. For example, body 1302 may include 1000-2000 or more of such openings 1306. The number and spacing of openings 1306 depends on the diameter of the openings 1306 and/or the design or pattern of the openings 1306 used. In one embodiment, a collective area of the openings 1306 may be between about 20% and about 80% of the total surface area of cover plate 1300. In another embodiment, the collective area of the openings 1306 may be at least 30% of the total surface area of cover plate 1300. Even though the scope of the disclosure is not necessarily so limited, it has been found that a collective area of openings 1306 of at least 30% is beneficial because it provides good air flow through cover plate 1300 to the one or more components positioned there behind. In one embodiment, the collective area of openings 1306 may be at least 20% of the total surface area of cover plate 1300. A collective area of 20% of openings 1306 may not be as advantageous with respect to air flow as a collective area of 30%; however, the collective area of 20% may be more advantageous for hiding internal components of hazard detector 400 from view of occupants of the room, such as sensors 972 and 974.

In another embodiment, the collective area of openings 1306 may be at least 40% of the total surface area of cover plate 1300. In a further embodiment, the collective area of openings 1306 may be at least 50% of the total surface area of cover plate 1300. In still a further embodiment, the collective area of openings 1306 may be at least 60% of the total surface area of cover plate 1300. As briefly described above, the increasingly greater collective area of openings 1306 may be advantageous with respect to air flow through cover plate 1300, but may not be advantageous for hiding internal components of hazard detector 400 from view. Stated differently, for air flow purposes, a collective area of openings 1306 of 50% is generally better than a collective area 40%, while a collective area of 60% is generally better than a collective area of 50%. In contrast, for visibility of internal components purposes, a collective area of openings 1306 of 40% is generally better than a collective area of 50%, while a collective area 50% is generally better than a collective area of 60%. The collective area of openings 1306 used may depend on the internal components of the hazard detector, an intended distance of the hazard detector from an occupant, the function or purpose of the hazard detector, and the like.

The openings 1306 may be arranged with respect to body 1302 according to a repeating pattern. For example, in one embodiment the openings 1306 are arranged with respect to body 1302 according to a Fibonacci sequence. Such arrangement provides a visually pleasing appearance to occupants of the room in which hazard detector 400 is present, thereby allowing hazard detector 400 to be visually attractive and/or appear as a decorative object rather than appearing as a component of an appliance as with many conventional smoke detectors, carbon monoxide detectors, and other hazard detectors. For some embodiments, the arrangement of openings 1306 and the pattern provided thereby may be designed so as to produce any desired visual effect. For example, the openings 1306 may be arranged so as to appear as an animal, a famous landmark, a trademark or brand image (e.g. NFL franchise logo and the like), and the like. In some embodiments, the arrangement of openings 1306 may be custom designed by occupant of the home or structure in which the hazard detector will reside.

The openings 1306 in the cover plate 1300 and/or front casing 1100 may allow the hazard detector 400 to be used for additional purposes. For example, in one embodiment, LED lights (not shown) can be mounted on or otherwise coupled with the front casing 1100 and behind the cover plate 1300. The LED lights can be illuminated so as to be visible to occupants within the room or area in which the hazard detector 400 is located. The LED lights may functions as part of a warning or alarm mechanism to alert the occupant to a possible danger. Such a feature may be highly desirable for individuals that are hearing disabled or that have hearing disable friends or relatives or otherwise anticipate hearing disabled visitors within the home or structure. The LED lights may not be visible to the occupants until or unless the LED lights are illuminated.

In some embodiments, instructions may be visually displayed through the cover plate 1300 via LED lights, or an LCD panel, mounted behind the cover plate 1300. For example, the LED lights could be used in combination with the speaker 950 of the hazard detector 400 to help occupants of the home or structure safely exit the structure. The speaker 950 may alert the occupant to proceed to an exit indicated by an arrow that is displayed through the cover plate 1300 via the LED lights (e.g., flashing or static display). When a home or building includes multiple hazard detectors 400, information may be passed to each of the hazard detectors 400, or the hazard detectors 400 may be controlled via a central control, so that each of the hazard detectors 400 displays an arrow that directs occupants to safely exit the building or home. The arrows displayed may be controlled so as to lead the occupants away from a source of the alarm, such as a fire, or away from areas of high CO concentration and the like.

In a similar manner, the LEDs may lead firefighters or other rescuers to the source of the alarm, such as the source of the fire. Likewise, when a PIR sensor, ultrasonic sensor, or another sensor, detects the presence of an occupant in the home or structure, the LEDs behind cover plate 1300 may visually display the number of occupants that remain in the home or structure to a firefighter or rescuer. Such features may greatly assist the firefighter or rescuer in assessing any risks related to the alarm and in quickly finding and rescuing occupants.

In one embodiment, each opening 1306 may include one or more LED lights positioned there behind such that as a whole, the entire surface of cover plate 1300 and hazard detector 400 becomes or appears to become like an LED screen. In this manner, each opening 1306 functions as a "pixel" of the LED screen. The LED screen or lights may be used to display various information to an occupant or occupants, such as current CO levels, battery status, various messages, alarm source location, short videos, and the like. In some embodiments, the visible patterns of the LED lights can be formed into artistic shapes such as may impress vision in the mind of the viewer. For example, the LED lights may be used to form a famous symbol such as Abe Lincoln, used to form an image of an animal, such as an eagle, used to form various popular trademarks or brand marks, such as an NFL franchise logo, and the like.

Figure 14A:
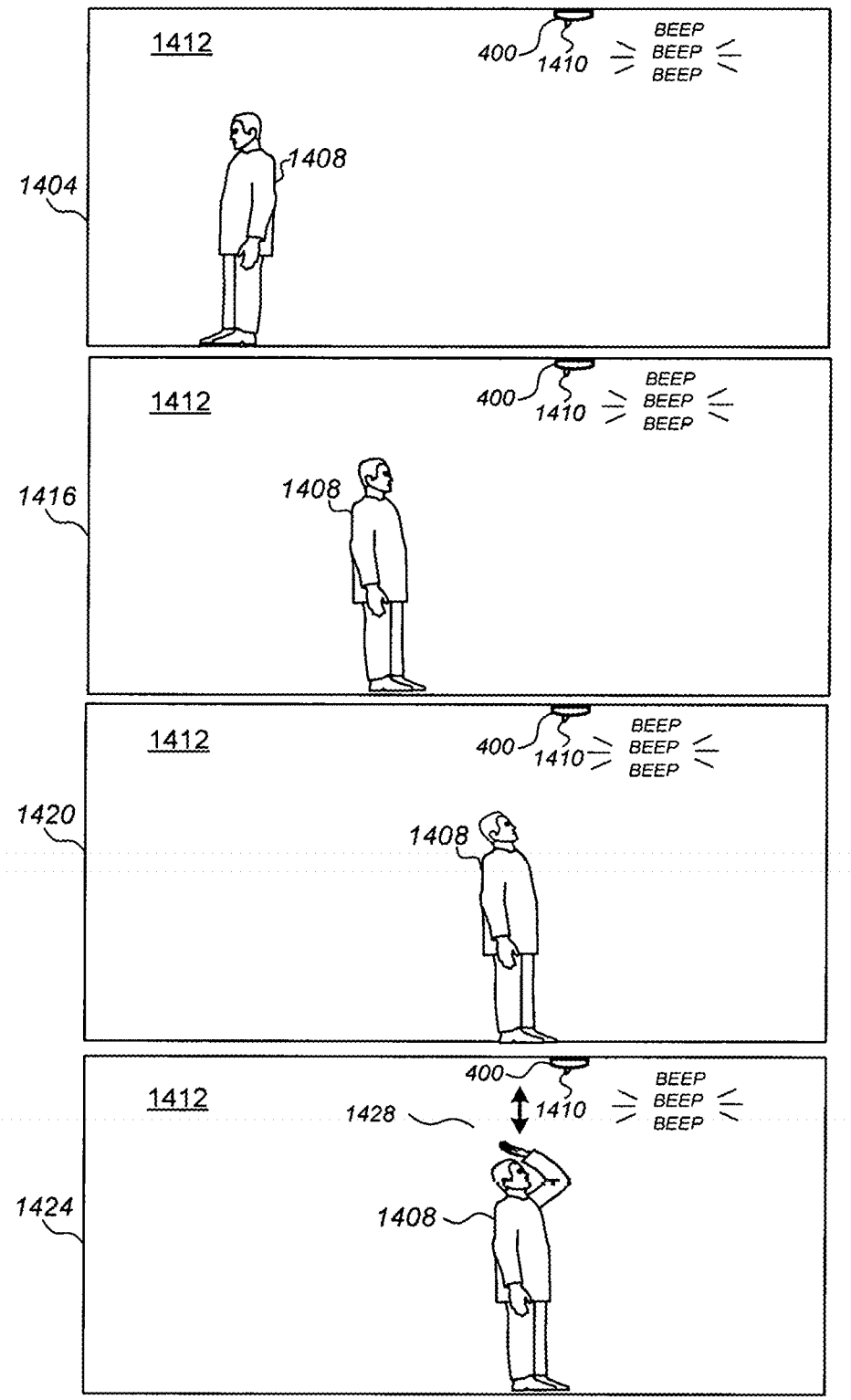
FIGS. 14A-B illustrate a schematic diagram of a silence gesture for remotely deactivating an alarm, according to an embodiment.
Figure 14B:
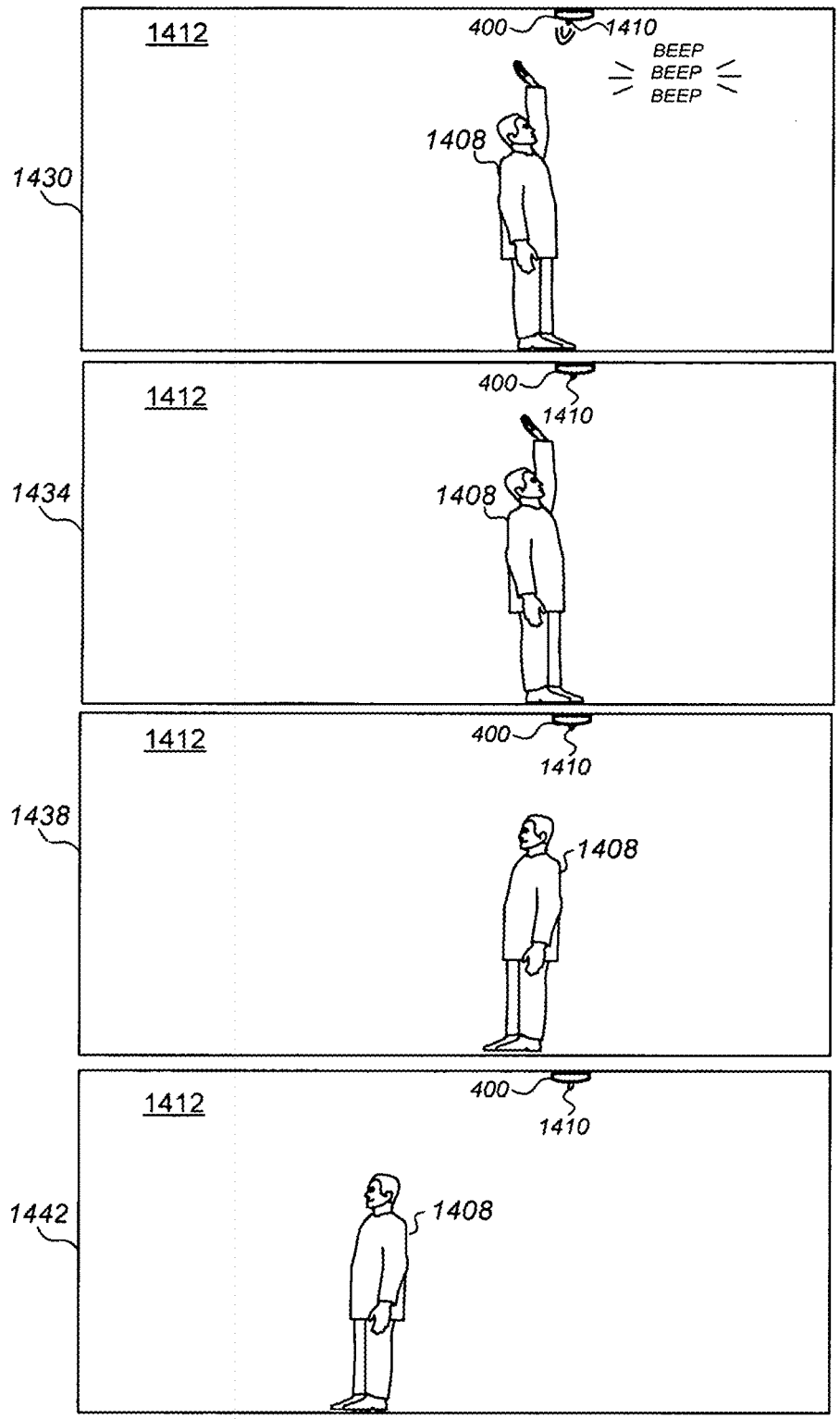

Referring now to FIGS. 14A and 14B, an example "silence gesture" will be described. The method of FIGS. 14A-14B represent one method of implementing a motion-based communication with the hazard detector 400, and is similar in certain respects to the "wave gesture" or "wave hush" referenced above and described more fully in the commonly assigned U.S. Ser. No. 61/847,906, supra. As shown in FIG. 14A at block 1404, an occupant is standing in room 1412 while an alarm in smoke or hazard detector 400 is active and making a "BEEP" sound. A light 1410, such as an LED, is provided on an outer portion of the smart hazard detector 400, such that the occupant 1408 can see the light 1410 when it is turned on. The operation of the light 1410 will be described with reference to FIG. 14B. Suffice to say for FIG. 14A, the light is turned off in blocks 1404 through 1424. As shown at block 1416, the occupant 1408 has walked to a position closer to the smart hazard detector 400, which is mounted out of reach on the ceiling of the room. As shown at block 1420, the occupant 1408 walked to a position even closer to the smart hazard detector 400, such that the occupant 1408 is almost directly under the smart hazard detector 400. As shown at arrow 1428 of block 1424, the occupant 1408, while standing almost directly under the smart hazard detector 400, is beginning to extend an arm upward, toward the smart hazard detector 400.

Referring now to block 1430 of FIG. 14B, the arm of the occupant 1408 is extended upward, toward the smart hazard detector 400, while the occupant is standing almost directly under the smart hazard detector 400. After an alarm sounds and the pulse rate increases, the ultrasonic sensor the smart hazard detector 400 "looks" for a trigger to the "silence gesture" period, which is the amount of time the "silence gesture" must be maintained to deactivate the alarm. According to some embodiments, the trigger is a distance change from a baseline, and to deactivate the alarm the distance change must be maintained for the entire "silence gesture" period (e.g., three seconds). For example, if the baseline is a distance between the sensor and the floor of the room, then the sensor is looking for an object to come in between it and the floor, thereby changing the distance measured by the sensor. In some embodiments, the distance change must be significant enough to ensure that someone is close and likely intends to silence the alarm. For example, if the distance to the floor is ten feet, then the requisite distance change could be eight feet or eighty percent of the original distance. As such, the object would be required to be within two feet of the sensor to trigger the "silence gesture" period, and to deactivate the alarm, the object must remain there for the duration of the period. The requisite distance change can be configured based on the height of the ceiling and based on the height of the occupants, among other things.

Referring still to block 1430, the light 1410 is turned on when the occupant 1408 successfully triggers the "silence gesture" period, thereby signaling to the occupant 1408 to remain in the position for the requisite period, such as three seconds. Here, the hand of the occupant 1408 triggered the "silence gesture" period. A tolerance is built in such that if the occupant 1408 slightly moves and loses but quickly regains the signal, the "silence gesture" period will continue without having to start over. As shown in block 1434, the occupant kept the hand in within the requisite distance of the sensor for the duration of the "silence gesture" period and, thus the alarm has been deactivated, the "BEEP" has stopped, and the light 1410 has turned off. As shown at blocks 1438 and 1442, the occupant 1408 can walk away from the smart hazard detector 400 and resume normal activity.

It should be appreciated that, in the event the smart hazard detector 400 is of a design that receives reliable power from the wiring of the home (rather than being battery powered), a CCD chip could be used to detect the "silence gesture". However, such an arrangement may be less suitable than ultrasonic sensors for battery-powered hazard detectors 400 because the CCD chips and associated processing can consume a relatively large amount of power and may quickly drain the battery. Other possible alternatives to ultrasonic sensors 792 and 794 include passive IR sensors, thermopile (e.g., thermo-cameras), laser-distance measuring, laser and a camera combination because camera looks for dot instead of time of arrival (Doppler shift), and a full on camera and image processing system.

According to some embodiments, to enhance the reliability and effectiveness of the silence gesture, the ultrasonic sensor 792 and/or 794 could work in concert with the PIR sensor to make the sensing even better. For example, when an occupant attempts to silence by placing a hand in field, the PIR will sense this, and thereby trigger the "silence gesture" period. The ultrasonic sensor 792 and/or 794 could also work in concert with the thermopile (e.g., thermo-camera), where both distance change and heat are used to detect the silence gesture. For example, the thermo-camera detects when human hand is nearby and triggers the "silence gesture" period. Further, the ultrasonic sensor 792 and/or 794 could work in concert with the ambient light sensor. For example, when the places a hand in the field and blocks light, then the ambient light sensor know the occupant is nearby and thus triggers the "silence gesture" period.

It should be appreciated that, according to embodiments, similar "gesture" controls can be applied to other smart devices in the home, such as to the smart thermostat, the smart wall switches, etc. For example, there can be gestures for increasing or decreasing temperature controls, for turning on and off lights, HVAC, etc.

Figure 15:
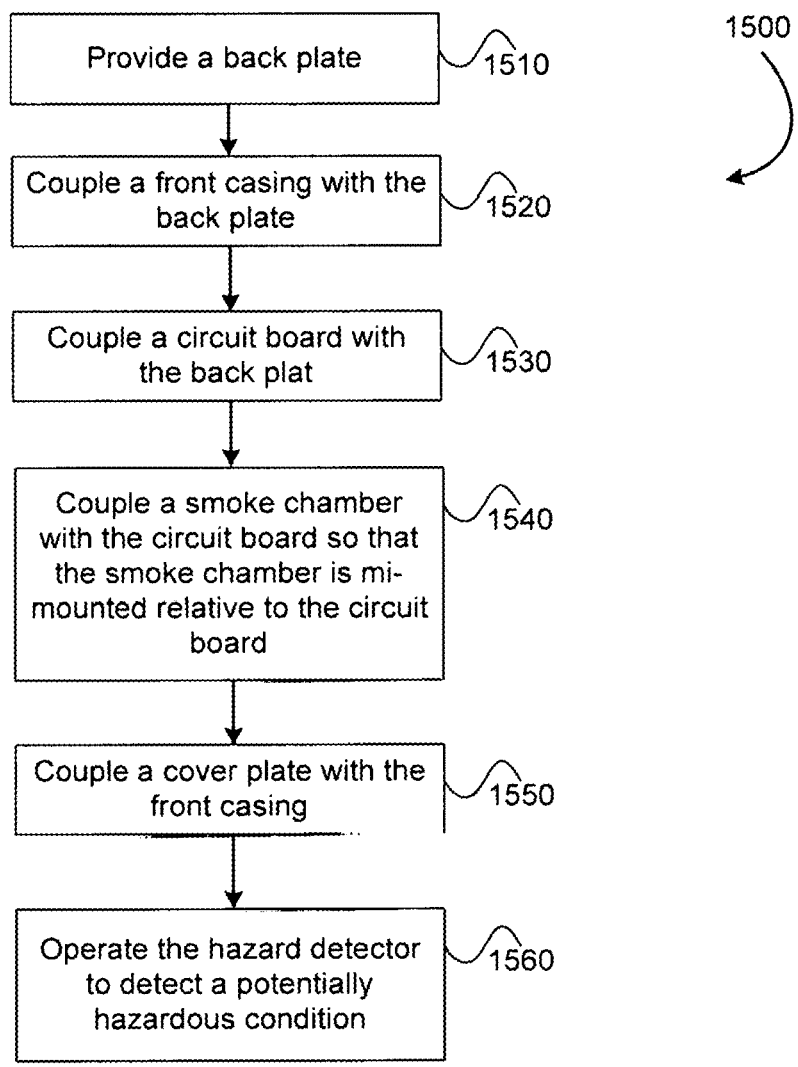
FIG. 15 illustrates a method of manufacturing a hazard detector and/or a method of use thereof, according to an embodiment.

Referring now to FIG. 15, illustrated is a method of manufacturing a hazard detector and/or a method of use thereof. At block 1510 a back plate is provided. As described herein, back plate is couplable with a wall or structure so as to secure the hazard detector relative thereto. At block 1520, a front casing is coupled with the back plate so as to define a housing having an interior region within which components of the hazard detector are contained. At block 1530, a circuit board is coupled with the back plate. A hazard sensor may then be mounted on the circuit board. The hazard sensor may include one or more components that are configured to detect a potentially hazardous condition so as to trigger an alarm device. For example, at block 1540 a smoke chamber is coupled with the circuit board so that the smoke chamber is mid-mounted relative to the circuit board. As described herein, the mounting of the smoke chamber is characterized in that a top surface of the smoke chamber is positioned above a top surface of the circuit board and a bottom surface of the smoke chamber is positioned below a bottom surface of the circuit board. In this configuration smoke and air are flowable into the smoke chamber from both the top surface of the circuit board and the bottom surface of the circuit board.

In some embodiments, one or more additional sensors (e.g. ultrasonic sensors, PIR sensors, and the like) may be mounted on the circuit board. The sensors may be configured to detect the presence and/or movement of objects and/or persons external to the hazard detector. At block 1550, a cover plate may be coupled with the front casing so that the cover plate faces an occupant of a room or area in which the hazard detector is positioned. As described herein, the cover plate includes a relatively large population of relatively small openings. The openings are positioned, configured, and dimensioned so that internal components are substantially hidden from view of the occupant, while air is allowed to substantially freely flow to the one or more internal components through the cover plate in a relatively unimpeded manner, and while the one or more sensors are capable of detecting the objects and/or persons from behind the cover plate. In some embodiments, a collective area of the openings may comprise at least 30% or more of the cover plate. At block 1560, the hazard detector is operated to detect a potentially hazardous condition. Detecting a potentially hazardous condition may include detecting the presence of smoke, detecting abnormally high CO levels, detecting heat levels, and the like.

Figure 17:
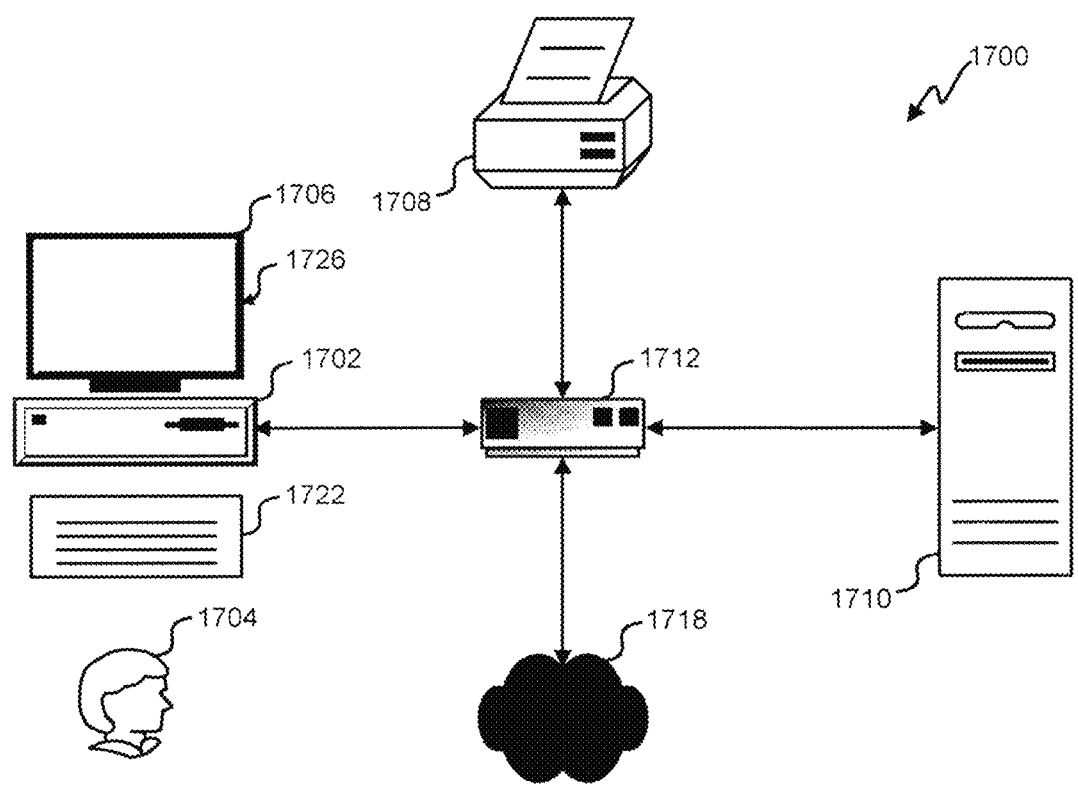
FIG. 17 illustrates a block diagram of an embodiment of a computer system.

Referring next to FIG. 17, an exemplary environment with which embodiments may be implemented is shown with a computer system 1700 that can be used by a user 1704 to remotely control, for example, one or more of the sensor-equipped smart-home devices according to one or more of the embodiments. The computer system 1710 can alternatively be used for carrying out one or more of the server-based processing paradigms described hereinabove can be used as a processing device in a larger distributed virtualized computing scheme for carrying out the described processing paradigms, or for any of a variety of other purposes consistent with the present teachings. The computer system 1700 can include a computer 1702, keyboard 1722, a network router 1712, a printer 1708, and a monitor 1706. The monitor 1706, processor 1702 and keyboard 1722 are part of a computer system 1726, which can be a laptop computer, desktop computer, handheld computer, mainframe computer, etc. The monitor 1706 can be a CRT, flat screen, etc.

A user 1704 can input commands into the computer 1702 using various input devices, such as a mouse, keyboard 1722, track ball, touch screen, etc. If the computer system 1700 comprises a mainframe, a designer 1704 can access the computer 1702 using, for example, a terminal or terminal interface. Additionally, the computer system 1726 may be connected to a printer 1708 and a server 1710 using a network router 1712, which may connect to the Internet 1718 or a WAN.

The server 1710 may, for example, be used to store additional software programs and data. In one embodiment, software implementing the systems and methods described herein can be stored on a storage medium in the server 1710. Thus, the software can be run from the storage medium in the server 1710. In another embodiment, software implementing the systems and methods described herein can be stored on a storage medium in the computer 1702. Thus, the software can be run from the storage medium in the computer system 1726. Therefore, in this embodiment, the software can be used whether or not computer 1702 is connected to network router 1712. Printer 1708 may be connected directly to computer 1702, in which case, the computer system 1726 can print whether or not it is connected to network router 1712.

Figure 18:
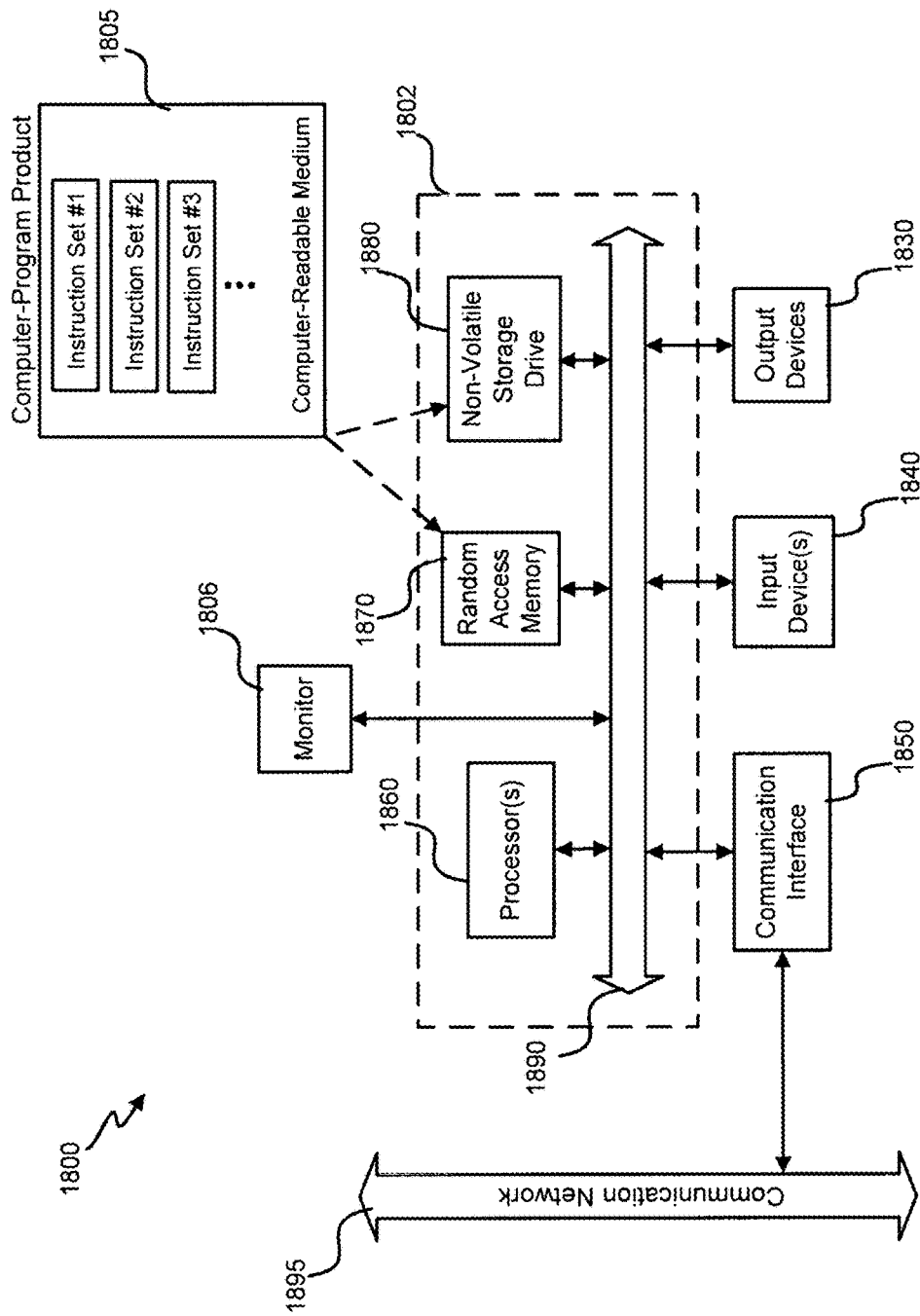
FIG. 18 illustrates a block diagram of an embodiment of a special-purpose computer.

With reference to FIG. 18, an embodiment of a special-purpose computer system 1800 is shown. For example, one or more of intelligent components 116, processing engine 306 and components thereof may be a special-purpose computer system 1800. The above methods may be implemented by computer-program products that direct a computer system to perform the actions of the above-described methods and components. Each such computer-program product may comprise sets of instructions (codes) embodied on a computer-readable medium that directs the processor of a computer system to perform corresponding actions. The instructions may be configured to run in sequential order, or in parallel (such as under different processing threads), or in a combination thereof. After loading the computer-program products on a general purpose computer system 1826, it is transformed into the special-purpose computer system 1800.

Special-purpose computer system 1800 comprises a computer 1802, a monitor 1806 coupled to computer 1802, one or more additional user output devices 1830 (optional) coupled to computer 1802, one or more user input devices 1840 (e.g., keyboard, mouse, track ball, touch screen) coupled to computer 1802, an optional communications interface 1850 coupled to computer 1802, a computer-program product 1805 stored in a tangible computer-readable memory in computer 1802. Computer-program product 1805 directs system 1800 to perform the above-described methods. Computer 1802 may include one or more processors 1860 that communicate with a number of peripheral devices via a bus subsystem 1890. These peripheral devices may include user output device(s) 1830, user input device(s) 1840, communications interface 1850, and a storage subsystem, such as random access memory (RAM) 1870 and non-volatile storage drive 1880 (e.g., disk drive, optical drive, solid state drive), which are forms of tangible computer-readable memory.

Computer-program product 1805 may be stored in non-volatile storage drive 1880 or another computer-readable medium accessible to computer 1802 and loaded into memory 1870. Each processor 1860 may comprise a microprocessor, such as a microprocessor from Intel® or Advanced Micro Devices, Inc.®, or the like. To support computer-program product 1805, the computer 1802 runs an operating system that handles the communications of product 1805 with the above-noted components, as well as the communications between the above-noted components in support of the computer-program product 1805. Exemplary operating systems include Windows® or the like from Microsoft Corporation, Solaris® from Sun Microsystems, LINUX, UNIX, and the like.

User input devices 1840 include all possible types of devices and mechanisms to input information to computer system 1802. These may include a keyboard, a keypad, a mouse, a scanner, a digital drawing pad, a touch screen incorporated into the display, audio input devices such as voice recognition systems, microphones, and other types of input devices. In various embodiments, user input devices 1840 are typically embodied as a computer mouse, a trackball, a track pad, a joystick, wireless remote, a drawing tablet, a voice command system. User input devices 1840 typically allow a user to select objects, icons, text and the like that appear on the monitor 1806 via a command such as a click of a button or the like. User output devices 1830 include all possible types of devices and mechanisms to output information from computer 1802. These may include a display (e.g., monitor 1806), printers, non-visual displays such as audio output devices, etc.

Communications interface 1850 provides an interface to other communication networks and devices and may serve as an interface to receive data from and transmit data to other systems, WANs and/or the Internet 1718. Embodiments of communications interface 1850 typically include an Ethernet card, a modem (telephone, satellite, cable, ISDN), a (asynchronous) digital subscriber line (DSL) unit, a FireWire® interface, a USB® interface, a wireless network adapter, and the like. For example, communications interface 1850 may be coupled to a computer network, to a FireWire® bus, or the like. In other embodiments, communications interface 1850 may be physically integrated on the motherboard of computer 1702, and/or may be a software program, or the like.

RAM 1870 and non-volatile storage drive 1880 are examples of tangible computer-readable media configured to store data such as computer-program product embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 1870 and non-volatile storage drive 1880 may be configured to store the basic programming and data constructs that provide the functionality of various embodiments of the present invention, as described above.

Software instruction sets that provide the functionality of the present invention may be stored in RAM 1870 and non-volatile storage drive 1880. These instruction sets or code may be executed by the processor(s) 1860. RAM 1870 and non-volatile storage drive 1880 may also provide a repository to store data and data structures used in accordance with the present invention. RAM 1870 and non-volatile storage drive 1880 may include a number of memories including a main random access memory (RAM) to store of instructions and data during program execution and a read-only memory (ROM) in which fixed instructions are stored. RAM 1870 and non-volatile storage drive 1880 may include a file storage subsystem providing persistent (non-volatile) storage of program and/or data files. RAM 1870 and non-volatile storage drive 1880 may also include removable storage systems, such as removable flash memory.

Bus subsystem 1890 provides a mechanism to allow the various components and subsystems of computer 1802 communicate with each other as intended. Although bus subsystem 1890 is shown schematically as a single bus, alternative embodiments of the bus subsystem may utilize multiple busses or communication paths within the computer 1802.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to, portable or fixed storage devices, optical storage devices, wireless channels, and/or various other storage mediums capable of storing that contain or carry instruction(s) and/or data.

Having described several embodiments, it will be recognized by those of skill in the art that various modifications, alternative constructions, and equivalents may be used without departing from the spirit of the invention. By way of non-limiting example, although it has been found particularly advantageous to provide one or more of the above-described event-triggered modulated-light-glow device status communication methods in the context of a hazard detector not outfitted with a dot-matrix display, it is to be appreciated that the scope of the present teachings is not so limited, and that in other embodiments such event-triggered modulated-light-glow device status communication methods can be provided in a hazard detection unit that does provide a dot-matrix display that can be read at close-up range. For some embodiments, the above-described event-triggered modulated-light-glow device status communication methods can be provided by the dot-matrix display itself without requiring a separate light ring or other light-source pattern, wherein the visual effects of the above-described event-triggered modulated-light-glow device status communication methods are provided by the dot-matrix screen itself. In still other embodiments, the hazard detector uses its presence detection and proximity detection modules to determine whether a detected occupant is close enough to the unit to read the dot-matrix display, wherein the status information is set forth in text form or other more conventional electronic display form if the user is close enough to read it, but wherein the status information is set forth using modulated-light-glow methods similar to those described hereinabove if the user is not close enough to read the conventional dot-matrix display form of the information. By way of further non-limiting example, although it has been found particularly advantageous to provide one or more of the above-described user interface buttons and event-triggered modulated-light-glow device status communication methods in the context of a household hazard detector, it is to be appreciated that the hardware and software for carrying out such apparatus and methods can be provided in conjunction with any of a variety of different household devices including, but not limited to, thermostats, security panels, security-related devices, security-related displays, household appliances, network communication equipment, lighting fixtures, household service robots, HVAC equipment, irrigation equipment, entertainment devices and systems, doorbell or other entryway automation systems, and more generally any of the devices or systems set forth or associated with the smart-home environment of FIG. 1, supra, without departing from the scope of the present teachings.

By way of still further non-limiting example, although it has been found particularly advantageous to provide one or more of the above-described pathlighting functionalities, up to and including a user-adaptive and ambient-light-adaptive pathlighting functionality, in conjunction with a household hazard detector, with one particular advantage being directed to increasing the ubiquity of household hazard detectors (a benefit to both private household safety and public safety) by increasing their popularity by favorable impressions upon users by virtue of the pathlighting functionality, with another particular advantage conversely to improve night time safety by virtue of promoting at least as many pathlighting devices as there are hazard detectors in homes, it is to be appreciated that the hardware and software for carrying out such pathlighting methods can be provided in conjunction with any of a variety of different household devices including, but not limited to, thermostats, security panels, security-related devices, security-related displays, household appliances, network communication equipment, lighting fixtures, household service robots, HVAC equipment, irrigation equipment, entertainment devices and systems, doorbell or other entryway automation systems, and more generally any of the devices or systems set forth or associated with the smart-home environment of FIG. 1, supra, without departing from the scope of the present teachings. Additionally, a number of well-known processes and elements have not been described in order to avoid unnecessarily obscuring the present invention. Accordingly, the above description should not be taken as limiting the scope of the invention.

Where a range of values is provided, it is to be understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:
1. A front casing of a hazard detector comprising:
   a body portion having an outwardly facing surface that faces a room within which the hazard detector is positioned and an inwardly facing surface that faces opposite the outwardly facing surface, the body portion being couplable with a back plate to define a housing having an interior region within which components of the hazard detector are contained; and
   a button portion coupled with the body portion via a plurality of arms that allow the button portion to be axially movable relative to the body portion so as to activate a switch positioned axially behind the button portion to provide input to the hazard detector from a user, the button portion having a plurality of tabs that extend radially outward from a peripheral edge of the button portion;
   wherein each tab is positioned under and contacts the inwardly facing surface of the body portion such that when a force is applied to the button portion at a position substantially offset from a central axis of the button portion, the button portion pivots about one or more contact points between the tabs and the inwardly facing surface of the body portion; and wherein the plurality of arms are coupled with the button portion and the body portion so as to bias the button portion axially outward relative to the body portion to press the plurality of tabs against the inwardly facing surface of the body portion.

2. The front casing of claim 1, wherein each tab of the plurality of tabs is positioned under a flange of the body portion.

3. The front casing of claim 1, wherein each of the plurality of arms includes a proximal end, a distal end, and a main body extending therebetween, and wherein each of the plurality of arms are fixed to the body portion at the proximal end and fixed to the button portion at the distal end such that the main body extends circumferentially around a portion of the button portion.

4. The front casing of claim 3, wherein the distal end of each arm is coupled with a tab of the button portion.

5. The front casing of claim 1, wherein the body portion comprises a relatively large population of relatively small openings such that air is allowed to substantially freely flow to one or more components contained within the housing through the body portion in a relatively unimpeded manner, wherein a collective area of said openings of said body portion is between about 20% and 40% of the body portion.

6. The front casing of claim 1, wherein the button portion is positioned substantially centrally relative to the body portion.

7. The front casing of claim 6, wherein the button portion comprises four radially extending tabs that are each positioned under and contact the inwardly facing surface of the body portion so as to define four pivot points about which the button portion is pivotable.

8. The front casing of claim 1, wherein the button portion is integrally formed with the body portion so that the body portion and button portion comprise a single component.

9. The front casing of claim 1, wherein a Fresnel lens member is attached to the button portion, the Fresnel lens member functioning as a pressable button and as a lens for a passive infrared (PIR) sensor positioned axially inward of the Fresnel lens member.

10. A front casing of a hazard detector comprising:
a body portion having an outwardly facing surface that faces a room within which the hazard detector is positioned and an inwardly facing surface that faces opposite the outwardly facing surface, the body portion being couplable with a back plate to define a housing having an interior region within which components of the hazard detector are contained; and
a button portion coupled with the body portion via a plurality of arms that allow the button portion to be axially movable relative to the body portion, the button portion being coupled with the body portion so that one or more tabs that extend radially outward from a peripheral edge of the button portion are positioned under and contact the inwardly facing surface of the body portion;
wherein when a force is applied to the button portion substantially off-axis from a central axis of the button portion, the button portion pivots about one or more points of contact between the one or more tabs and the inwardly facing surface of the body portion; and
wherein the plurality of arms couple the button portion to the body portion such that the button portion is biased axially outward relative to the body portion.

11. The front casing of claim 10, wherein a Fresnel lens member is attached to the button portion, the Fresnel lens member functioning as a pressable button and as a lens for a passive infrared (PIR) sensor positioned axially inward of the Fresnel lens member.

12. The front casing of claim 11, wherein the PIR sensor is positioned on an outwardly facing surface of the button portion.

13. The front casing of claim 10, wherein the body portion comprises a relatively large population of relatively small openings such that air is allowed to substantially freely flow to one or more components contained within the housing through the body portion in a relatively unimpeded manner, wherein a collective area of said openings of said body portion is between about 20% and 40% of the body portion.

14. The front casing of claim 10, wherein the button portion is positioned substantially centrally relative to the body portion.

15. The front casing of claim 1, wherein the button portion is integrally formed with the body portion so that the body portion and button portion comprise a single component.

16. A method of making a casing having a pressable button portion, the method comprising:
forming a casing component having:
a body portion comprising an outwardly facing surface and an inwardly facing surface opposite the outwardly facing surface;
a button portion comprising a plurality of tabs that extend radially outward from a peripheral edge of the button portion; and
a plurality of arms that attach the button portion to the body portion with the plurality of tabs being positioned axially outward relative to the inwardly facing surface of the body portion, the plurality of arms allowing the button portion to be movable relative to the body portion; and
repositioning the button portion relative to the body portion so that the plurality of tabs are positioned axially inward of the inwardly facing surface of the body portion;
wherein repositioning the button portion causes the plurality of arms to bias the button portion axially outward relative to the body portion so that the plurality of tabs press against the inwardly facing surface of the body portion.

17. The method of claim 16, wherein contact between the plurality of tabs and the inwardly facing surface of the body portion cause the button portion to pivot relative to the body portion when a force is applied to the button portion substantially off-axis from a central axis of the button portion.

18. The method of claim 16, wherein the body portion, button portion, and the plurality of arms are integrally molded as a single component.

19. The method of claim 16, further comprising coupling a Fresnel lens member to the button portion, the Fresnel lens member functioning as a pressable button and as a lens for a passive infrared (PIR) sensor positioned axially inward of the Fresnel lens member.

20. A method of making a casing having a pressable button portion, the method comprising:
forming a casing component having a body portion and a button portion, the button portion being coupled with the body via a plurality of arms that allow the button portion to be axially movable relative to the body portion, the button portion having a plurality of tabs that extend radially outwardly from a peripheral edge of the button portion,the casing component being formed such that the one or more tabs of the button portion are positioned axially outward relative to an inwardly facing surface of the body portion; and repositioning the button portion relative to the body portion such that the one or more tabs of the button portion are positioned axially inward of the inwardly facing surface of the body portion;

wherein repositioning the button portion relative to the body portion causes the plurality of arms to bias the button portion axially outward relative to the body portion so that the one or more tabs are pressed against the inwardly facing surface of the body portion.

21. The method of claim 20, further comprising coupling a Fresnel lens member to the button portion, the Fresnel lens member functioning as a pressable button and as a lens for a passive infrared (PIR) sensor positioned axially inward of the Fresnel lens member.

22. The method of claim 20, wherein the body portion and the button portion are integrally molded as a single component.

* * * * *